United States Patent
Persicaner et al.

(10) Patent No.: US 10,806,740 B2
(45) Date of Patent: *Oct. 20, 2020

(54) NATURAL COMBINATION HORMONE REPLACEMENT FORMULATIONS AND THERAPIES

(71) Applicant: TherapeuticsMD, Inc., Boca Raton, FL (US)

(72) Inventors: Peter H. R. Persicaner, Boca Raton, FL (US); Brian A. Bernick, Boca Raton, FL (US); Julia M. Amadio, Boca Raton, FL (US)

(73) Assignee: TherapeuticsMD, Inc., Boca Raton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/512,046

(22) Filed: Oct. 10, 2014

(65) Prior Publication Data

US 2015/0031654 A1    Jan. 29, 2015

Related U.S. Application Data

(63) Continuation-in-part of application No. 13/843,428, filed on Mar. 15, 2013, which is a continuation-in-part of application No. 13/684,002, filed on Nov. 21, 2012, now Pat. No. 8,633,178.

(60) Provisional application No. 61/661,302, filed on Jun. 18, 2012, provisional application No. 61/662,265, filed on Jun. 20, 2012, provisional application No. 61/889,483, filed on Oct. 10, 2013.

(51) Int. Cl.
  *A61K 31/57* (2006.01)
  *A61K 31/565* (2006.01)
  *A61K 9/48* (2006.01)

(52) U.S. Cl.
  CPC ............ *A61K 31/57* (2013.01); *A61K 9/4858* (2013.01); *A61K 31/565* (2013.01)

(58) Field of Classification Search
  None
  See application file for complete search history.

(56) References Cited

U.S. PATENT DOCUMENTS

| | | |
|---|---|---|
| 1,967,351 A | 1/1934 | Doisy |
| 2,232,438 A | 2/1941 | Butenandt |
| 2,379,832 A | 7/1945 | Serini et al. |
| 2,649,399 A | 8/1953 | Beall et al. |
| 3,198,707 A | 8/1965 | Nomine et al. |
| 3,478,070 A | 11/1969 | Stein et al. |
| 3,526,648 A | 9/1970 | Bertin et al. |
| 3,710,795 A | 1/1973 | Higuchi et al. |
| 3,729,560 A | 4/1973 | Hagerman |
| 3,729,566 A | 4/1973 | Ericsson et al. |
| 3,755,573 A | 8/1973 | Berman |
| 3,755,575 A | 8/1973 | Lerner |
| 3,903,880 A | 9/1975 | Higuchi et al. |
| 3,916,898 A | 11/1975 | Robinson |
| 3,916,899 A | 11/1975 | Theeuwes et al. |
| 3,921,636 A | 11/1975 | Zaffaroni |
| 3,923,997 A | 12/1975 | Meuly |
| 3,948,254 A | 4/1976 | Zaffaroni |
| 3,971,367 A | 6/1976 | Zaffaroni |
| 3,977,404 A | 8/1976 | Theeuwes |
| 3,993,072 A | 11/1976 | Zaffaroni |
| 4,008,719 A | 2/1977 | Theeuwes et al. |
| 4,012,496 A | 3/1977 | Schopflin et al. |
| 4,014,334 A | 3/1977 | Theeuwes et al. |
| 4,014,987 A | 3/1977 | Heller et al. |
| 4,016,251 A | 8/1977 | Higuchi et al. |
| 4,071,623 A | 1/1978 | van der Vies |
| 4,093,709 A | 6/1978 | Choi et al. |
| 4,154,820 A | 5/1979 | Simoons |
| 4,155,991 A | 5/1979 | Schopflin et al. |
| 4,196,188 A | 4/1980 | Besins |
| 4,215,691 A | 8/1980 | Wong |
| 4,237,885 A | 12/1980 | Wong et al. |
| 4,310,510 A | 1/1982 | Sherman et al. |
| 4,327,725 A | 5/1982 | Cortese et al. |
| 4,372,951 A | 2/1983 | Vorys |
| 4,384,096 A | 5/1983 | Sonnabend |
| 4,393,871 A | 7/1983 | Vorhauer et al. |
| 4,402,695 A | 9/1983 | Wong |
| 4,423,151 A | 12/1983 | Baranczuk |
| 4,449,980 A | 5/1984 | Millar et al. |
| 4,610,687 A | 9/1986 | Fogwell |
| 4,629,449 A | 12/1986 | Wong |
| 4,732,763 A | 3/1988 | Beck et al. |
| 4,738,957 A | 4/1988 | Laurent et al. |

(Continued)

FOREIGN PATENT DOCUMENTS

| | | |
|---|---|---|
| BR | PI1001367-9 A2 | 7/2012 |
| CA | 2044371 A1 | 12/1991 |
| CA | 2612380 C | 6/2017 |
| CN | 102258455 A | 11/2011 |
| EP | 0261429 A1 | 3/1988 |
| EP | 0275716 A1 | 7/1988 |
| EP | 0279977 A2 | 8/1988 |
| EP | 0622075 A1 | 11/1994 |
| EP | 0750495 B1 | 1/1997 |

(Continued)

OTHER PUBLICATIONS

US 6,214,374 B1, 04/2001, Schmirler et al. (withdrawn)

(Continued)

*Primary Examiner* — Dennis J Parad
(74) *Attorney, Agent, or Firm* — Kilpatrick Townsend & Stockton LLP

(57) ABSTRACT

Pharmaceutical formulations for co-administering estradiol and progesterone are provided herein. In some embodiments, the formulation comprises solubilized estradiol, suspended progesterone, and a medium chain (C6-C12) oil.

17 Claims, 8 Drawing Sheets

(56) References Cited

U.S. PATENT DOCUMENTS

| | | |
|---|---|---|
| 4,756,907 A | 7/1988 | Beck et al. |
| 4,762,717 A | 8/1988 | Crowley, Jr. |
| 4,788,062 A | 11/1988 | Gale et al. |
| 4,816,257 A | 3/1989 | Buster et al. |
| 4,822,616 A | 4/1989 | Zimmermann et al. |
| 4,865,848 A | 9/1989 | Cheng et al. |
| 4,900,734 A | 2/1990 | Maxson et al. |
| 4,906,475 A | 3/1990 | Kim |
| 4,942,158 A | 7/1990 | Sarpotdar et al. |
| 4,961,931 A | 10/1990 | Wong |
| 5,030,629 A | 7/1991 | Rajadhyaksha |
| 5,043,331 A | 8/1991 | Hirvonen et al. |
| 5,059,426 A | 10/1991 | Chiang |
| 5,064,654 A | 11/1991 | Berner et al. |
| 5,108,995 A | 4/1992 | Casper |
| 5,128,138 A | 7/1992 | Blank |
| 5,130,137 A | 7/1992 | Crowley, Jr. |
| 5,140,021 A | 8/1992 | Maxson et al. |
| 5,208,225 A | 5/1993 | Boissonneault et al. |
| 5,211,952 A | 5/1993 | Spicer et al. |
| 5,252,334 A | 10/1993 | Chiang et al. |
| 5,280,023 A | 1/1994 | Ehrlich et al. |
| 5,288,496 A | 2/1994 | Lewis |
| 5,340,584 A | 8/1994 | Spicer et al. |
| 5,340,585 A | 8/1994 | Pike et al. |
| 5,340,586 A | 8/1994 | Pike et al. |
| 5,362,497 A | 8/1994 | Yamada et al. |
| 5,382,573 A | 1/1995 | Casper |
| 5,393,528 A | 2/1995 | Staab |
| 5,393,529 A | 2/1995 | Hoffmann et al. |
| 5,419,910 A | 5/1995 | Lewis |
| 5,453,279 A | 9/1995 | Lee et al. |
| 5,468,736 A | 11/1995 | Hodgen |
| 5,474,783 A | 12/1995 | Miranda et al. |
| 5,480,776 A | 1/1996 | Dullien |
| 5,514,673 A | 5/1996 | Heckenmueller et al. |
| 5,516,528 A | 5/1996 | Hughes et al. |
| 5,527,534 A | 6/1996 | Myhling |
| 5,529,782 A | 6/1996 | Staab |
| 5,538,736 A | 7/1996 | Barth |
| 5,543,150 A | 8/1996 | Bologna et al. |
| 5,547,948 A | 8/1996 | Barcomb |
| 5,556,635 A | 9/1996 | Grognet |
| 5,565,199 A | 10/1996 | Page et al. |
| 5,567,831 A | 10/1996 | Li |
| 5,569,652 A | 10/1996 | Beier et al. |
| 5,580,572 A | 12/1996 | Liorzou |
| 5,582,592 A | 12/1996 | Kendrick |
| 5,585,370 A | 12/1996 | Casper |
| 5,595,759 A | 1/1997 | Wright et al. |
| 5,595,970 A | 1/1997 | Garfield et al. |
| 5,605,702 A | 2/1997 | Math |
| 5,607,691 A | 3/1997 | Solas |
| 5,607,693 A | 3/1997 | Bonte |
| 5,609,617 A | 3/1997 | Cady |
| 5,620,705 A | 4/1997 | Dong et al. |
| 5,626,866 A | 5/1997 | Heiber |
| 5,629,021 A | 5/1997 | Wright |
| 5,633,011 A | 5/1997 | Dong et al. |
| 5,633,242 A | 5/1997 | Oettel et al. |
| 5,639,743 A | 6/1997 | Kaswan et al. |
| 5,645,856 A | 6/1997 | Lacy et al. |
| 5,653,983 A | 8/1997 | Bonte |
| 5,656,286 A | 8/1997 | Miranda et al. |
| 5,660,839 A | 8/1997 | Allec |
| 5,662,927 A | 9/1997 | Ehrlich |
| 5,663,160 A | 9/1997 | Dumas |
| 5,676,968 A | 10/1997 | Lipp et al. |
| 5,677,292 A | 10/1997 | Li et al. |
| 5,686,097 A | 11/1997 | Crisologo |
| 5,693,335 A | 12/1997 | Xia |
| 5,694,947 A | 12/1997 | Lehtinen et al. |
| 5,700,480 A | 12/1997 | Hille et al. |
| 5,709,844 A | 1/1998 | Arbeit et al. |
| 5,719,197 A | 2/1998 | Mantelle |
| 5,735,801 A | 4/1998 | Caillouette |
| 5,739,176 A | 4/1998 | Dunn et al. |
| 5,744,463 A | 4/1998 | Bair |
| 5,747,058 A | 5/1998 | Tipton et al. |
| 5,762,614 A | 6/1998 | Caillouette |
| 5,770,176 A | 6/1998 | Nargessi |
| 5,770,219 A | 6/1998 | Chiang et al. |
| 5,770,220 A | 6/1998 | Meconi |
| 5,770,227 A | 6/1998 | Dong |
| 5,776,495 A | 7/1998 | Duclos et al. |
| 5,780,044 A | 7/1998 | Tipton |
| 5,780,050 A | 7/1998 | Jain |
| 5,788,980 A | 8/1998 | Nabahi |
| 5,788,984 A | 8/1998 | Schmidt Gollwitzer |
| 5,789,442 A | 8/1998 | Garfield et al. |
| 5,811,416 A | 9/1998 | Chwalisz et al. |
| 5,811,547 A | 9/1998 | Nakamichi et al. |
| 5,814,329 A | 9/1998 | Shah |
| 5,820,878 A | 10/1998 | Shinmura |
| 5,827,200 A | 10/1998 | Caillouette |
| 5,840,327 A | 11/1998 | Gale |
| 5,843,468 A | 12/1998 | Yum |
| 5,843,979 A | 12/1998 | Wille |
| 5,858,394 A | 1/1999 | Lipp |
| 5,863,552 A | 1/1999 | Yue |
| 5,866,603 A | 2/1999 | Li et al. |
| 5,869,084 A | 2/1999 | Paradissis et al. |
| 5,882,676 A | 3/1999 | Yum |
| 5,885,612 A | 3/1999 | Meconi |
| 5,888,533 A | 3/1999 | Dunn |
| 5,891,462 A | 4/1999 | Carrara |
| 5,891,868 A | 4/1999 | Cummings et al. |
| 5,898,038 A | 4/1999 | Yallampalli et al. |
| 5,902,603 A | 5/1999 | Chen |
| 5,904,931 A | 5/1999 | Gunther |
| 5,906,830 A | 5/1999 | Farinas |
| 5,912,010 A | 6/1999 | Wille |
| 5,916,176 A | 6/1999 | Caillouette |
| RE36,247 E | 7/1999 | Plunkett et al. |
| 5,919,477 A | 7/1999 | Bevan |
| 5,922,349 A | 7/1999 | Elliesen et al. |
| 5,928,666 A | 7/1999 | Farinas et al. |
| 5,942,243 A | 8/1999 | Shah |
| 5,942,531 A | 8/1999 | Diaz et al. |
| 5,952,000 A | 9/1999 | Fikstad |
| 5,958,446 A | 9/1999 | Miranda et al. |
| 5,962,445 A | 10/1999 | Stewart |
| 5,968,919 A | 10/1999 | Gyurik |
| 5,972,372 A | 10/1999 | Saleh et al. |
| 5,985,311 A | 11/1999 | Cordes |
| 5,985,850 A | 11/1999 | Falk |
| 5,985,861 A | 11/1999 | Levine et al. |
| 5,993,856 A | 11/1999 | Ragavan et al. |
| 5,989,568 A | 12/1999 | De Lacharriere |
| 6,001,846 A | 12/1999 | Edwards et al. |
| 6,007,835 A | 12/1999 | Bon Lapillonne |
| 6,010,715 A | 1/2000 | Pollock |
| 6,013,276 A | 1/2000 | Teillaud |
| 6,022,562 A | 2/2000 | Autant et al. |
| 6,024,974 A | 2/2000 | Li |
| 6,024,976 A | 2/2000 | Miranda et al. |
| 6,028,057 A | 2/2000 | Burns |
| 6,030,948 A | 2/2000 | Mann |
| 6,039,968 A | 3/2000 | Nabahi |
| 6,040,340 A | 3/2000 | Garfield |
| 6,056,972 A | 5/2000 | Hermsmeyer |
| 6,060,077 A | 5/2000 | Meignant |
| 6,068,853 A | 5/2000 | Berner |
| 6,074,625 A | 6/2000 | Hawthorne et al. |
| 6,077,531 A | 6/2000 | Salin-Drouin |
| 6,080,118 A | 6/2000 | Blythe |
| 6,083,178 A | 7/2000 | Caillouette |
| 6,086,916 A | 7/2000 | Agnus et al. |
| 6,087,352 A | 7/2000 | Trout |
| 6,090,404 A | 7/2000 | Meconi |
| 6,096,338 A | 7/2000 | Lacy et al. |
| 6,106,848 A | 8/2000 | Willcox |
| 6,117,446 A | 9/2000 | Place |
| 6,117,450 A | 9/2000 | Dittgen et al. |

(56) References Cited

U.S. PATENT DOCUMENTS

| | | |
|---|---|---|
| 6,124,362 A | 9/2000 | Bradbury |
| 6,133,251 A | 10/2000 | Dittgen et al. |
| 6,133,320 A | 10/2000 | Yallampalli et al. |
| 6,139,868 A | 10/2000 | Hoffmann |
| 6,139,873 A | 10/2000 | Hughes, Jr. et al. |
| 6,149,935 A | 11/2000 | Tenzel |
| 6,153,216 A | 11/2000 | Cordes et al. |
| 6,165,491 A | 12/2000 | Grasset et al. |
| 6,165,975 A | 12/2000 | Adams et al. |
| 6,187,323 B1 | 2/2001 | Aiache |
| 6,187,339 B1 | 2/2001 | de Haan et al. |
| 6,190,331 B1 | 2/2001 | Caillouette |
| 6,201,072 B1 | 3/2001 | Rathi et al. |
| 6,217,886 B1 | 4/2001 | Reubinstein |
| 6,225,297 B1 | 5/2001 | Stockemann |
| 6,227,202 B1 | 5/2001 | Matapurkar |
| 6,228,383 B1 | 5/2001 | Hansen |
| 6,228,852 B1 | 5/2001 | Shaak |
| 6,242,509 B1 | 6/2001 | MacQueen |
| 6,245,811 B1 | 6/2001 | Horrobin |
| 6,262,115 B1 | 7/2001 | Guittard et al. |
| 6,267,984 B1 | 7/2001 | Hamlin |
| 6,274,165 B1 | 8/2001 | Meconi |
| 6,277,418 B1 | 8/2001 | Marakverich et al. |
| 6,283,927 B1 | 9/2001 | Caillouette |
| 6,284,263 B1 | 9/2001 | Place |
| 6,287,588 B1 | 9/2001 | Shih et al. |
| 6,287,693 B1 | 9/2001 | Savoir et al. |
| 6,294,188 B1 | 9/2001 | Ragavan et al. |
| 6,294,192 B1 | 9/2001 | Patel et al. |
| 6,294,550 B1 | 9/2001 | Place et al. |
| 6,299,900 B1 | 10/2001 | Reed et al. |
| 6,303,132 B1 | 10/2001 | Nelson |
| 6,303,588 B1 | 10/2001 | Danielov |
| 6,306,841 B1 | 10/2001 | Place et al. |
| 6,306,914 B1 | 10/2001 | de Ziegler et al. |
| 6,309,669 B1 | 10/2001 | Setterstrom et al. |
| 6,309,848 B1 | 10/2001 | Howett et al. |
| 6,312,703 B1 | 11/2001 | Orthoefer |
| 6,328,987 B1 | 12/2001 | Marini |
| 6,342,491 B1 | 1/2002 | Dey et al. |
| 6,344,211 B1 | 2/2002 | Hille |
| 6,372,209 B1 | 4/2002 | Chrisope |
| 6,372,245 B1 | 4/2002 | Vo |
| 6,372,246 B1 | 4/2002 | Wei et al. |
| 6,387,390 B1 | 5/2002 | Deaver et al. |
| 6,402,705 B1 | 6/2002 | Caillouette |
| 6,416,778 B1 | 7/2002 | Ragavan et al. |
| 6,420,352 B1 | 7/2002 | Knowles |
| 6,423,039 B1 | 7/2002 | Rathbone et al. |
| 6,423,683 B1 | 7/2002 | Heaton et al. |
| 6,432,438 B1 | 8/2002 | Shukla |
| 6,436,633 B1 | 8/2002 | Kreider et al. |
| 6,440,454 B1 | 8/2002 | Santoro et al. |
| 6,444,224 B1 | 9/2002 | Rathbone et al. |
| 6,444,234 B1 | 9/2002 | Kirby et al. |
| 6,451,300 B1 | 9/2002 | Leyba |
| 6,451,339 B2 | 9/2002 | Patel et al. |
| 6,451,779 B1 | 9/2002 | Hesch |
| 6,455,246 B1 | 9/2002 | Howett et al. |
| 6,455,517 B1 | 9/2002 | Tanabe et al. |
| 6,465,004 B1 | 10/2002 | Houze |
| 6,465,005 B1 | 10/2002 | Biali |
| 6,465,006 B1 | 10/2002 | Zhang |
| 6,468,526 B2 | 10/2002 | Chrisope |
| 6,469,016 B1 | 10/2002 | Place et al. |
| 6,472,434 B1 | 10/2002 | Place et al. |
| 6,479,232 B1 | 11/2002 | Howett et al. |
| 6,495,160 B2 | 12/2002 | Esposito |
| 6,500,814 B1 | 12/2002 | Hesch |
| 6,503,896 B1 | 1/2003 | Tanabe et al. |
| 6,511,969 B1 | 1/2003 | Hermsmeyer |
| 6,521,250 B2 | 2/2003 | Seibertz |
| 6,526,980 B1 | 3/2003 | Tracy et al. |
| 6,528,094 B1 | 3/2003 | Savoir et al. |
| 6,531,149 B1 | 3/2003 | Meconi |
| 6,537,580 B1 | 3/2003 | Savoir et al. |
| 6,538,039 B2 | 3/2003 | Laurent |
| 6,544,196 B2 | 4/2003 | Caillouette |
| 6,544,553 B1 | 4/2003 | Hsia et al. |
| 6,548,053 B1 | 4/2003 | Murray |
| 6,548,491 B2 | 4/2003 | Tanabe et al. |
| 6,551,611 B2 | 4/2003 | Elliesen et al. |
| 6,555,131 B1 | 4/2003 | Wolff |
| 6,562,367 B1 | 5/2003 | Wolff |
| 6,562,370 B2 | 5/2003 | Luo |
| 6,562,790 B2 | 5/2003 | Chein |
| 6,569,463 B2 | 5/2003 | Patel et al. |
| 6,583,129 B1 | 6/2003 | Mazer et al. |
| 6,586,006 B2 | 7/2003 | Roser et al. |
| 6,589,549 B2 | 7/2003 | Shih et al. |
| 6,593,317 B1 | 7/2003 | de Ziegler et al. |
| 6,599,519 B1 | 7/2003 | Seo |
| 6,610,325 B1 | 8/2003 | Meignant |
| 6,610,652 B2 | 8/2003 | Adams et al. |
| 6,610,670 B2 | 8/2003 | Backensfeld et al. |
| 6,610,674 B1 | 8/2003 | Schreiber |
| 6,635,274 B1 | 10/2003 | Carter |
| 6,638,528 B1 | 10/2003 | Kanios |
| 6,638,536 B2 | 10/2003 | Savoir et al. |
| 6,645,528 B1 | 11/2003 | Straub et al. |
| 6,649,155 B1 | 11/2003 | Dunlop |
| 6,653,298 B2 | 11/2003 | Potter et al. |
| 6,656,929 B1 | 12/2003 | Agnus et al. |
| 6,660,726 B2 | 12/2003 | Hill et al. |
| 6,663,608 B2 | 12/2003 | Rathbone et al. |
| 6,663,895 B2 | 12/2003 | Savoir et al. |
| 6,664,296 B1 | 12/2003 | Meignant |
| 6,682,757 B1 | 1/2004 | Wright |
| 6,692,763 B1 | 2/2004 | Cummings et al. |
| 6,708,822 B1 | 3/2004 | Muni |
| 6,716,454 B2 | 4/2004 | Meignant |
| 6,720,001 B2 | 4/2004 | Chen |
| 6,737,081 B2 | 5/2004 | Savoir et al. |
| 6,740,333 B2 | 5/2004 | Beckett et al. |
| 6,743,448 B2 | 6/2004 | Kryger |
| 6,743,815 B2 | 6/2004 | Huebner et al. |
| 6,747,018 B2 | 6/2004 | Tanabe et al. |
| 6,750,291 B2 | 6/2004 | Kim |
| 6,756,208 B2 | 6/2004 | Griffin et al. |
| 6,776,164 B2 | 8/2004 | Bunt et al. |
| 6,787,152 B2 | 9/2004 | Kirby et al. |
| 6,805,877 B2 | 10/2004 | Massara et al. |
| 6,809,085 B1 | 10/2004 | Elson et al. |
| 6,818,226 B2 | 11/2004 | Reed et al. |
| 6,821,524 B2 | 11/2004 | Marini |
| 6,841,716 B1 | 1/2005 | Tsutsumi |
| 6,844,334 B2 | 1/2005 | Hill et al. |
| 6,855,703 B1 | 2/2005 | Hill et al. |
| 6,860,859 B2 | 3/2005 | Mehrotra et al. |
| 6,866,865 B2 | 3/2005 | Hsia et al. |
| 6,869,969 B2 | 3/2005 | Heubner et al. |
| 6,878,518 B2 | 4/2005 | Whitehead |
| 6,901,278 B1 | 5/2005 | Notelovitz |
| 6,905,705 B2 | 6/2005 | Palm et al. |
| 6,911,211 B2 | 6/2005 | Tamarkin |
| 6,911,438 B2 | 6/2005 | Wright |
| 6,923,988 B2 | 8/2005 | Patel et al. |
| 6,924,274 B2 | 8/2005 | Lardy et al. |
| 6,932,983 B1 | 8/2005 | Straub et al. |
| 6,939,558 B2 | 9/2005 | Massara et al. |
| 6,943,021 B2 | 9/2005 | Klausner et al. |
| 6,958,327 B1 | 10/2005 | Hillisch et al. |
| 6,960,337 B2 | 11/2005 | Pike |
| 6,962,691 B1 | 11/2005 | Lulla et al. |
| 6,962,908 B2 | 11/2005 | Aloba et al. |
| 6,967,194 B1 | 11/2005 | Matsuo et al. |
| 6,974,569 B2 | 12/2005 | Boyd |
| 6,977,250 B2 | 12/2005 | Rodriguez |
| 6,978,945 B2 | 12/2005 | Wong et al. |
| 6,987,129 B2 | 1/2006 | Mak et al. |
| 6,995,149 B1 | 2/2006 | Reilhac |
| 7,004,321 B1 | 2/2006 | Hackbirth |
| 7,005,429 B2 | 2/2006 | Dey et al. |

(56) References Cited

U.S. PATENT DOCUMENTS

| | | |
|---|---|---|
| 7,011,846 B2 | 3/2006 | Shojaei et al. |
| 7,018,992 B2 | 3/2006 | Koch et al. |
| 7,030,104 B2 | 4/2006 | Paris |
| 7,030,157 B2 | 4/2006 | Ke et al. |
| RE39,104 E | 5/2006 | Duclos et al. |
| 7,074,779 B2 | 7/2006 | Sui et al. |
| 7,083,590 B1 | 8/2006 | Bunt et al. |
| 7,091,213 B2 | 8/2006 | Metcalf, III et al. |
| 7,094,228 B2 | 8/2006 | Zhang |
| 7,097,853 B1 | 8/2006 | Keister |
| 7,101,342 B1 | 9/2006 | Caillouette |
| 7,105,573 B2 | 9/2006 | Krajcik |
| 7,135,190 B2 | 11/2006 | Piao et al. |
| 7,153,522 B1 | 12/2006 | Ikeura |
| 7,163,681 B2 | 1/2007 | Giles-Komar et al. |
| 7,163,699 B2 | 1/2007 | Besse |
| 7,175,850 B2 | 2/2007 | Cevc |
| 7,179,799 B2 | 2/2007 | Hill et al. |
| 7,196,074 B2 | 3/2007 | Blye et al. |
| 7,198,800 B1 | 4/2007 | Ko |
| 7,198,801 B2 | 4/2007 | Carrara et al. |
| 7,226,910 B2 | 6/2007 | Wilson et al. |
| 7,247,625 B2 | 7/2007 | Zhang et al. |
| 7,250,446 B2 | 7/2007 | Sangita et al. |
| 7,267,829 B2 | 9/2007 | Kirby et al. |
| 7,300,926 B2 | 11/2007 | Prokai et al. |
| 7,303,763 B2 | 12/2007 | Ho |
| 7,317,037 B2 | 1/2008 | Fensome et al. |
| 7,329,654 B2 | 2/2008 | Kanojia et al. |
| 7,335,650 B2 | 2/2008 | Potter et al. |
| 7,374,779 B2 | 5/2008 | Chen et al. |
| 7,378,404 B2 | 5/2008 | Peters et al. |
| 7,381,427 B2 | 6/2008 | Ancira |
| 7,387,789 B2 | 6/2008 | Klose et al. |
| 7,388,006 B2 | 6/2008 | Schmees et al. |
| 7,414,043 B2 | 8/2008 | Kosemund et al. |
| 7,427,413 B2 | 9/2008 | Savoir et al. |
| 7,427,609 B2 | 9/2008 | Leonard |
| 7,429,576 B2 | 9/2008 | Labrie |
| 7,431,941 B2 | 10/2008 | Besins et al. |
| 7,456,159 B2 | 11/2008 | Houze |
| 7,459,445 B2 | 12/2008 | Hill et al. |
| 7,465,587 B2 | 12/2008 | Imrich |
| 7,470,433 B2 | 12/2008 | Carrara et al. |
| 7,485,666 B2 | 2/2009 | Villaneuva et al. |
| 7,497,855 B2 | 3/2009 | Ausiello et al. |
| 7,498,303 B2 | 3/2009 | Arnold |
| 7,534,765 B2 | 5/2009 | Gregg et al. |
| 7,534,780 B2 | 5/2009 | Ring |
| 7,550,142 B2 | 6/2009 | Giles-Komar et al. |
| 7,563,565 B1 | 7/2009 | Matsuo et al. |
| 7,569,274 B2 | 8/2009 | Alphonse |
| 7,572,779 B2 | 8/2009 | Aloba et al. |
| 7,572,780 B2 | 8/2009 | Hermsmeyer |
| 7,589,082 B2 | 9/2009 | Savoir et al. |
| 7,671,027 B2 | 3/2010 | Loumaye |
| 7,674,783 B2 | 3/2010 | Hermsmeyer |
| 7,687,281 B2 | 3/2010 | Roth et al. |
| 7,687,485 B2 | 3/2010 | Levinson et al. |
| 7,694,683 B2 | 4/2010 | Callister et al. |
| 7,704,983 B1 | 4/2010 | Hodgen et al. |
| 7,727,720 B2 | 6/2010 | Dhallan |
| 7,732,408 B2 | 6/2010 | Josephson et al. |
| 7,749,989 B2 | 7/2010 | Hill et al. |
| 7,767,656 B2 | 8/2010 | Shoichet et al. |
| 7,799,769 B2 | 9/2010 | White |
| 7,815,936 B2 | 10/2010 | Hasenzahl |
| 7,815,949 B2 | 10/2010 | Cohen |
| 7,829,115 B2 | 11/2010 | Besins et al. |
| 7,829,116 B2 | 11/2010 | Frye |
| RE42,012 E | 12/2010 | Deaver et al. |
| 7,850,992 B2 | 12/2010 | Hwang |
| 7,854,753 B2 | 12/2010 | Kraft |
| 7,858,607 B2 | 12/2010 | Mamchur |
| RE42,072 E | 1/2011 | Deaver et al. |
| 7,862,552 B2 | 1/2011 | McIntyre et al. |
| 7,867,990 B2 | 1/2011 | Schultz et al. |
| 7,871,643 B2 | 1/2011 | Lizio |
| 7,879,830 B2 | 2/2011 | Wiley |
| 7,884,093 B2 | 2/2011 | Creasy et al. |
| 7,925,519 B2 | 4/2011 | Greene |
| 7,939,104 B2 | 5/2011 | Barbera et al. |
| 7,943,602 B2 | 5/2011 | Bunschoten et al. |
| 7,943,604 B2 | 5/2011 | Coelingh Bennink et al. |
| 7,945,459 B2 | 5/2011 | Grace et al. |
| 7,960,368 B2 | 6/2011 | Rao |
| 7,989,436 B2 | 8/2011 | Hill et al. |
| 7,989,487 B2 | 8/2011 | Welsh et al. |
| 8,022,053 B2 | 9/2011 | Mueller et al. |
| 8,048,017 B2 | 11/2011 | Xu |
| 8,048,869 B2 | 11/2011 | Bunschoten et al. |
| 8,063,030 B2 | 11/2011 | Ellman |
| 8,071,576 B2 | 12/2011 | Visser |
| 8,071,729 B2 | 12/2011 | Giles-Komar et al. |
| 8,075,916 B2 | 12/2011 | Park |
| 8,075,917 B2 | 12/2011 | Park |
| 8,076,317 B2 | 12/2011 | Kulmann |
| 8,076,319 B2 | 12/2011 | Leonard |
| 8,080,553 B2 | 12/2011 | Auspitz |
| 8,088,605 B2 | 1/2012 | Beudet et al. |
| 8,096,940 B2 | 1/2012 | Iverson |
| 8,101,209 B2 | 1/2012 | Legrand et al. |
| 8,101,773 B2 | 1/2012 | Smith et al. |
| 8,114,152 B2 | 2/2012 | Furst |
| 8,114,434 B2 | 2/2012 | Sasaki et al. |
| 8,114,442 B2 | 2/2012 | Tucker |
| 8,119,741 B2 | 2/2012 | Pavlin |
| 8,121,886 B2 | 2/2012 | Azar |
| 8,124,118 B2 | 2/2012 | Lennernaes |
| 8,124,595 B2 | 2/2012 | Boissonneault |
| 8,147,561 B2 | 4/2012 | Binmoeller |
| 8,148,546 B2 | 4/2012 | Schuster et al. |
| 8,158,613 B2 | 4/2012 | Staniforth |
| 8,158,614 B2 | 4/2012 | Lambert et al. |
| 8,163,722 B2 | 4/2012 | Savoir |
| 8,177,449 B2 | 5/2012 | Watkinson |
| 8,182,833 B2 | 5/2012 | Hermsmeyer |
| 8,187,615 B2 | 5/2012 | Friedman |
| 8,187,640 B2 | 5/2012 | Dunn |
| 8,195,403 B2 | 6/2012 | Wood, Jr. |
| 8,202,736 B2 | 6/2012 | Mousa et al. |
| 8,217,024 B2 | 7/2012 | Ahmed et al. |
| 8,221,785 B2 | 7/2012 | Chien |
| 8,222,008 B2 | 7/2012 | Thoene |
| 8,222,237 B2 | 7/2012 | Narkunan |
| 8,227,454 B2 | 7/2012 | Hill et al. |
| 8,227,509 B2 | 7/2012 | Castro et al. |
| 8,241,664 B2 | 8/2012 | Dudley et al. |
| 8,247,393 B2 | 8/2012 | Ahmed et al. |
| 8,257,724 B2 | 9/2012 | Cromack |
| 8,257,725 B2 | 9/2012 | Cromack |
| 8,268,352 B2 | 9/2012 | Karan |
| 8,268,806 B2 | 9/2012 | Labrie |
| 8,268,878 B2 | 9/2012 | Johnson |
| 8,273,730 B2 | 9/2012 | Fernandez et al. |
| 8,287,888 B2 | 10/2012 | Song et al. |
| 8,288,366 B2 | 10/2012 | Gonzalez |
| 8,318,898 B2 | 11/2012 | Fasel |
| 8,324,193 B2 | 12/2012 | Lee |
| 8,329,680 B2 | 12/2012 | Evans et al. |
| 8,337,814 B2 | 12/2012 | Osbakken et al. |
| 8,344,007 B2 | 1/2013 | Chui |
| 8,349,820 B2 | 1/2013 | Zeun et al. |
| 8,353,863 B2 | 1/2013 | Imran |
| 8,357,723 B2 | 1/2013 | Satyam |
| 8,361,995 B2 | 1/2013 | Schramm |
| 8,362,091 B2 | 1/2013 | Besonov |
| 8,372,424 B2 | 2/2013 | Berry |
| 8,372,806 B2 | 2/2013 | Bragagna |
| 8,377,482 B2 | 2/2013 | Laurie |
| 8,377,994 B2 | 2/2013 | Drechsler |
| 8,394,759 B2 | 3/2013 | Barathur et al. |
| 8,415,332 B2 | 4/2013 | Reape |
| 8,420,111 B2 | 4/2013 | Hermsmeyer |

(56) References Cited

U.S. PATENT DOCUMENTS

| | | |
|---|---|---|
| 8,435,561 B2 | 5/2013 | Besins et al. |
| 8,435,972 B2 | 5/2013 | Sayeed |
| 8,449,879 B2 | 5/2013 | Laurent Applegate |
| 8,450,108 B2 | 5/2013 | Boyce |
| 8,454,945 B2 | 6/2013 | Narain |
| 8,455,468 B2 | 6/2013 | Kellermann |
| 8,461,138 B2 | 6/2013 | Boissonneault |
| 8,476,252 B2 | 7/2013 | Pickersgill |
| 8,481,488 B2 | 7/2013 | Carter |
| 8,486,374 B2 | 7/2013 | Zlatkis |
| 8,486,442 B2 | 7/2013 | Yamaji |
| 8,492,368 B2 | 7/2013 | Lewandowski |
| 8,507,467 B2 | 8/2013 | Ueda |
| 8,512,693 B2 | 8/2013 | Azevedo |
| 8,512,754 B2 | 8/2013 | Needham |
| 8,518,376 B2 | 8/2013 | Schuz |
| 8,536,159 B2 | 9/2013 | Zeng |
| 8,540,967 B2 | 9/2013 | Trivedi |
| 8,541,400 B2 | 9/2013 | Joabsson |
| 8,551,462 B2 | 10/2013 | Marenus |
| 8,557,281 B2 | 10/2013 | Tuominen |
| 8,568,374 B2 | 10/2013 | De Graaff |
| 8,591,951 B2 | 11/2013 | Kohn |
| 8,613,951 B2 | 12/2013 | Troiano |
| 8,633,178 B2 | 1/2014 | Cacace |
| 8,633,180 B2 | 1/2014 | Zeng |
| 8,636,787 B2 | 1/2014 | Sabaria |
| 8,636,982 B2 | 1/2014 | Schuz |
| 8,653,129 B2 | 2/2014 | Fein |
| 8,658,627 B2 | 2/2014 | Voskuhl |
| 8,658,628 B2 | 2/2014 | Baucom |
| 8,663,681 B2 | 3/2014 | Ahmed et al. |
| 8,663,692 B1 | 3/2014 | Mueller |
| 8,663,703 B2 | 3/2014 | Moldavski |
| 8,664,207 B2 | 3/2014 | Zheng |
| 8,669,293 B2 | 3/2014 | Sharoni |
| 8,679,552 B2 | 3/2014 | Guthery |
| 8,694,358 B2 | 4/2014 | Tryfon |
| 8,697,127 B2 | 4/2014 | Sah |
| 8,697,710 B2 | 4/2014 | Zeng |
| 8,703,105 B2 | 4/2014 | Besonov |
| 8,709,385 B2 | 4/2014 | Schuz |
| 8,709,451 B2 | 4/2014 | Rapoport |
| 8,715,735 B2 | 5/2014 | Funke |
| 8,721,331 B2 | 5/2014 | Raghuprasad |
| 8,722,021 B2 | 5/2014 | Eini |
| 8,734,846 B2 | 5/2014 | Hrkach |
| 8,735,381 B2 | 5/2014 | Podolski |
| 8,741,336 B2 | 6/2014 | Dipierro |
| 8,741,373 B2 | 6/2014 | Rao |
| 8,753,661 B2 | 6/2014 | Gassner |
| 8,784,882 B2 | 7/2014 | Mattern |
| 8,846,648 B2 | 9/2014 | Bernick et al. |
| 8,846,649 B2 | 9/2014 | Bernick et al. |
| 8,933,059 B2 | 1/2015 | Bernick et al. |
| 8,987,237 B2 | 3/2015 | Bernick et al. |
| 8,987,238 B2 | 3/2015 | Bernick et al. |
| 8,993,548 B2 | 3/2015 | Bernick et al. |
| 8,993,549 B2 | 3/2015 | Bernick et al. |
| 9,006,222 B2 | 4/2015 | Bernick et al. |
| 9,012,434 B2 | 4/2015 | Bernick et al. |
| 9,114,145 B2 | 8/2015 | Bernick et al. |
| 9,114,146 B2 | 8/2015 | Bernick et al. |
| 9,180,091 B2 | 11/2015 | Bernick et al. |
| 9,248,136 B2 | 2/2016 | Bernick et al. |
| 9,289,382 B2 | 3/2016 | Bernick et al. |
| 9,301,920 B2 | 4/2016 | Bernick et al. |
| 9,931,349 B2 | 4/2018 | Shadiack et al. |
| 10,052,386 B2 | 8/2018 | Bernick et al. |
| 10,206,932 B2 | 2/2019 | Bernick et al. |
| 10,258,630 B2 | 4/2019 | Mirkin et al. |
| 2001/0005728 A1 | 2/2001 | Guittard et al. |
| 2001/0009673 A1 | 7/2001 | Gunther |
| 2001/0021816 A1 | 9/2001 | Caillouette |
| 2001/0023261 A1 | 9/2001 | Ryoo |
| 2001/0027189 A1 | 10/2001 | Bennink et al. |
| 2001/0029357 A1 | 10/2001 | Bunt et al. |
| 2001/0031747 A1 | 10/2001 | de Ziegler et al. |
| 2001/0032125 A1 | 10/2001 | Bhan et al. |
| 2001/0034340 A1 | 10/2001 | Pickar |
| 2012/0269878 A2 | 10/2001 | Cantor et al. |
| 2001/0053383 A1 | 12/2001 | Sablotsky |
| 2001/0056068 A1 | 12/2001 | Chwalisz et al. |
| 2002/0012710 A1 | 1/2002 | Lansky |
| 2002/0026158 A1 | 2/2002 | Rathbone et al. |
| 2002/0028788 A1 | 3/2002 | Bunt et al. |
| 2002/0035070 A1 | 3/2002 | Gardlik |
| 2002/0058648 A1 | 5/2002 | Hammerly |
| 2002/0058926 A1 | 5/2002 | Rathbone et al. |
| 2002/0064541 A1 | 5/2002 | Lapidot et al. |
| 2002/0076441 A1 | 6/2002 | Shih et al. |
| 2002/0102308 A1 | 8/2002 | Wei et al. |
| 2002/0107230 A1 | 8/2002 | Waldon et al. |
| 2002/0114803 A1 | 8/2002 | Deaver et al. |
| 2002/0119174 A1 | 8/2002 | Gardlik |
| 2002/0119198 A1 | 8/2002 | Gao |
| 2002/0132801 A1 | 9/2002 | Heil et al. |
| 2002/0137749 A1 | 9/2002 | Levinson et al. |
| 2002/0142017 A1 | 10/2002 | Simonnet |
| 2002/0151530 A1 | 10/2002 | Leonard et al. |
| 2002/0156394 A1 | 10/2002 | Mehrotra et al. |
| 2002/0169150 A1 | 11/2002 | Pickar |
| 2002/0169205 A1 | 11/2002 | Garfield |
| 2002/0173510 A1 | 11/2002 | Levinson et al. |
| 2002/0193356 A1 | 12/2002 | Van Beek et al. |
| 2002/0193758 A1 | 12/2002 | Sandberg |
| 2002/0197286 A1 | 12/2002 | Brandman |
| 2003/0003139 A1 | 1/2003 | Gunther |
| 2003/0004145 A1 | 1/2003 | Leonard |
| 2003/0007994 A1 | 1/2003 | Bunt et al. |
| 2003/0027772 A1 | 2/2003 | Breton |
| 2003/0091620 A1 | 2/2003 | Venkateshwaran |
| 2003/0044453 A1 | 3/2003 | Volkel |
| 2003/0049307 A1 | 3/2003 | Gyurik |
| 2003/0064097 A1 | 4/2003 | Patel et al. |
| 2003/0064975 A1 | 4/2003 | Koch et al. |
| 2003/0072760 A1 | 4/2003 | Sirbasku |
| 2003/0073248 A1 | 4/2003 | Roth et al. |
| 2003/0073673 A1 | 4/2003 | Hesch |
| 2003/0077297 A1 | 4/2003 | Chen et al. |
| 2003/0078245 A1 | 4/2003 | Bennink et al. |
| 2003/0091640 A1 | 5/2003 | Ramanathan et al. |
| 2003/0092691 A1 | 5/2003 | Besse et al. |
| 2003/0096012 A1 | 5/2003 | Besse et al. |
| 2003/0104048 A1 | 6/2003 | Patel et al. |
| 2003/0109507 A1 | 6/2003 | Beckmann |
| 2003/0113268 A1 | 6/2003 | Buenafae |
| 2003/0114420 A1 | 6/2003 | Salvati et al. |
| 2003/0114430 A1 | 6/2003 | MacLeod et al. |
| 2003/0124182 A1 | 7/2003 | Shojaei et al. |
| 2003/0124191 A1 | 7/2003 | Besse et al. |
| 2003/0130558 A1 | 7/2003 | Massara et al. |
| 2003/0144258 A1 | 7/2003 | Heil et al. |
| 2003/0157157 A1 | 8/2003 | Luo et al. |
| 2003/0166509 A1 | 9/2003 | Batycky et al. |
| 2003/0170295 A1 | 9/2003 | Yoon |
| 2003/0175329 A1 | 9/2003 | Mak |
| 2003/0175333 A1 | 9/2003 | Shefer |
| 2003/0180352 A1 | 9/2003 | Patel et al. |
| 2003/0181353 A1 | 9/2003 | Nyce |
| 2003/0181728 A1 | 9/2003 | Salvati et al. |
| 2003/0191096 A1 | 10/2003 | Leonard et al. |
| 2003/0195177 A1 | 10/2003 | Leonard et al. |
| 2003/0215496 A1 | 11/2003 | Patel et al. |
| 2003/0219402 A1 | 11/2003 | Rutter |
| 2003/0220297 A1 | 11/2003 | Bernstein et al. |
| 2003/0224057 A1 | 12/2003 | Martin-Letellier et al. |
| 2003/0224059 A1 | 12/2003 | Lerner et al. |
| 2003/0225047 A1 | 12/2003 | Friedman |
| 2003/0225048 A1 | 12/2003 | Friedman |
| 2003/0225050 A1 | 12/2003 | Eichardt et al. |
| 2003/0228686 A1 | 12/2003 | Klausner et al. |
| 2003/0229057 A1 | 12/2003 | Caubel et al. |
| 2003/0235596 A1 | 12/2003 | Gao |

(56) References Cited

U.S. PATENT DOCUMENTS

| | | |
|---|---|---|
| 2003/0236236 A1 | 12/2003 | Chen et al. |
| 2004/0009960 A1 | 1/2004 | Heil et al. |
| 2004/0022820 A1 | 2/2004 | Anderson |
| 2004/0034001 A1 | 2/2004 | Karara |
| 2004/0037881 A1 | 2/2004 | Guittard et al. |
| 2004/0039356 A1 | 2/2004 | Maki |
| 2004/0043043 A1 | 3/2004 | Schlyter |
| 2004/0043943 A1 | 3/2004 | Guittard et al. |
| 2004/0044080 A1 | 3/2004 | Place et al. |
| 2004/0048900 A1 | 3/2004 | Flood |
| 2004/0052824 A1 | 3/2004 | Abou Chacra-Vernet et al. |
| 2004/0073024 A1 | 4/2004 | Metcalf, III et al. |
| 2004/0077605 A1 | 4/2004 | Salvati et al. |
| 2004/0077606 A1 | 4/2004 | Salvati et al. |
| 2004/0087548 A1 | 5/2004 | Salvati et al. |
| 2004/0087564 A1 | 5/2004 | Wright |
| 2004/0089308 A1 | 5/2004 | Welch |
| 2004/0092494 A9 | 5/2004 | Dudley |
| 2004/0092583 A1 | 5/2004 | Shanahan-Prendergast |
| 2004/0093261 A1 | 5/2004 | Jain et al. |
| 2004/0097468 A1 | 5/2004 | Wimalawansa |
| 2004/0101557 A1 | 5/2004 | Gibson et al. |
| 2004/0106542 A1 | 6/2004 | Deaver et al. |
| 2004/0110732 A1 | 6/2004 | Masini Eteve |
| 2004/0131670 A1 | 7/2004 | Gao |
| 2004/0138103 A1 | 7/2004 | Patt |
| 2004/0142012 A1 | 7/2004 | Bunt et al. |
| 2004/0146539 A1 | 7/2004 | Gupta |
| 2004/0146894 A1 | 7/2004 | Warrington et al. |
| 2004/0147578 A1 | 7/2004 | Calvet |
| 2004/0161435 A1 | 8/2004 | Gupta |
| 2004/0176324 A1 | 9/2004 | Salvati et al. |
| 2004/0176336 A1 | 9/2004 | Rodriguez |
| 2004/0185104 A1 | 9/2004 | Piao et al. |
| 2004/0191207 A1 | 9/2004 | Lipari |
| 2004/0191276 A1 | 9/2004 | Muni |
| 2004/0198706 A1 | 10/2004 | Carrara et al. |
| 2004/0210280 A1 | 10/2004 | Liedtke |
| 2004/0213744 A1 | 10/2004 | Lulla et al. |
| 2004/0219124 A1 | 11/2004 | Gupta |
| 2004/0225140 A1 | 11/2004 | Sciano |
| 2004/0234606 A1 | 11/2004 | Levine et al. |
| 2004/0241219 A1 | 12/2004 | Hille |
| 2004/0243437 A1 | 12/2004 | Grace et al. |
| 2004/0253319 A1 | 12/2004 | Netke et al. |
| 2004/0259817 A1 | 12/2004 | Waldon et al. |
| 2004/0266745 A1 | 12/2004 | Schwanitz et al. |
| 2005/0003003 A1 | 1/2005 | Deaver |
| 2005/0004088 A1 | 1/2005 | Hesch |
| 2005/0009800 A1 | 1/2005 | Thumbeck et al. |
| 2005/0014729 A1 | 1/2005 | Pulaski |
| 2005/0020550 A1 | 1/2005 | Latif |
| 2005/0020552 A1 | 1/2005 | Aschkenasay et al. |
| 2005/0021009 A1 | 1/2005 | Massara et al. |
| 2005/0025833 A1 | 2/2005 | Aschkenasay et al. |
| 2005/0031651 A1 | 2/2005 | Gervais et al. |
| 2005/0042173 A1 | 2/2005 | Besse et al. |
| 2005/0042268 A1 | 2/2005 | Aschkenasay et al. |
| 2005/0048116 A1 | 3/2005 | Straub et al. |
| 2005/0054991 A1 | 3/2005 | Paterson |
| 2005/0079138 A1 | 4/2005 | Chickering, III et al. |
| 2005/0085453 A1 | 4/2005 | Govindarajan |
| 2005/0101579 A1 | 5/2005 | Shippen |
| 2005/0113350 A1 | 5/2005 | Duesterberg et al. |
| 2005/0118244 A1 | 6/2005 | Theobald et al. |
| 2005/0118272 A1 | 6/2005 | Besse et al. |
| 2005/0129756 A1 | 6/2005 | Podhaisky |
| 2005/0152956 A1 | 7/2005 | Dudley |
| 2005/0153946 A1 | 7/2005 | Hirsh et al. |
| 2005/0164977 A1 | 7/2005 | Coelingh Bennink |
| 2005/0182105 A1 | 8/2005 | Nirschl et al. |
| 2005/0186141 A1 | 8/2005 | Gonda |
| 2005/0187267 A1 | 8/2005 | Hamann et al. |
| 2005/0192253 A1 | 9/2005 | Salvati et al. |
| 2005/0192310 A1 | 9/2005 | Gavai et al. |
| 2005/0196434 A1 | 9/2005 | Brierre |
| 2005/0207990 A1 | 9/2005 | Funke et al. |
| 2005/0209209 A1 | 9/2005 | Koch et al. |
| 2005/0214384 A1 | 9/2005 | Juturu et al. |
| 2005/0220825 A1 | 10/2005 | Funke et al. |
| 2005/0220900 A1 | 10/2005 | Wuttke |
| 2005/0222106 A1 | 10/2005 | Bracht |
| 2005/0228692 A1 | 10/2005 | Hodgdon |
| 2005/0228718 A1 | 10/2005 | Austin |
| 2005/0239747 A1 | 10/2005 | Le |
| 2005/0239758 A1 | 10/2005 | Roby |
| 2005/0244360 A1 | 11/2005 | Billoni |
| 2005/0244522 A1 | 11/2005 | Carrara et al. |
| 2005/0245902 A1 | 11/2005 | Cornish et al. |
| 2005/0250746 A1 | 11/2005 | Iammatteo |
| 2005/0250750 A1 | 11/2005 | Cummings et al. |
| 2005/0250753 A1 | 11/2005 | Fink et al. |
| 2005/0256028 A1 | 11/2005 | Yun et al. |
| 2005/0266078 A1 | 11/2005 | Jorda et al. |
| 2005/0266088 A1 | 12/2005 | Frijlink |
| 2005/0271597 A1 | 12/2005 | Keith |
| 2005/0271598 A1 | 12/2005 | Friedman et al. |
| 2005/0272685 A1 | 12/2005 | Hung |
| 2005/0272712 A1 | 12/2005 | Grubb et al. |
| 2006/0009428 A1 | 1/2006 | Grubb et al. |
| 2006/0014728 A1 | 1/2006 | Chwalisz et al. |
| 2006/0018937 A1 | 1/2006 | Friedman et al. |
| 2006/0019978 A1 | 1/2006 | Balog |
| 2006/0020002 A1 | 1/2006 | Salvati et al. |
| 2006/0030615 A1 | 2/2006 | Fensome et al. |
| 2006/0034889 A1 | 2/2006 | Jo et al. |
| 2006/0034904 A1 | 2/2006 | Weimann |
| 2006/0040904 A1 | 2/2006 | Ahmed et al. |
| 2006/0051391 A1 | 3/2006 | Dvoskin et al. |
| 2006/0052341 A1 | 3/2006 | Cornish et al. |
| 2006/0069031 A1 | 3/2006 | Loumaye |
| 2006/0078618 A1 | 4/2006 | Constantinides |
| 2006/0083778 A1 | 4/2006 | Allison et al. |
| 2006/0084704 A1 | 4/2006 | Shin |
| 2006/0088580 A1 | 4/2006 | Seibertz |
| 2006/0089337 A1 | 4/2006 | Casper et al. |
| 2006/0093678 A1 | 5/2006 | Chickering, III et al. |
| 2006/0100180 A1 | 5/2006 | Bohlmann |
| 2006/0106004 A1 | 5/2006 | Brody et al. |
| 2006/0110415 A1 | 5/2006 | Gupta |
| 2006/0111424 A1 | 5/2006 | Salvati et al. |
| 2006/0121102 A1 | 6/2006 | Chiang |
| 2006/0121626 A1 | 6/2006 | Imrich |
| 2006/0134188 A1 | 6/2006 | Podhaisky et al. |
| 2006/0135619 A1 | 6/2006 | Kick et al. |
| 2006/0165744 A1 | 7/2006 | Anyarambhatla |
| 2006/0193789 A1 | 8/2006 | Tamarkin |
| 2006/0194775 A1 | 8/2006 | Tofovic et al. |
| 2006/0204557 A1 | 9/2006 | Gupta et al. |
| 2006/0233743 A1 | 10/2006 | Kelly |
| 2006/0233841 A1 | 10/2006 | Pushpala |
| 2006/0235037 A1 | 10/2006 | Purandare et al. |
| 2006/0240111 A1 | 10/2006 | Fernandez et al. |
| 2006/0246122 A1 | 11/2006 | Langguth |
| 2006/0247216 A1 | 11/2006 | Haj-Yehia |
| 2006/0247221 A1 | 11/2006 | Coelingh Bennink |
| 2006/0251581 A1 | 11/2006 | Madenjian |
| 2006/0252049 A1 | 11/2006 | Shuler et al. |
| 2006/0257472 A1 | 11/2006 | Neilsen |
| 2006/0275218 A1 | 12/2006 | Besonov |
| 2006/0275360 A1 | 12/2006 | Ahmed et al. |
| 2006/0276414 A1 | 12/2006 | Coelingh Bennink |
| 2006/0280771 A1 | 12/2006 | Groenewegen et al. |
| 2006/0280797 A1 | 12/2006 | Shoichet et al. |
| 2006/0280800 A1 | 12/2006 | Nagi et al. |
| 2006/0292223 A1 | 12/2006 | Mc Ilroy |
| 2007/0004693 A1 | 1/2007 | Woolfson et al. |
| 2007/0004694 A1 | 1/2007 | Woolfson et al. |
| 2007/0009559 A1 | 1/2007 | Alosio |
| 2007/0009594 A1 | 1/2007 | Grubb et al. |
| 2007/0010550 A1 | 1/2007 | McKenzie |
| 2007/0014839 A1 | 1/2007 | Bracht |
| 2007/0015698 A1 | 1/2007 | Goldstein |
| 2007/0021360 A1 | 1/2007 | Nyce et al. |

(56) References Cited

U.S. PATENT DOCUMENTS

| | | |
|---|---|---|
| 2007/0027201 A1 | 2/2007 | McComas et al. |
| 2007/0031491 A1 | 2/2007 | Levine et al. |
| 2007/0036843 A1 | 2/2007 | Hirsh et al. |
| 2007/0037780 A1 | 2/2007 | Anigbogu |
| 2007/0037782 A1 | 2/2007 | Suzuki |
| 2007/0042038 A1 | 2/2007 | Besse |
| 2007/0060589 A1 | 3/2007 | Purandare et al. |
| 2007/0066628 A1 | 3/2007 | Zhang et al. |
| 2007/0066637 A1 | 3/2007 | Zhang et al. |
| 2007/0066675 A1 | 3/2007 | Zhang et al. |
| 2007/0071777 A1 | 3/2007 | Bromer et al. |
| 2007/0078091 A1 | 4/2007 | Hubler |
| 2007/0088029 A1 | 4/2007 | Balog et al. |
| 2007/0093548 A1 | 4/2007 | Diffendal et al. |
| 2007/0116729 A1 | 5/2007 | Palepu |
| 2007/0116829 A1 | 5/2007 | Prakash et al. |
| 2007/0128263 A1 | 6/2007 | Wall |
| 2007/0154533 A1 | 7/2007 | Dudley |
| 2007/0167418 A1 | 7/2007 | Ferguson |
| 2007/0178166 A1 | 8/2007 | Bernstein et al. |
| 2007/0184558 A1 | 8/2007 | Roth et al. |
| 2007/0185068 A1 | 8/2007 | Ferguson |
| 2007/0190022 A1 | 8/2007 | Chiao |
| 2007/0191319 A1 | 8/2007 | Ke et al. |
| 2007/0191321 A1 | 8/2007 | Ahmed et al. |
| 2007/0196415 A1 | 8/2007 | Houston |
| 2007/0196433 A1 | 8/2007 | Ron et al. |
| 2007/0207225 A1 | 9/2007 | Squadrito |
| 2007/0225281 A1 | 9/2007 | Zhang et al. |
| 2007/0232574 A1 | 10/2007 | Bernard |
| 2007/0238713 A1 | 10/2007 | Gast et al. |
| 2007/0243229 A1 | 10/2007 | Smith et al. |
| 2007/0248658 A1 | 10/2007 | Bracht |
| 2007/0254858 A1 | 11/2007 | Cronk |
| 2007/0255197 A1 | 11/2007 | Wilkins |
| 2007/0264309 A1 | 11/2007 | Chollet et al. |
| 2007/0264345 A1 | 11/2007 | Eros et al. |
| 2007/0264349 A1 | 11/2007 | Lee et al. |
| 2007/0270394 A1 | 11/2007 | El-Alfy et al. |
| 2007/0286819 A1 | 12/2007 | DeVries et al. |
| 2007/0287688 A1 | 12/2007 | Chan |
| 2007/0287789 A1 | 12/2007 | Jones et al. |
| 2007/0292359 A1 | 12/2007 | Schuz |
| 2007/0292387 A1 | 12/2007 | Jon et al. |
| 2007/0292461 A1 | 12/2007 | Danziger |
| 2007/0292493 A1 | 12/2007 | Brierre |
| 2007/0298089 A1 | 12/2007 | Yoshinaga |
| 2008/0026035 A1 | 1/2008 | Chollet et al. |
| 2008/0026040 A1 | 1/2008 | Rivera Guzman |
| 2008/0026062 A1 | 1/2008 | Farr et al. |
| 2008/0038219 A1 | 2/2008 | Carlson |
| 2008/0038350 A1 | 2/2008 | Gerecke et al. |
| 2008/0039405 A1 | 2/2008 | Joseph |
| 2008/0050317 A1 | 2/2008 | Besonov |
| 2008/0051351 A1 | 2/2008 | Ghisalberti |
| 2008/0063607 A1 | 3/2008 | Berman |
| 2008/0069779 A1 | 3/2008 | Schuz |
| 2008/0069791 A1 | 3/2008 | Beissert |
| 2008/0085877 A1 | 4/2008 | Bortz |
| 2008/0095831 A1 | 4/2008 | Mc Graw |
| 2008/0095838 A1 | 4/2008 | Abou Chacra-Vernet |
| 2008/0119537 A1 | 5/2008 | Zhang et al. |
| 2008/0125402 A1 | 5/2008 | Dilberti |
| 2008/0138379 A1 | 6/2008 | Jennings-Spring |
| 2008/0138390 A1 | 6/2008 | Gricenko |
| 2008/0139392 A1 | 6/2008 | Yuan |
| 2008/0145423 A1 | 6/2008 | Khan et al. |
| 2008/0153789 A1 | 6/2008 | Dmowski |
| 2008/0175814 A1 | 7/2008 | Phiasivongsa et al. |
| 2008/0175905 A1 | 7/2008 | Liu et al. |
| 2008/0175908 A1 | 7/2008 | Liu et al. |
| 2008/0188829 A1 | 8/2008 | Creasy |
| 2008/0206156 A1 | 8/2008 | Cronk |
| 2008/0206159 A1 | 8/2008 | Schuz |
| 2008/0206161 A1 | 8/2008 | Tamarkin et al. |
| 2008/0214512 A1 | 9/2008 | Seitz |
| 2008/0220069 A1 | 9/2008 | Allison |
| 2008/0226698 A1 | 9/2008 | Beste |
| 2008/0227763 A1 | 9/2008 | Paris |
| 2008/0234199 A1 | 9/2008 | Katamreddy |
| 2008/0234240 A1 | 9/2008 | Duesterberg |
| 2008/0255078 A1 | 10/2008 | Katamreddy |
| 2008/0255089 A1 | 10/2008 | Katamreddy |
| 2008/0261931 A1 | 10/2008 | Stenlof |
| 2008/0113953 A1 | 12/2008 | DeVries et al. |
| 2008/0114050 A1 | 12/2008 | Fensome et al. |
| 2008/0299220 A1 | 12/2008 | Tamarkin et al. |
| 2008/0306036 A1 | 12/2008 | Katamreddy |
| 2008/0312197 A1 | 12/2008 | Rodriguez |
| 2008/0312198 A1 | 12/2008 | Rodriguez |
| 2008/0319078 A1 | 12/2008 | Katamreddy |
| 2009/0004246 A1 | 1/2009 | Woolfson |
| 2009/0010968 A1 | 1/2009 | Peyrot |
| 2009/0011041 A1 | 1/2009 | Musaeva |
| 2009/0017120 A1 | 1/2009 | Brisco |
| 2009/0022683 A1 | 1/2009 | Park |
| 2009/0047357 A1 | 2/2009 | Tomohira |
| 2009/0053294 A1 | 2/2009 | Prendergast |
| 2009/0060982 A1 | 3/2009 | Ron et al. |
| 2009/0060997 A1 | 3/2009 | Seitz |
| 2009/0068118 A1 | 3/2009 | Eini et al. |
| 2009/0074859 A1 | 3/2009 | Patel |
| 2009/0081206 A1 | 3/2009 | Leibovitz |
| 2009/0081278 A1 | 3/2009 | De Graaff et al. |
| 2009/0081303 A1 | 3/2009 | Savoir et al. |
| 2009/0092656 A1 | 4/2009 | Klamerus et al. |
| 2009/0093440 A1 | 4/2009 | Murad |
| 2009/0098069 A1 | 4/2009 | Vacca |
| 2009/0099106 A1 | 4/2009 | Phiasivongsa et al. |
| 2009/0099149 A1 | 4/2009 | Kresevic |
| 2009/0130029 A1 | 5/2009 | Tamarkin |
| 2009/0131385 A1 | 5/2009 | Voskuhl |
| 2009/0136574 A1 | 5/2009 | Diaz-Astruc et al. |
| 2009/0137478 A1 | 5/2009 | Bernstein et al. |
| 2009/0137538 A1 | 5/2009 | Klamerus et al. |
| 2009/0143344 A1 | 6/2009 | Chang |
| 2009/0164341 A1 | 6/2009 | Sunvold et al. |
| 2009/0175799 A1 | 7/2009 | Tamarkin |
| 2009/0181088 A1 | 7/2009 | Song et al. |
| 2009/0186081 A1 | 7/2009 | Slot |
| 2009/0197843 A1 | 8/2009 | Notelovitz |
| 2009/0203658 A1 | 8/2009 | Rose |
| 2009/0214474 A1 | 8/2009 | Jennings |
| 2009/0227025 A1 | 9/2009 | Nichols et al. |
| 2009/0227550 A1 | 9/2009 | Mattern |
| 2009/0232897 A1 | 9/2009 | Sahoo et al. |
| 2009/0258096 A1 | 10/2009 | Cohen |
| 2009/0264395 A1 | 10/2009 | Creasy |
| 2009/0264413 A1 | 10/2009 | Lee et al. |
| 2009/0269403 A1 | 10/2009 | Shaked et al. |
| 2009/0285772 A1 | 11/2009 | Phiasivongsa et al. |
| 2009/0285869 A1 | 11/2009 | Trimble |
| 2009/0318558 A1 | 12/2009 | Kim et al. |
| 2009/0324714 A1 | 12/2009 | Kresevic |
| 2009/0325916 A1 | 12/2009 | Zhang et al. |
| 2010/0008985 A1 | 1/2010 | Vermeulen |
| 2010/0028360 A1 | 2/2010 | Atwood |
| 2010/0034838 A1 | 2/2010 | Staniforth |
| 2010/0034880 A1 | 2/2010 | Sintov |
| 2010/0040671 A1 | 2/2010 | Ahmed et al. |
| 2010/0048523 A1 | 2/2010 | Bachman et al. |
| 2010/0055138 A1 | 3/2010 | Jacobs |
| 2010/0074959 A1 | 3/2010 | Hansom et al. |
| 2010/0086501 A1 | 4/2010 | Chang |
| 2010/0086599 A1 | 4/2010 | Huempel et al. |
| 2010/0092568 A1 | 4/2010 | Lerner et al. |
| 2010/0105071 A1 | 4/2010 | Laufer et al. |
| 2010/0119585 A1 | 5/2010 | Hille et al. |
| 2010/0129320 A1 | 5/2010 | Phiasivongsa et al. |
| 2010/0136105 A1 | 6/2010 | Chen et al. |
| 2010/0137265 A1 | 6/2010 | Leonard |
| 2010/0137271 A1 | 6/2010 | Chen et al. |
| 2010/0143420 A1 | 6/2010 | Lee |
| 2010/0143481 A1 | 6/2010 | Shenoy |

(56) References Cited

U.S. PATENT DOCUMENTS

| | | |
|---|---|---|
| 2010/0150993 A1 | 6/2010 | Theobald et al. |
| 2010/0152144 A1 | 6/2010 | Hermsmeyer |
| 2010/0168228 A1 | 7/2010 | Bose et al. |
| 2010/0183723 A1 | 7/2010 | Laurent-Applegate et al. |
| 2010/0184736 A1 | 7/2010 | Coelingh Bennink et al. |
| 2010/0190758 A1 | 7/2010 | Fauser et al. |
| 2010/0204326 A1 | 8/2010 | D Souza |
| 2010/0210994 A1 | 8/2010 | Zarif |
| 2010/0221195 A1 | 9/2010 | Ziv |
| 2010/0227797 A1 | 9/2010 | Danielsson |
| 2010/0240626 A1 | 9/2010 | Kulkarni et al. |
| 2010/0247482 A1 | 9/2010 | Chen |
| 2010/0247632 A1 | 9/2010 | Dong et al. |
| 2010/0247635 A1 | 9/2010 | Schmidt |
| 2010/0255085 A1 | 10/2010 | Liu et al. |
| 2010/0273730 A1 | 10/2010 | Hsu |
| 2010/0278759 A1 | 11/2010 | Murad |
| 2010/0279988 A1 | 11/2010 | Setiawan |
| 2010/0291191 A1 | 11/2010 | Lapitsky |
| 2010/0292199 A1 | 11/2010 | Leverd |
| 2010/0303825 A9 | 12/2010 | Sirbasku |
| 2010/0312137 A1 | 12/2010 | Gilmour et al. |
| 2010/0316724 A1 | 12/2010 | Whitfield et al. |
| 2010/0322884 A1 | 12/2010 | Wilkins |
| 2010/0330168 A1 | 12/2010 | Gicquel et al. |
| 2011/0028439 A1 | 2/2011 | Witt-Enderby et al. |
| 2011/0039814 A1 | 2/2011 | Ross |
| 2011/0053845 A1 | 3/2011 | Levine et al. |
| 2011/0066473 A1 | 3/2011 | Bernick et al. |
| 2011/0076775 A1 | 3/2011 | Stewart et al. |
| 2011/0076776 A1 | 3/2011 | Stewart et al. |
| 2011/0086825 A1 | 4/2011 | Chatroux |
| 2011/0087192 A1 | 4/2011 | Uhland |
| 2011/0091555 A1 | 4/2011 | De Luigi Bruschi et al. |
| 2011/0098258 A1 | 4/2011 | Canet |
| 2011/0098631 A1 | 4/2011 | McIntyre et al. |
| 2011/0104268 A1 | 5/2011 | Segot Chicq |
| 2011/0104289 A1 | 5/2011 | Savoir Vilboeuf et al. |
| 2011/0130372 A1 | 6/2011 | Marliani |
| 2011/0135719 A1 | 6/2011 | Besins et al. |
| 2011/0142945 A1 | 6/2011 | Chen |
| 2011/0152840 A1 | 6/2011 | Lee |
| 2011/0158920 A1 | 6/2011 | Fisher |
| 2011/0171140 A1 | 7/2011 | Illum |
| 2011/0182997 A1 | 7/2011 | Lewis et al. |
| 2011/0190201 A1 | 8/2011 | Wood, Jr. |
| 2011/0195031 A1 | 8/2011 | Du |
| 2011/0195114 A1 | 8/2011 | Carrara et al. |
| 2011/0195944 A1 | 8/2011 | Mura et al. |
| 2011/0217341 A1 | 9/2011 | Sah |
| 2011/0238003 A1 | 9/2011 | Karabelas |
| 2011/0244043 A1 | 10/2011 | Wang |
| 2011/0250256 A1 | 10/2011 | Hyun |
| 2011/0250259 A1 | 10/2011 | Buckman |
| 2011/0250274 A1 | 10/2011 | Shaked et al. |
| 2011/0256092 A1 | 10/2011 | Phiasivongsa et al. |
| 2011/0262373 A1 | 10/2011 | Umbert Millet |
| 2011/0262494 A1 | 10/2011 | Achleitner et al. |
| 2011/0268665 A1 | 11/2011 | Tamarkin et al. |
| 2011/0275584 A1 | 11/2011 | Volkmann |
| 2011/0281832 A1 | 11/2011 | Wennogle |
| 2011/0287094 A1 | 11/2011 | Penhasi |
| 2011/0293720 A1 | 12/2011 | General et al. |
| 2011/0294738 A1 | 12/2011 | Kuliopulos |
| 2011/0300167 A1 | 12/2011 | Covic |
| 2011/0301087 A1 | 12/2011 | McBride |
| 2011/0306579 A1 | 12/2011 | Stein |
| 2011/0311592 A1 | 12/2011 | Birbara |
| 2011/0312927 A1 | 12/2011 | Nachaegari et al. |
| 2011/0312928 A1 | 12/2011 | Nachaegari et al. |
| 2011/0318405 A1 | 12/2011 | Erwin |
| 2011/0318431 A1 | 12/2011 | Gulati |
| 2012/0009276 A1 | 1/2012 | De Groote |
| 2012/0015350 A1 | 1/2012 | Nabatiyan et al. |
| 2012/0021041 A1 | 1/2012 | Rossi |
| 2012/0028888 A1 | 2/2012 | Janz |
| 2012/0028910 A1 | 2/2012 | Takruri |
| 2012/0028936 A1 | 2/2012 | Popova |
| 2012/0045532 A1 | 2/2012 | Cohen |
| 2012/0046264 A1 | 2/2012 | Lieb |
| 2012/0046518 A1 | 2/2012 | Yoakum |
| 2012/0052077 A1 | 3/2012 | Truitt, III et al. |
| 2012/0058171 A1 | 3/2012 | Zeeman |
| 2012/0058962 A1 | 3/2012 | Sparrow |
| 2012/0058979 A1 | 3/2012 | Auspitz |
| 2012/0064135 A1 | 3/2012 | Harms |
| 2012/0065179 A1 | 3/2012 | Andersson |
| 2012/0065221 A1 | 3/2012 | Babul |
| 2012/0087872 A1 | 4/2012 | Schuz |
| 2012/0101073 A1 | 4/2012 | Mannion |
| 2012/0121517 A1 | 5/2012 | Kim |
| 2012/0121692 A1 | 5/2012 | Fang |
| 2012/0122829 A1 | 5/2012 | Masini Eteve |
| 2012/0128625 A1 | 5/2012 | Shalwitz et al. |
| 2012/0128654 A1 | 5/2012 | Terpstra |
| 2012/0128683 A1 | 5/2012 | Shantha |
| 2012/0128733 A1 | 5/2012 | Perrin |
| 2012/0128777 A1 | 5/2012 | Keck et al. |
| 2012/0129773 A1 | 5/2012 | Geier |
| 2012/0129819 A1 | 5/2012 | Vancaillie |
| 2012/0136013 A1 | 5/2012 | Wennogle |
| 2012/0142645 A1 | 6/2012 | Marx |
| 2012/0148670 A1 | 6/2012 | Lee |
| 2012/0149748 A1 | 6/2012 | Shanler et al. |
| 2012/0172343 A1 | 7/2012 | Schuermann |
| 2012/0184515 A1 | 7/2012 | Schwede |
| 2012/0231052 A1 | 9/2012 | Brinton |
| 2012/0232011 A1 | 9/2012 | Kneissel |
| 2012/0232042 A1 | 9/2012 | Krenz |
| 2012/0263679 A1 | 10/2012 | Wallace |
| 2012/0269721 A1 | 10/2012 | Weng et al. |
| 2012/0277249 A1 | 11/2012 | Tarrand |
| 2012/0277727 A1 | 11/2012 | Doshi |
| 2012/0283671 A1 | 11/2012 | Shibata et al. |
| 2012/0295911 A1 | 11/2012 | Mannion |
| 2012/0301517 A1 | 11/2012 | Warner |
| 2012/0301538 A1 | 11/2012 | Latere |
| 2012/0302535 A1 | 11/2012 | Caufriez |
| 2012/0316130 A1 | 12/2012 | Hendrix |
| 2012/0316496 A1 | 12/2012 | Horres |
| 2012/0321579 A1 | 12/2012 | Edelson |
| 2012/0322779 A9 | 12/2012 | Voskuhl |
| 2012/0328549 A1 | 12/2012 | Edelson |
| 2012/0329738 A1 | 12/2012 | Liu |
| 2013/0004619 A1 | 1/2013 | Goh |
| 2013/0011342 A1 | 1/2013 | Hazot |
| 2013/0017239 A1 | 1/2013 | Fernandez Botello |
| 2013/0022674 A1 | 1/2013 | Dudley et al. |
| 2013/0023505 A1 | 1/2013 | Garfield |
| 2013/0023823 A1 | 1/2013 | Volland |
| 2013/0028850 A1 | 1/2013 | Hazot |
| 2013/0029947 A1 | 1/2013 | Nachaegari et al. |
| 2013/0029957 A1 | 1/2013 | Venkateshwaran |
| 2013/0045266 A1 | 2/2013 | Kang |
| 2013/0045953 A1 | 2/2013 | Grenier |
| 2013/0059795 A1 | 3/2013 | Lo |
| 2013/0064897 A1 | 3/2013 | Binay |
| 2013/0072466 A1 | 3/2013 | Choi |
| 2013/0084257 A1 | 4/2013 | Ishida |
| 2013/0085123 A1 | 4/2013 | Zhao |
| 2013/0089574 A1 | 4/2013 | Stock |
| 2013/0090318 A1 | 4/2013 | Gainer |
| 2013/0102781 A1 | 4/2013 | Ely |
| 2013/0108551 A1 | 5/2013 | Gruell |
| 2013/0116215 A1 | 5/2013 | Lleo |
| 2013/0116222 A1 | 5/2013 | Altomari |
| 2013/0122051 A1 | 5/2013 | Gullapalli |
| 2013/0123175 A1 | 5/2013 | McKee |
| 2013/0123220 A1 | 5/2013 | Queiroz |
| 2013/0123351 A1 | 5/2013 | Dewitt |
| 2013/0129818 A1 | 5/2013 | Bernick et al. |
| 2013/0131027 A1 | 5/2013 | Schmitz |
| 2013/0131028 A1 | 5/2013 | Snyder |
| 2013/0131029 A1 | 5/2013 | Bakker et al. |

(56) References Cited

U.S. PATENT DOCUMENTS

| | | |
|---|---|---|
| 2013/0149314 A1 | 6/2013 | Bullerdiek |
| 2013/0164225 A1 | 6/2013 | Besonov |
| 2013/0164346 A1 | 6/2013 | Son |
| 2013/0165744 A1 | 6/2013 | Carson |
| 2013/0178452 A1 | 7/2013 | King |
| 2013/0183254 A1 | 7/2013 | Cochran |
| 2013/0183325 A1 | 7/2013 | Sforzini |
| 2013/0189193 A1 | 7/2013 | Besonov |
| 2013/0189196 A1 | 7/2013 | Tamarkin |
| 2013/0189230 A1 | 7/2013 | Kooy |
| 2013/0189368 A1 | 7/2013 | Mosqueira |
| 2013/0210709 A1 | 8/2013 | Covic |
| 2013/0216550 A1 | 8/2013 | Penninger |
| 2013/0216596 A1 | 8/2013 | Fernandez Botello |
| 2013/0224177 A1 | 8/2013 | Kim |
| 2013/0224257 A1 | 8/2013 | Sah |
| 2013/0224268 A1 | 8/2013 | Jaikaria |
| 2013/0224300 A1 | 8/2013 | Maggio |
| 2013/0225412 A1 | 8/2013 | Sardari Lodriche |
| 2013/0225542 A1 | 8/2013 | Frick |
| 2013/0226113 A1 | 8/2013 | Langguth |
| 2013/0243696 A1 | 9/2013 | Wang |
| 2013/0245253 A1 | 9/2013 | Mook |
| 2013/0245570 A1 | 9/2013 | Jackson |
| 2013/0261096 A1 | 10/2013 | Merian |
| 2013/0266645 A1 | 10/2013 | Schoenecker |
| 2013/0267485 A1 | 10/2013 | Da Silva |
| 2013/0273167 A1 | 10/2013 | Kim |
| 2013/0274211 A1 | 10/2013 | Prusthy |
| 2013/0280213 A1 | 10/2013 | Voskuhl |
| 2013/0316374 A1 | 11/2013 | Menon |
| 2013/0317065 A1 | 11/2013 | Seto |
| 2013/0317315 A1 | 11/2013 | Tsang |
| 2013/0324565 A1 | 12/2013 | Zhao |
| 2013/0331363 A1 | 12/2013 | Zhao |
| 2013/0338122 A1 | 12/2013 | Bernick et al. |
| 2013/0338123 A1 | 12/2013 | Bernick et al. |
| 2013/0338124 A1 | 12/2013 | Zhao |
| 2013/0345187 A1 | 12/2013 | Rodriguez Oquendo |
| 2014/0018335 A1 | 1/2014 | Seto |
| 2014/0024590 A1 | 1/2014 | Taylor |
| 2014/0031289 A1 | 1/2014 | Kim |
| 2014/0031323 A1 | 1/2014 | Perez |
| 2014/0066416 A1 | 3/2014 | Leunis |
| 2014/0072531 A1 | 3/2014 | Oh |
| 2014/0079686 A1 | 3/2014 | Prouty |
| 2014/0088051 A1 | 3/2014 | Bernick et al. |
| 2014/0088058 A1 | 3/2014 | Maurizio |
| 2014/0088059 A1 | 3/2014 | Santha |
| 2014/0094426 A1 | 4/2014 | Drummond |
| 2014/0094440 A1 | 4/2014 | Bernick et al. |
| 2014/0094441 A1 | 4/2014 | Bernick et al. |
| 2014/0099362 A1 | 4/2014 | Bernick et al. |
| 2014/0100159 A1 | 4/2014 | Conrad |
| 2014/0100204 A1 | 4/2014 | Bernick et al. |
| 2014/0100205 A1 | 4/2014 | Bernick et al. |
| 2014/0100206 A1 | 4/2014 | Cacace |
| 2014/0113889 A1 | 4/2014 | Haine |
| 2014/0127185 A1 | 5/2014 | Sayeed |
| 2014/0127280 A1 | 5/2014 | Jukarainen |
| 2014/0127308 A1 | 5/2014 | Opara |
| 2014/0128798 A1 | 5/2014 | Malanchin |
| 2014/0148491 A1 | 5/2014 | Valia et al. |
| 2014/0186332 A1 | 7/2014 | Ezrin |
| 2014/0187487 A1 | 7/2014 | Shoichet |
| 2014/0193523 A1 | 7/2014 | Henry |
| 2014/0194396 A1 | 7/2014 | Wennogle |
| 2014/0206616 A1 | 7/2014 | Ko et al. |
| 2014/0213565 A1 | 7/2014 | Bernick et al. |
| 2014/0329783 A1 | 11/2014 | Bernick et al. |
| 2014/0370084 A1 | 12/2014 | Bernick et al. |
| 2014/0371182 A1 | 12/2014 | Bernick et al. |
| 2014/0371183 A1 | 12/2014 | Bernick et al. |
| 2014/0371184 A1 | 12/2014 | Bernick et al. |
| 2014/0371185 A1 | 12/2014 | Bernick et al. |
| 2015/0031654 A1 | 1/2015 | Amadio |
| 2015/0045335 A1 | 2/2015 | Bernick et al. |
| 2015/0133421 A1 | 5/2015 | Bernick et al. |
| 2015/0148323 A1 | 5/2015 | Bernick et al. |
| 2015/0164789 A1 | 6/2015 | Bernick et al. |
| 2015/0224117 A1 | 8/2015 | Bernick et al. |
| 2015/0224118 A1 | 8/2015 | Bernick et al. |
| 2015/0297733 A1 | 10/2015 | Oberegger et al. |
| 2015/0302435 A1 | 10/2015 | Bernick et al. |
| 2015/0342963 A1 | 12/2015 | Bernick et al. |
| 2015/0352126 A1 | 12/2015 | Bernick et al. |
| 2015/0359737 A1 | 12/2015 | Bernick et al. |
| 2016/0030449 A1 | 2/2016 | Persicaner et al. |
| 2016/0213685 A1 | 7/2016 | Bernick et al. |
| 2017/0056418 A1 | 3/2017 | Thorsteinsson et al. |
| 2017/0216310 A1 | 8/2017 | Mirkin et al. |
| 2017/0281645 A1 | 10/2017 | Shadiack et al. |
| 2017/0281646 A1 | 10/2017 | Inskeep et al. |
| 2017/0281647 A1 | 10/2017 | Shadiack et al. |
| 2017/0281776 A1 | 10/2017 | Shadiack et al. |
| 2018/0161343 A1 | 6/2018 | Mirkin et al. |
| 2018/0161344 A1 | 6/2018 | Mirkin et al. |
| 2018/0161345 A1 | 6/2018 | Bernick et al. |
| 2018/0221389 A1 | 8/2018 | Amadio et al. |

FOREIGN PATENT DOCUMENTS

| | | |
|---|---|---|
| EP | 0785211 A1 | 7/1997 |
| EP | 0785212 A1 | 7/1997 |
| EP | 0811381 A1 | 12/1997 |
| EP | 0904064 A1 | 3/1999 |
| EP | 0813412 B1 | 12/1999 |
| EP | 1300152 A1 | 4/2003 |
| EP | 1094781 B1 | 7/2008 |
| EP | 2191833 A1 | 6/2010 |
| ES | 2377616 B1 | 2/2013 |
| GB | 452238 A | 8/1936 |
| GB | 720561 A | 12/1954 |
| GB | 848881 A | 9/1960 |
| GB | 874368 A | 8/1961 |
| GB | 1589946 A | 5/1981 |
| IN | 2005KOL00053 | 8/2005 |
| IN | 216026 | 3/2008 |
| IN | 244217 | 11/2010 |
| JP | H4-503810 | 9/1990 |
| JP | H2-264725 A | 10/1990 |
| JP | 2002 510336 A | 4/2002 |
| JP | 2006 513182 A | 4/2006 |
| RU | 2155582 C2 | 9/2000 |
| RU | 2436579 C2 | 6/2008 |
| WO | 199010425 A1 | 9/1990 |
| WO | 1990011064 | 10/1990 |
| WO | 1993017686 | 9/1993 |
| WO | 1994022426 | 10/1994 |
| WO | 1995005807 | 3/1995 |
| WO | 1995030409 | 11/1995 |
| WO | 1996009826 | 4/1996 |
| WO | 1996019975 | 7/1996 |
| WO | 1996030000 | 10/1996 |
| WO | 1997005491 | 2/1997 |
| WO | 1997040823 A1 | 11/1997 |
| WO | 1997043989 | 11/1997 |
| WO | 1998010293 | 3/1998 |
| WO | 1998032465 | 7/1998 |
| WO | 1998041217 A1 | 9/1998 |
| WO | 1998051280 | 11/1998 |
| WO | 1999022680 A1 | 5/1999 |
| WO | 1999032072 | 7/1999 |
| WO | 1999039700 | 8/1999 |
| WO | 1999042109 | 8/1999 |
| WO | 1999043304 | 9/1999 |
| WO | 1999048477 | 9/1999 |
| WO | 1999052528 A1 | 10/1999 |
| WO | 1999053910 | 10/1999 |
| WO | 1999055333 A1 | 11/1999 |
| WO | 1999062497 A1 | 12/1999 |
| WO | 1999063974 | 12/1999 |
| WO | 2000001351 | 1/2000 |
| WO | 2000006175 | 2/2000 |

(56) References Cited

FOREIGN PATENT DOCUMENTS

| | | |
|---|---|---|
| WO | 2000038659 | 6/2000 |
| WO | 2000045795 | 8/2000 |
| WO | 2000050007 | 8/2000 |
| WO | 2000059577 | 10/2000 |
| WO | 2000076522 | 12/2000 |
| WO | 2001037808 | 5/2001 |
| WO | 2001054699 | 8/2001 |
| WO | 2001060325 | 8/2001 |
| WO | 2001087276 | 11/2001 |
| WO | 2001091757 | 12/2001 |
| WO | 2002007700 | 1/2002 |
| WO | 2002011768 | 2/2002 |
| WO | 2002022132 | 3/2002 |
| WO | 2002040008 | 5/2002 |
| WO | 2002041878 | 5/2002 |
| WO | 2002053131 | 7/2002 |
| WO | 2002078602 | 10/2002 |
| WO | 2002078604 | 10/2002 |
| WO | 2003028667 | 4/2003 |
| WO | 2003041718 | 5/2003 |
| WO | 2003041741 | 5/2003 |
| WO | 2003068186 | 8/2003 |
| WO | 2003077923 | 9/2003 |
| WO | 2003082254 | 10/2003 |
| WO | 2003092588 | 11/2003 |
| WO | 2004014397 A1 | 2/2004 |
| WO | 2004014432 | 3/2004 |
| WO | 2004017983 | 3/2004 |
| WO | 2004032897 | 4/2004 |
| WO | 2004032942 A1 | 4/2004 |
| WO | 2004052336 | 6/2004 |
| WO | 2004054540 | 7/2004 |
| WO | 2004054576 A1 | 7/2004 |
| WO | 2004080413 | 9/2004 |
| WO | 2004105694 A2 | 12/2004 |
| WO | 2004110402 A1 | 12/2004 |
| WO | 2004110408 A2 | 12/2004 |
| WO | 2005027911 | 3/2005 |
| WO | 2005030175 | 4/2005 |
| WO | 2005081825 | 9/2005 |
| WO | 2005087194 | 9/2005 |
| WO | 2005087199 | 9/2005 |
| WO | 2005105059 | 11/2005 |
| WO | 2005115335 | 12/2005 |
| WO | 2005120470 | 12/2005 |
| WO | 2005120517 | 12/2005 |
| WO | 2006013369 | 2/2006 |
| WO | 2006034090 | 3/2006 |
| WO | 2006036899 | 4/2006 |
| WO | 2006053172 | 5/2006 |
| WO | 2006105615 | 10/2006 |
| WO | 2006113505 | 10/2006 |
| WO | 2006138686 | 12/2006 |
| WO | 2006138735 | 12/2006 |
| WO | 2007045027 | 4/2007 |
| WO | 2007076144 A2 | 7/2007 |
| WO | 2007103294 | 9/2007 |
| WO | 2007120868 | 10/2007 |
| WO | 2007123790 | 11/2007 |
| WO | 2007124250 | 11/2007 |
| WO | 2007144151 | 12/2007 |
| WO | 2008049516 | 5/2008 |
| WO | 2008152444 | 12/2008 |
| WO | 2009002542 | 12/2008 |
| WO | 2009036311 | 3/2009 |
| WO | 2009040818 | 4/2009 |
| WO | 2009069006 | 6/2009 |
| WO | 2009098072 | 8/2009 |
| WO | 2009133352 | 11/2009 |
| WO | 2010033188 | 3/2010 |
| WO | 2010146872 | 12/2010 |
| WO | 2011000210 | 1/2011 |
| WO | 2011073995 | 6/2011 |
| WO | 2011120084 | 10/2011 |
| WO | 2011128336 | 10/2011 |
| WO | 2012009778 | 1/2012 |
| WO | 2012024361 | 2/2012 |
| WO | 2012055814 A1 | 5/2012 |
| WO | 2012055840 A1 | 5/2012 |
| WO | 2012065740 | 5/2012 |
| WO | 2012098090 A1 | 7/2012 |
| WO | 2012116277 A1 | 8/2012 |
| WO | 2012118563 A2 | 9/2012 |
| WO | 2012120365 A1 | 9/2012 |
| WO | 2012127501 A2 | 9/2012 |
| WO | 2012156561 A1 | 11/2012 |
| WO | 2012156822 A1 | 11/2012 |
| WO | 2012158483 A2 | 11/2012 |
| WO | 2012166909 A1 | 12/2012 |
| WO | 2012170578 A1 | 12/2012 |
| WO | 2013011501 A1 | 1/2013 |
| WO | 2013025449 A1 | 2/2013 |
| WO | 2013028639 A1 | 2/2013 |
| WO | 2013035101 A1 | 3/2013 |
| WO | 2013044067 A1 | 3/2013 |
| WO | 2013045404 A2 | 4/2013 |
| WO | 2013059285 A1 | 4/2013 |
| WO | 2013063279 A1 | 5/2013 |
| WO | 2013064620 A1 | 5/2013 |
| WO | 2013071281 A1 | 5/2013 |
| WO | 2013078422 A2 | 5/2013 |
| WO | 2013088254 | 6/2013 |
| WO | 2013102665 A1 | 7/2013 |
| WO | 2013106437 A1 | 7/2013 |
| WO | 2013112947 A1 | 8/2013 |
| WO | 2013113690 | 8/2013 |
| WO | 2013124415 A1 | 8/2013 |
| WO | 2013127727 A1 | 9/2013 |
| WO | 2013127728 A1 | 9/2013 |
| WO | 2013144356 A1 | 10/2013 |
| WO | 2013149258 A2 | 10/2013 |
| WO | 2013158454 A2 | 10/2013 |
| WO | 2013170052 A1 | 11/2013 |
| WO | 2013178587 A1 | 12/2013 |
| WO | 2013181449 A1 | 12/2013 |
| WO | 2013192248 | 12/2013 |
| WO | 2013192249 | 12/2013 |
| WO | 2013192250 | 12/2013 |
| WO | 2013192251 | 12/2013 |
| WO | 2014001904 A1 | 1/2014 |
| WO | 2014004424 A1 | 1/2014 |
| WO | 2014009434 A1 | 1/2014 |
| WO | 2014018569 A1 | 1/2014 |
| WO | 2014018570 A1 | 1/2014 |
| WO | 2014018571 A2 | 1/2014 |
| WO | 2014018856 A1 | 1/2014 |
| WO | 2014018932 A2 | 1/2014 |
| WO | 2014031958 A1 | 2/2014 |
| WO | 2014041120 A1 | 3/2014 |
| WO | 2014052792 A1 | 4/2014 |
| WO | 2014056897 A1 | 4/2014 |
| WO | 2014066442 A2 | 5/2014 |
| WO | 2014074846 A1 | 5/2014 |
| WO | 2014076231 A1 | 5/2014 |
| WO | 2014076569 A2 | 5/2014 |
| WO | 2014081598 A1 | 5/2014 |
| WO | 2014086739 A1 | 6/2014 |
| WO | 2014093114 A1 | 6/2014 |
| WO | 2014104784 A1 | 7/2014 |
| WO | 2015179782 A1 | 11/2015 |
| WO | 2016018993 A1 | 2/2016 |

OTHER PUBLICATIONS

Chambin et al, "Interest of Multifunctional Lipid Excipients: Case of Gelucire® 44/14," Drug Development and Industrial Pharmacy, vol. 31, No. 6, pp. 527-534 (Year: 2005).*

Abbas et al., Regression of endometrial implants treated with vitamin $D_3$ in a rat model of endometriosis, European J of Pharma, 715 (2013) 72-75, Elsevier.

Abitec, CapmulMCM, EP, Technical Data Sheet, version 10, 2014, Columbus, OH.

(56) References Cited

OTHER PUBLICATIONS

Abitec, CapmulMCM, NF, Technical Data Sheet, version 6, 2014, Columbus, OH.
Abitec, CapmulMCM, Saftey Data Sheet, 2011, Janesville, WI.
Abitec, CapmulMCM, Technical Data Sheet, version 17, 2014, Columbus, OH.
Abitec, CapmulPG8, CAS No. 31565-12-5, version 11, 2006, Columbus, OH.
Abitec, Excipients for the Pharmaceutical Industry—Regulatory and Product Information, 2013, 2 pages.
Acarturk, Fusun, Mucoadhesive Vaginal Drug Delivery System, Recent Patents on Drug Delivery & Formulation, 2009, vol. 3, pp. 193-195.
Alabi, K. A., et al., Analysis of Fatty Acid Composition of Thevetia peruviana and Hura crepitans Seed oils using GC-FID, Fountain Journal of Nat. and Appl. Sciences, vol. 2(2), pp. 32-37, 2013, Osogbo.
Alexander, KS, Corn Oil, CAS No. 8001-30-7, Jan. 2009.
Alvarez et al., Ectopic uterine tissue as a chronic pain generator, Neuroscience, Dec. 6, 2012, 225: 269-272.
Application Note FT-IR: JI-Ap-FT0508-008, CD spectra of pharmaceuticals substances—Steroids (2), JASCO International Co., Ltd., 2 pages.
Araya-Siblja et al., Crystallization of progesterone polymorphs using polymer-induced heteronucleation (PIHn) method, Drug Development and Industrial Pharmacy, Early Online, pp. 1-8, 2014, Informa Healthcare.
Araya-Siblja, Andrea M.A., Morphology Study of Progesterone Polymorphs Prepared by Polymer-Induced Heteronucleation (PIHn), Scanning vol. 35 pp. 213-221, 2013, Wiley Period., Inc.
Araya-Siblja, Andrea Manela, et al., Chemical Properties of Progesterone Selected Refer., SciFinder, 2014, American Chemical Society & US Natl. Lib. of Med.
Araya-Siblja, Andrea Manela, et al., Polymorphism in Progesterone Selected References, SciFinder, Feb. 24, 2014, pp. 1-12, American Chem. Society & Natl. Lib. of Med.
Araya-Siblja, Andrea Manela, et al., Polymorphism in Progesterone, SciFinder, pp. 1-46, Feb. 24, 2014, American Chem. Society & Natl. Lib. of Med.
Archer et al., Effects of ospemifene on the female reproductive and urinary tracts: translation from preclinical models into clinical evidence, Menopause: The Journal of the North American Menopause Society, vol. 22, No. 77, pp. 1-11 (2015).
Archer et al., Estrace® vs Premarin® for Treatment of Menopausal Symptoms: Dosage Comparison Study, Advances in Therapy®, vol. 9 No. 1, Jan./Feb. 1992.
Ashburn et al., Cardiovascular, Hepatic and Renal Lesions in Mice Receiving Cortisone, Estrone and Progesterone, Yale J Bilogy and Medicine, vol. 35, Feb. 1963, pp. 329-340.
Azeem, Adnan et al., Microemulsions as a Surrogate Carrier for Dermal Drug Delivery, Drug Development and Industrial Pharmacy, May 2000, vol. 35, No. 5, pp. 525-547 (abstract only). http://informahealtheare.com/doi/abs/10.1080/03639040802448646.
Azure Pharma, Inc., ELESTRIN™—Estradiol Gel, Drug Info, http://dailymed.nlm.nih.gov/dailymed/archives/fdaDrugInfo.cfm?archiveid=11885, 26 pages, Aug. 2009.
Bakhmutova-Albert, Ekaterina, et al., Enhancing Aqueous Dissolution Rates of Progesterone via Cocrystallization, SSCI, Division of Aptuit, Poster No. R6247, West Lafayette.
Banerjee, Sila, et al., On the Stability of Salivary Progesterone Under Various Conditions of Storage, Steroids, vol. 46(6), pp. 967-974, Dec. 1985.
Barnett, Steven M, Pressure-tuning infared and solution Raman spectroscopic studies of 17B-estradiol and several A-ring . . . , Vibrational Spectroscopy 8, Elsevier, pp. 263, 1995.
Bartosova, Transdermal Drug Delivery In Vitro Using Diffusion Cells, Current Medicinal Chemistry, 2012, 19, 4671-4677, Bentham Science Publishers.

Benbow et al., Distribution and Metabolism of Maternal Progesterone in the Uterus, Placenta, and Fetus during Rat Pregnancy, Biology of Reproduction 52, 1327-1333 (1995).
Bernabei, M.T., et al., Release of progesterone polymorphs from dimethylpolysiloxane polymeric matrixes, Bollettino Chimico Farmaceutico, vol. 122(1) pp. 20-26, 1983 SciFinder.
Bhavnani Bhagu R. et al., "Misconception and Concerns about Bioidentical Hormones Used for Custom-Compounded Hormone Therapy," J Clin Endocrinol Metab, Mar. 2012, 97(3):756-759.
Bhavnani et al., Structure Activity Relationships and Differential Interactions and Functional Activity of Various Equine Estrogens Mediated via Estrogen Receptors (ERs) ERα and ERβ, Endocrinology, Oct. 2008, 149(10):4857-4870.
Bhavnani, B.R., Stanczyk, F.Z., Pharmacology of conjugated equine estrogens: Efficacy, safety and mechanism of action, J. Steroid Biochem. Mol. Biol. (2013), Elsevier.
Bhavnani, B.R., Stanczyk, F.Z., Use of medroxyprogesterone acetate for hormone therapy in postmenopausal women: Is it safe? J. Steroid Biochem. Mol. Biol. (2013), Elsevier.
BioMed Central, Solubility of Progesterone in Organic Solvents, Online PDF, http://www.biomedcentral.com/content/supplementary/1475-2859-11-106-S2.pdf.
Blake et al., Single and multidose pharmacokinetic study of a vaginal micronized progesterone insert (Endometrin) compared with vaginal gel in healthy reproductiveaged female subjects, Fertility and Sterility# vol. 94, No. 4, Sep. 2010, Elsevier.
Borka, Laszlo, Crystal Polymorphism of Pharmaceuticals, Acta Pharm. Jugosl., vol. 40 pp. 71-94, 1990.
Brinton, L.A., Felix, A.S., Menopausal hormone therapy and risk of endometrial cancer, J. Steroid Biochem. Mol. Biol. (2013), Elsevier.
British Pharmacocopoeia 2014 Online, Refined Maize Oil, Ph. Eur. Monograph 1342, vol. I & II, Monographs: Medicinal and Pharmaceutical Substances, http://www.pharmacopoeia.co.uk/bp2014/ixbin/bp.cgi?a=print&id=7400&tab=a-z%20index [Feb. 3, 2014 1:37:50 PM].
Burry, Kenneth A, Percutaneous absorption of progesterone in postmenopausal women treated with transdermal estrogen, Am J Obstet Gynecol, vol. 180(6) part 1, pp. 1504-1511, 1999.
Busetta, Par Bernard, Structure Cristalline et Moleculair de l'Oestradiol Hemihydrate, Acta Cryst., B28 pp. 560, 1972, Bis(dimethyl-o-thiolophenylarsine)palladium(II).
Busetta, Par Bernard, Structure Cristalline et Moleculaire du Complexe Oestradiol-Propanol, Acta Cryst., B28 pp. 1349, 1972, J.A. Kanters and J. Kroon.
Campsteyn, Par H, et al., Structure Cristalline et Molcculaire de la Progesterone C21H30O2, Acta Cryst., B28 pp. 3032-3042, 1972.
Cendejas-Santana, G, et al., Growth and characterization of progesterone crystallites, Revista Mexicana de Fisica, 50, Suplemento 1 pp. 1-3, 2004.
ChemPro, Top-Notch Technology in Production of Oils and Fats, Chempro-Edible-Oil-Refining-ISO-TUV-Austria Available May 26, 2010.
Christen et al., Phase I/Pharmacokinetic Study of High-Dose Progesterone and Doxorubicin, J Clin Oncol 11:2417-2426, 1993.
Christensson et al., Limonene hydroperoxide analogues differ in allergenic activity, Contact Dermatitis 2008: 59: 344-352.
Christensson et al., Limonene hydroperoxide analogues show specific patch test reactions, Contact Dermatitis, 70, 291-299, 2014.
Christensson et al., Positive patch test reactions to oxidized limonene: exposure and relevance , Contact Dermatitis, 71, 264-272, 2014.
Chun et al., Transdermal Delivery of Estradiol and Norethrindrone Acetate: Effect of Vehicles . . . , J. Kor. Pharm. Sci., vol. 35, No. 3, pp. 173-177 (2005).
Cicinelli et al., Direct Transport of Progesterone From Vagina to Uterus, Obstetrics & Gynecology, vol. 95, No. 3, Mar. 2000, pp. 403-406.
Cole, Wayne & Julian, Percy L, Sterols. I. A Study of the 22-Ketosteroids, Cont. of the Research Lab. of the Glidden Co., Soya Prod. Div., vol. 67 pp. 1369-1375, Aug. 1945, Chicago.
Committee Opinion, Incidentally Detected Short Cervical Length, Committee of Obstetric Practice, Obstetrics & Gynecology, ACOG, vol. 119, No. 4, Apr. 2012, pp. 879-882.

(56) References Cited

OTHER PUBLICATIONS

Commodari, Fernando, Comparison of 17β-estradiol structures from x-ray diffraction and solution NMR, Magn. Reson. Chem., vol. 43, pp. 444-450, 2005, Wiley InterScience.
Cooper, A, et al., Systemic absorption of progesterone from Progest cream in postmenopausal women, The Lancet, vol. 351, pp. 1255-1256, Research Letters, Apr. 25, 1998.
Corbett et al., "Trends in Pharmacy Compounding for Women's Health in North Carolina: Focus on Vulvodynia," Southern Medical Journal, vol. 107, No. 7, Jul. 2014, pp. 433-436.
Corn Refiners Association, Corn Oil, 5th Edition, Washington, D.C., 2006.
Critchley et al., Estrogen Receptor β, But Not Estrogen Receptor α, Is Present in the Vascular Endothelium of the Human and Nonhuman Primate Endometrium, The Journal of Clinical Endocrinology & Metabolism, 2001, vol. 86, No. 3, pp. 1370-1378.
Dauqan, Eqbll M. A., et al., Fatty Acids Composition of Four Different Vegetable Oils (Red Palm Olein, Palm Olein, Corn Oil, IPCBEE, vol. 14, 2011, IACSIT Press, Singapore.
Dideberg, O, et al., Crystal data on progesterone (C21H3002), desoxycorticosterone (C21H3003), corticosterone (C21H3004) and aldosterone . . . , J. Appl. Cryst. vol. 4 pp. 80, 1971.
Diramio, Jackie A., Polyethylene Glycol Methacrylate/Dimetacrylate Hydrogels for Controlled Release of Hydrophobic Drugs, Masters of Science Thesis, University of Georgia, Athens, Georgia, 2002, 131 pages.
Drakulic, Branko J, Role of complexes formation between drugs and penetration enhancers in transdermal . . . , Inter. Journal of Pharmaceutics, Elsevier, vol. 363, pp. 40-49, 2009.
Du et al., Percutaneous progesterone delivery via cream or gel application in postmenopausal women: a randomized cross-over study of progesterone levels in serum, whole blood, saliva, and capillary blood, Menopause: The Journal of The North American Menopause Society, 2013, vol. 20, No. 11, pp. 1-7.
Duax, William L, et al., Conformation of Progesterone Side Chain: Conflict between X-ray Data and Force-Field Calculations, J. Am. Chem. Soc., vol. 103 pp. 6705-6712, Jun. 1981.
Duclos, R, et al., Polymorphism of Progesterone: Influence of the carrier and of the solid dispersion manufacturing . . . , J. Thermal Anal., vol. 37 pp. 1869-1875, 1991, Wiley.
Ebian, A.R., Ebian Article: Polymorphism and solvation of ethinyl estradiol, SciFinder, Pharmaceutica Acta Helvetiae, vol. 54(4), pp. 111-114, 1979, Alexandria, Egypt.
Eisenberger, A., Westhoff, C., Hormone replacement therapy and venous thromboembolism, J. Steroid Biochem. Mol. Biol. (2013), Elsevier.
Engelhardt et al., Conceptus Influences the Distribution of Uterine Leukocytes During Early Porcine Pregnancy, Biology of Reproduction 66, 1875-1880 (2002).
Estradiol, The Merck Index Online, Royal Society of Chemistry, https://www.rsc.org/Merck-Index/monograph/mono1500003758/estradiol?q=unauthorize.
Ettinger et al., Comparison of endometrial growth produced by unopposed conjugated estrogens or by micronized estradiol in postmenopausal women, Am J Obstet Gynecol 1997; 176:112-117.
Excipients for Pharmaceuticals, Sasol Olefins & Surfactants GmbH, 2010, 28 pages.
Faassen, Fried, Physicochemical Properties and Transport of Steroids across Caco-2 Cells, Pharmaceutical Research, vol. 20(2), 2003, Plenum Pub. Corp.
FDA, Draft Guidance on Progesterone, Recommended Apr. 2010, Revised Feb. 2011 http://www.fda.gov/downloads/Drugs/GuidanceComplianceRegulatoryInformation/Guidances/UCM209294.pdf.
Ferrari, Roseli AP., et al., Oxidative Stability of Biodiesel From Soybean Oil Fatty Acid Ethyl Esters, Sci. Agric., vol. 62(3), pp. 291-295, 2005, PiracicaB1, Braz.
Filipsson et al., Concise International Chemical Assessment Document 5: Limonene, first draft, World Health Organization, Geneva, 1998, 36 pages.

Final Report on the Safety Assessment of BHT, International Journal of Toxicology, 21(Suppl. 2):19-94, 2002/.
Flyvholm, Sensitizing risk of butylated hydroxytoluene B1sed on exposure and effect data, Contact Dermatitis 1990: 23: 341-345.
Fotherby, K., Bioavailability of Orally Administered Sex Steroids Used in Oral Contraception and Hormone Replacement Therapy, Contraception, 1996; 54:59-69.
Franklin et al., Characterization of immunoglobulins and cytokines in human cervical mucus: influence of exogenous and endogenous hormones, Journal of Reproductive Immunology 42 (1999) 93-106, Elsevier.
Franz et al., Use of Excised Human Skin to Assess the Bioequivalence of Topical Products, Skin Pharmacol Physiol 2009;22:276-286.
Freedman, R.R., Menopausal hot flashes: Mechanisms, endocrinology, treatment, J. Steroid Biochem. Mol. Biol.(2013), Elsevier.
Fuchs et al., The Effects of an Estrogen and Glycolic Acid Cream on the Facial Skin of Postmenopausal Women: A Randomized Histologic Study, Cutis. Jun. 2003;71(6):481-8.
Fugh-Berman, Adriane, Bioidentical Hormones for Menopausal Hormone Therapy: Variation on a Theme, Journal of General Internal Medicine, vol. 22, pp. 1030-1034, 2007.
Furness et al., Hormone therapy in postmenopausal women and risk of endometrial hyperplasia (Review), 2012, pp. 1-204, The Cochrane Collaboration. Published by JohnWiley & Sons, Ltd.
Gäfvert et al., Free radicals in antigen formation: reduction of contact allergic response to hydroperoxides by epidermal treatment with antioxidants, British Journal of Dermatology 2002; 146: 649-656.
Ganam-Quintanar et al., Evaluation of the transepidermal permeation of diethylene glycol monoethyl ether and skin water loss, International Journal of Pharmaceutics, vo. 147, No. 2, Feb. 28, 1997, pp. 165-171 (abstract only).
Gattefossé SAS, Material Safety Data Sheet, Gelot 64, 2012, 8 pages.
Gattefossé SAS, Regulatory Data Sheet, Gelot 64, 2012, 6 pages.
Gattefossé SAS, Regulatory Data Sheet, Lauroglycol 90, 2012, 5 pages.
Gattefossé, "Excipients for Safe and Effective Topical Delivery, Drug Development and Delivery" Jul./Aug. 2012, http://drug-dev.com/Main/B1ck-Issues/Transdermal-Topical-Subcutaneous-NonInvasive-Deliv-5.aspx#.
Geelen, Math J.H. et al., "Dietary medium-chain fatty acids raise and (n-3) polyunsaturated fatty acids lower hepatic triacylglycerol synthesis in rats," The Journal of Nutrition, 1995, 125(10):2449-2456.
Gillet et al., Induction of amenorrhea during hormone replacement therapy: optimal micronized progesterone dose. A multicenter study, Maturitas 19 (1994) 103-115.
Giron-Forest, D, et al., Thermal analyis methods for pharmacopoeial materials, J. Pharmaceutical & Biomedical Anal., vol. 7(12) pp. 1421-1433, 1989, Pergamon Press, Gr. Britain.
Giron-Forest, D, Thermal analysis and calorimetric methods in the characterisation of polymorphs and solvates, Thermochimica Acta, vol. 248 pp. 1-59, 1995, Elsevier.
Glaser et al, Pilot Study: Absorption and Efficacy of Multiple Hormones Delivered in a Single Cream Applied to the Mucous Membranes of the Labia and Vagina, Gynecol Obstet Invest 2008;66:111-118.
Golatowski et al., Comparative evaluation of saliva collection methods for proteome analysis, Clinica Chimica Acta 419 (2013) 42-46.
Graham et al, Physiological Action of Progesterone in Target Tissues, Endocrine Reviews, 1997, vol. 18, No. 4, pp. 502-519.
Groothuis et al., Estrogen and the endometrium: lessons learned from gene expression profiling in rodents and human, Human Reproduction Update, vol. 13, No. 4 pp. 405-417, 2007.
Gunstone, Frank D, et al., Vegetable Oils in Food Technology: Composition, Properties and Uses, Blackwell Publishing, CRC Press, 2002.
Gurney, E.P. et al., The Women's Health Initiative trial and related studies: 10 years later: A clinician's view, J.Steroid Biochem. Mol. Biol. (2013), Elsevier.

(56) References Cited

OTHER PUBLICATIONS

Hamid et al., The effects of common solubilizing agents on the intestinal membrane B1rrier functions and membrane toxicity in rats, International Journal of Pharmaceutics 379 (2009) 100-108, Elsevier.
Haner, Barbara, Crystal data (I) for some pregnenes and pregnadienes, Acta Cryst., vol. 17 pp. 1610, 1964.
Hapgood, J.P., et al., Potency of progestogens used in hormonal therapy: Toward understanding differential actions, J. Steroid Biochem. Mol. Biol. (2013), Elsevier.
Hargrove et al., Menopausal Hormone Replacement Therapy With Continuous Daily Oral Micronize Estradiol and Progesterone, Obstet Gynecol, vol. 73, No. 4, Apr. 1989, pp. 606-612.
Hatton et al., "Safety and efficacy of a lipid emulsion containing medium-chain triglycerides," Clinical Pharmacy, 1990, vol. 9, No. 5, pp. 366-371.
He et al., Apoptotic Signaling Pathways in Uteri of Rats with Endometrial Hyperplasia Induced by Ovariectomy Combined with Estrogen, Gynecol Obstet Invest 2013;76:51-56.
Helbling, Ignacio M, et al., The Optimization of an Intravaginal Ring Releasing Progesterone Using a Mathematical Model, Pharm Res, vol. 31 pp. 795-808, 2014, Springer Science.
Helmy et al., Estrogenic Effect of Soy Phytoestrogens on the Uterus of Ovariectomized Female Rats, Clinic Pharmacol Biopharmaceut, 2014, S2, 7 pages.
Henderson, V.W., Alzheimer's disease: Review of hormone therapy trials and implications for treatment and prevention after . . . , J. Steroid Biochem. Mol. Biol. (2013), Elsevier.
Henriksen, Thormod, et al., An ENDOR Sturdy of Radiation-Induced Molecular Damage to Progesterone, Jour. of Mag. Resonance, vol. 63, pp. 333-342, 1985, Acedemic Press, Inc.
Herman, Anna et al., "Essential oils and their constituents as skin penetration enhancer for transdermal drug delivery: a review," 2014 Royal Pharmaceutical Society, Journal of Pharmacy and Pharmacology, pp. 1-13.
Hodis, H.N., Mack, W.J., Hormone replacement therapy and the association with heart disease and overall mortality: Clinical . . . , J. Steroid Biochem. Mol. Biol. (2013), Elsevier.
Hospital, Michel, et al., X-ray Crystallography of Estrogens and Their Binding to Receptor Sites, Mol. Pharmacology, vol. 8 pp. 438-445, Acedemic Press, Inc., 1972.
Hostynek, JJ, Predictinga bsorptiono f fragrancec hemicalst hrough human skin, j. Soc.C osmeCt. hem.,4 6, 221-229 (Jul./Aug. 1995).
Hulsmann, Stefan, Stability of Extruded 17B-Estradiol Solid Dispersions, Pharmaceutical Development and Tech., vol. 6(2) pp. 223-229, 2001, Marcel Dekker, Inc.
Humberstone, Andrew et al., "Lipid-based vehicles for the oral delivery of poorly water soluble drugs," Advanced Drug Delivery Reviews, 25 (1997) 103-128.
Hurn et al., Estrogen as a Neuroprotectant in Stroke, Journal of Cerebral Blood Flow and Metabolism 20:631-652, 2000, Lippincott Williams & Wilkins, Inc., Philadelphia.
Hyder et al., Synthetic Estrogen 17α-Ethinyl Estradiol Induces Pattern of Uterine Gene Expression Similar to Endogenous Estrogen 17β-Estradiol, JPET 290(2):740-747, 1999.
Idder, Salima, et al., Physicochemical properties of Progesterone, SciFinder, pp. 1-26, Feb. 24, 2014, American Chem. Society & US Natl. Lib. of Med.
Johanson, Gunnar, Toxicity Review of Ethylene Glycol Monomethyl Ether and its Acetate Ester, Critical Reviews in Toxicology, 2000, vol. 30, No. 3 , pp. 307-345 (abstract only). http://informahealthcare.com/doi/abs/10.1080/10408440091159220.
Johnson, William S, et al., Racemic Progesterone, Tetrahedron Letters No. 4, pp. 193-196, 1963, Pergamon Press Ltd., Great Britain.
Joshi et al., Detection and synthesis of a progestagen-dependent protein in human endometrium, J Reprod Fert (1980) 59, 273-285.

Kanno et al., The OECD Program to Validate the Rat Uterotrophic Bioassay to Screen Compounds for in Vivo Estrogenic Responses: Phase 1, Environmental Health Perspectives • vol. 1091 | No. 8 | Aug. 2001, pp. 785-794.
Karlberg et al., Air oxidation of d-limonene (the citrus solvent) creates potent allergens, Contact Dermatitis, 1992: 26: 332-340.
Karlberg et al., Influence of an anti-oxidant on the formation of allergenic compounds during auto-oxication of d-limonene, Ann. Occup. Hyg., vol. 38, No. 2, pp. 199-207, 1994.
Kaunitz, Andrew M., Extended duration use of menopausal hormone therapy, Menopause: The Journal of The North American Menopause Society, 2014, vol. 21, No. 6, pp. 1-3.
Khalil, Sah, Stability and Dissolution Rates of Corticosteroids in Polyethylene Glycol Solid Dispersions, Drug Dev. & Indus. Pharm., vol. 10(5) pp. 771-787, 1984, Marcel Dekker.
Kharode et al., The Pairing of a Selective Estrogen Receptor Modulator, B1zedoxifene, with Conjugated Estrogens as a New Paradigm for the Treatment of Menopausal Symptoms and Osteoporosis Prevention, Endocrinology 149(12):6084-6091, 2008.
Kim et al., Safety Evaluation and Risk Assessment of d-Limonene, Journal of Toxicology and Environmental Health, Part B: Critical Reviews, 2013, 16:1, 17-38 http://dx.doi.org/10.1080/10937404.2013.769418.
Kincl et al., Increasing Oral Bioavailability of Progesterone by Formulation, Journal of Steroid Biochemistry, 1978, vol. 9, pp. 83-84.
Knuth et al., Hydrogel delivery systems for vaginal and oral applications: Formulation and biological considerations, Advanced Drug Delivery Reviews, vol. 11, No. 1-2, Jul.-Aug. 1993, pp. 137-167 (abstract only).
Koga et al., Enhancing mechanism of Labrasol on intestinal membrane permeability of the hydrophilic drug gentamicin sulfate, European Journal of Pharmaceutics and Biopharmaceutics 64 (2006) 82-91.
Komm et al., B1zedoxifene Acetate: A Selective Estrogen Receptor Modulator with Improved Selectivity, Endocrinology 146(9):3999-4008, 2005.
Korkmaz, Filiz, Byophysical Studies of Progesterone-Model Membrane Interactions, Thesis, Grad. School of Nat. and App. Sci. of The Middle East Tech. University, Sep. 2003.
Kotiyan, P.N., Stability indicating HPTLC method for the estimation of estradiol, Journal of Pharmaceutical and Biomedical Analysis, vol. 22 pp. 667-671, 2000, Elsevier.
Krzyminiewski, R, et al., EPR Study of the Stable Radical in a y-Irradiated Single Crystal of Progesterone, Jour. of Mag. Resonance, vol. 46 pp. 300-305, 1982, Acedemic Press.
Kubli-Garfias, C, et al., Ab initio calculations of the electronic structure of glucocorticoids, Jour. of Mol. Structure, Theochem, vol. 454 pp. 267-275, 1998, Elsevier.
Kubli-Garfias, Carlos, Ab initio study of the electronic structure of progesterone and related progestins, Jour. of Mol. Structure, Theochem vol. 425, pp. 171-179, 1998, Elsevier (abstract only).
Kuhnert-Brandstaetter and Grimm. Zur Unterscheidung von losungsmittelhaltigen pseudopolymorphen Kristallformen und polymorphen Modifikationen bei Steroidhormonen.II, Mikrochimica Acta, vol. 1, pp. 127-139, 1968.
Kuhnert-Brandstaetter and Junger and Kofler. Thermo-microscopic and spectrophotometric: Determination of steroid hormones, Microchemical Journal 9, pp. 105-133, 1965.
Kuhnert-Brandstaetter and Kofler. Zur mikroskopischen Identitatsprufung und zur Polymorphic der Sexualhormone, Mikrochimica Acta, vol. 6, pp. 847-853, 1959.
Kuhnert-Brandstaetter and Linder. Zur Hydratbildung bei Steroidhormonen, Sci. Pharm, vol. 41(2), pp. 109-116, 1973.
Kumasaka et al., Effects of Various Forms of Progestin on the the Estrogen-Primed, Ovariectomized Rat, Endocrine Journal 1994, 41(2), 161-169.
Kuon et al., A Novel Optical Method to Assess Cervical Changes during Pregnancy and Use to Evaluate the Effects of Progestins on Term and Preterm Labor, Am J Obstet Gynecol. Jul. 2011; 205(1): 82.e15-82.e20.

(56) References Cited

OTHER PUBLICATIONS

Kuon et al., Actions of progestins for the inhibition of cervical ripening and uterine contractions to prevent preterm birth, FVV in Obgyn, 2012, 4 (2): 110-119.
Kuon et al., Pharmacological actions of progestins to inhibit cervical ripening and prevent delivery depend upon their properties, the route of administration and the vehicle, Am J Obstet Gynecol. May 2010 ; 202(5): 455.e1-455.e9.
Labrie, et al., Intravaginal prasterone (DHEA) provides local action without clinically significant changes in serum concentrations of estrogens or androgens, Journal of Steroid Biochemistry & Molecular Biology, vol. 138, pp. 359-367, 2013, Elsevier.
Lacey, J.V. Jr., The WHI ten year's later: An epidemiologist's view, J. Steroid Biochem. Mol. Biol. (2013), Elsevier.
Lahiani-Skib1, Malika, Solubility and Dissolution Rate of Progesterone-Cyclodextrin . . . , Drug Development and Industrial Pharmacy, Informa Healthcare vol. 32, pp. 1043-1058, 2006.
Lancaster, Robert W, et al., The Polymorphism of Progesterone: Stabilization of a 'Disappearing' Polymorph by . . . , Jour. of Pharm. Sci., vol. 96(12) pp. 3419-3431, 2007, Wiley-Liss.
Land, Laura M, The influence of water content of triglyceride oils on the solubility of steriods, Pharmaceutical Research, vol. 22(5) May 2005, Springer Science+Business Media.
Lauer et al., "Evaluation of the hairless rat as a model for in vivo percutaneous absorption," Journal of Pharmaceutical Sciences, vol. 86, No. 1, Jan. 1997, pp. 13-18.
Leonetti et al., Transdermal progesterone cream as an alternative progestin in hormone therapy, Alternative Therapies, Nov./Dec. 2005, vol. 11, No. 6, pp. 36-38.
Leonetti, Helene B, et al., Topical progesterone cream has an antiproliferative effect on estrogen-stimulated endometrium, Fertility and Sterility, vol. 79(1), Jan. 2003.
Lewis, John G. et al., Caution on the use of saliva measurements to monitor absorption of progesterone from transdermal creams in postmenopausal women, Maturitas, The European Menopause Journal, vol. 41, pp. 1-6, 2002.
Li, Guo-Chian, Solid-state NMR analysis of steroidal conformation of 17a- and 17B-estradiol in the absence and presence of lipi . . . , Steroids, Elsevier, vol. 77, pp. 185-192, 2012.
Lindmark, Tuulikki et al., "Absorption Enhancement through Intracellular Regulation of Tight Junction Permeability by Medium Chain Fatty Acids in Caco-2 Cells," JPET 284(1):362-369, 1998.
Lindmark, Tuulikki et al., "Mechanisms of Absorption Enhancement by Medium Chain Fatty Acids in Intestinal Epithelial Caco-2 Cell Monolayers," JPET 275(2):958-964, 1995.
Lobo, R.A., Foreword, J. Steroid Biochem. Mol. Biol. (2014), Elsevier.
López-Belmonte, Corrigendum to "Comparative uterine effects on ovariectomized rats after repeated treatment with different vaginal estrogen formulations" [Maturitas 72 (2012) 353-358], Maturitas 74 (2013) 393, Elsevier.
Lucy et al., Gonadotropin-releasing hormone at estrus: lutenizing hormone, estradiol, and progesterone during . . . Biol Reprod Sep. 1986;35(2):300-311 (abstract only).
Lvova, M. SH., et al., Thermal Analysis in the Quality Control and Standardization of Some Drugs, J Thermal Anal., vol. 40 pp. 405-411, 1993, Wiley.
Madishetti et al., Development of domperidone bilayered matrix type transdermal patches: physicochemical, in vitro and ex vivo characterization, DARU vol. 18, No. 3, 2010, pp. 221-229.
Magness, R.R., et al., Estrone, Estradiol-17β and Progesterone Concentrations in Uterine Lymph and Systematic Blood throughout the Porcine Estrone Estrous Cycle, Journal of Animal Science, vol. 57, pp. 449-455, ISU, 1983.
Manson, JoAnn E. et al., "Menopausal hormone therapy and health outcomes during the intervention and extended poststoping phases of the women's health initiative randomized trials," JAMA, Oct. 2, 2013, vol. 310, No. 13, pp. 1353-1368.

McGuffy, Irena, Softgel Technology as a Lipid-B1sed Delivery Tool for Bioavailability Enhancement, Catalent Pharma Solutions, Somerset, NJ, Mar. 2011.
Mesley, R.J., Clathrate Formation from Steroids, Chemistry and Industry, vol. 37 pp. 1594-1595, Sep. 1965.
Miao, Wenbin, et al., Chemical Properties of Progesterone, SciFinder, 2014, American Chemical Society & US Natl. Lib. of Med.
Miles et al., Pharmacokinetics and endometrial tissue levels of progesterone after administration bv'Intramuscular and vaginal routes: a comparative study, Fertility and Sterility, vol. 62, No. 3, Sep. 1994, pp. 485-490.
Miller et al., Safety and Feasibility of Topical Application of Limonene as a Massage Oil to the Breast, Journal of Cancer Therapy, 2012, 3, 749-754.
Mueck, A.O. et al., Genomic and non-genomic actions of progestogens in the breast, J. Steroid Biochem. Mol.Biol. (2013), Elsevier.
Muramatsu, Mitsuo, Thermodynamic Relationship between a- and B-Forms of Crystalline Progesterone, J. Pharmaceutical Sciences, vol. 68(2) pp. 175-178, 1979, Amer. Pharm. Assoc.
Ng, Jo-Han et al., Advances in biodiesel fuel for application in compression ignition engines, Clean Techn Environ Policy, vol. 12, pp. 459-493, 2010, Springer-Verlag.
Nicklas, Martina, Preparation and characterization of marine sponge collagen nanoparticles and employment for the trans . . . , Drug Devel. & Indust. Pharmacy,35(9) pp. 1035, 2009.
Nilsson et al., Analysis of Contact Allergenic Compounds in Oxidized d-Limonene, Chromatographia vol. 42, No. 3/4, Feb. 1996, pp. 199-205.
Notelovitz, Morris, et al., Initial 17-b-Estradiol Dose for Treating Vasomotor Symptoms, Obstetrics & Gynecology, vol. 95(5), pp. 726-731, part 1, May 2000, Elsevier.
NuGen, What is NuGen HP Hair Growth System.
NuGest900, NuGest 900™.
O'Leary, Peter, Salivary, but not serum or urinary levels of progesterone are elevated after topical application of pregersterone cream to pre-and post-menopausal women, Clinical Endocrinology, vol. 53 pp. 615-620, Blackwell Science 2000.
Opinion on the Diethylene Glycol Momoethyl Ether (DEGEE), Scientific Committee on Consumer Products, Dec. 19, 2006, 27 pages.
Outterson, K., The Drug Quality and Security Act—Mind the Gaps, n engl j med 370;2 nejm.org Jan. 9, 2014, pp. 97-99.
Palamakula et al., Preparation and In Vitro Characterization of Self-Nanoemulsified Drug Delivery Systems of Coenzyme Q10 Using Chiral Essential Oil Components, Pharmaceutical Technology Oct. 2004, pp. 74-88.
Panay et al., The 2013 British Menopause Society & Women's Health Concern recommendations on hormone replacement therapy, Menopause International: The Integrated Journal of Postreproductive Health, published online May 23, 2013, Sage Publications. http://min.sagepub.com/content/early/2013/05/23/1754045313489645.1.
Panchangnula et al., Development and evaluation of an intracutaneous depot formulation of corticosteroids using Transcutol . . . , J Pharm Pharmacol. Sep. 1991;43(9):609-614 (abstract only).
Parasuraman et al., Blood sample collection in small laboratory animals, Journal of Pharmacology & Pharmacotherapeutics | Jul.-Dec. 2010 | vol. 1 | Issue 2, pp. 87-93.
Park, Jeong-Sook, Solvent effects on physicochemical behavior of estradiols recrystalized for transdermal delivery, Arch Pharm Res, vol. 31(1), pp. 111-116, 2008.
Park, Jeong-Sook, Use of CP/MAS solid-state NMR for the characterization of solvate . . . , European Journal of Pharmaceutics and Biopharmaceutics, vol. 60, pp. 407-412, 2005.
Parrish, Damon A., A new estra-1,3,5(10)-triene-3,17b-diol solvate: estradiol-methanol-water, Crystal Structure Comm., Intn'l Union of Crystallography, ISSN 0108-2701, 2003.
Patel et al., Transdermal Drug Delivery System: A Review, www.thepharmajournal.com, vol. 1, No. 4, 2012, pp. 78-87.
Payne, R.S., et al., Examples of successful crystal structure prediction: polymorphs of primidone and progesterone, Intl. Jour. of Pharma., vol. 177 pp. 231-245, 1999, Elsevier.
PCCA, Apothogram, PCCA, May 2014, Houston, TX.

(56) References Cited

OTHER PUBLICATIONS

Persson, Linda C, et al., Physicochemical Properties of Progesterone Selecte, SciFinder, pp. 1-5, Feb. 24, 2014, American Chem. Society & US Natl. Lib. of Med.
Pfaus et al., Selective facilitation of sexual solicitation in the female rat by a melanocortin receptor agonist, PNAS, Jul. 6, 2004, vol. 101, No. 27, pp. 10201-10204.
Pheasant, Richard, Polymorphism of 17-Ethinylestradiol, Schering Corporation, Bloomfield, NJ, May 1950.
Pickles, VR, Cutaneous reactions to injection of progesterone solutions into the skin, Br Med Journal, Aug. 16, 1952, pp. 373-374.
Pinkerton et al., What are the concerns about custom-compounded "bioidentical" hormone therapy? Menopause: The Journal of The North American Menopause Society, vol. 21, No. 12, 2014,pp. 1-3.
Pinkerton, J.V., Thomas, S., Use of SERMs for treatment in postmenopausal women, J. Steroid Biochem. Mol. Biol. (2014), Elsevier.
Pisegna, Gisia L, A High-pressure Vibrational Spectroscopic Study of Polymorphism in Steroids . . . , Thesis, McGill University, Dept. of Chem, Nov. 1999, Natl. Lib. of Canada.
Portman, David et al., One-year treatment persistence with local estrogen therapy in postmenopausal women diagnosed as having vaginal atrophy, Menopause, vol. 22, No. 11, 2015, pp. 000/000 (8 pages).
Position Statement, Management of symptomatic vulvovaginal atrophy: 2013 position statement of the North American Menopause Society (NAMS), Menopause, vol. 20, No. 9, pp. 888-902.
Practice Bulletin No. 141, Management of Menopausal Symptoms, Obstetrics & Gynecology, ACOG, vol. 123, No. 1, Jan. 2014, pp. 202-216.
Prajapati Hetal N. et al., "A Comparative Evaluation of Mono-, Di- and Triglyceride of Medium Chain Fatty Acids by Lipid/Surfactant/Water Phase Diagram, Solubility Determination and Dispersion Testing for Application in Pharmaceutical Dosage Form Development," Pharm Res. Jan. 2012; 29(1): 285-305. Published online Aug. 23, 2011. doi: 10.1007/s11095-011-0541-3.
Prajapati Hetal N. et al., "Effect of Difference in Fatty Acid Chain Lengths of Medium-Chain Lipids on Lipid/Surfactant/Water Phase Diagrams and Drug Solubility," J. Excipients and Food Chem. 2 (3) 2011:73-88.
Prajapati, Hetal N, et al., A comparative Evaluation of Mono-, Di- and Triglyceride of Medium Chain Fatty Acids by Lipid/Surfactant/Water, Springerlink.com, pp. 1-21, Apr. 2011.
Prausnitz et al., Transdermal drug delivery, Nat Biotechnol. Nov. 2008 ; 26(11): 1261-1268.
Price, Sarah L, The computational prediction of pharmaceutical crystal structures and polymorphism, Adv. Drug Delivery Reviews, vol. 56 pp. 301-319, 2004, Elsevier.
Product Information Sheet, Body B1lance Cream, Tahitian Noni International, 2013, 1 page.
Product Safety Assessment: Diethylene Glycol Monoethyl Ether, Created: Sep. 24, 2007 The Dow Chemical Company Page, 5 pages.
Progesterone, The Merck Index Online, Royal Society of Chemistry, 2013, search Feb. 17, 2014 https://www.rsc.org/Merck-Index/monograph/print/mono1500007889/progesterone?q=authorize.
Progynova TS 100, available online at file:///C:/Users/Call%20Family/Desktop/Progynova%20TS%20100%2012%20Patches_Pack%20%28Estradiol%20Hemihydrate%29.html, 2010.
Provider Data Sheet, About Dried Blood Spot Testing, ZRT Laboratory, 2014, 3 pages.
Rahn et al., Vaginal Estrogen for Genitourinary Syndrome of Menopause A Systematic Review, Obstet Gynecol 2014;124(6):1147-56.
Rao, Rajeswara et al., "Intra Subject Variability of Progesterone 200 mg Soft Capsules in Indian Healthy Adult Postmenopausal Female Subjects under Fasting Conditions," J Bioequiv Availab. 2014, 6: 139-143.
Reisman et al., Topical Application of the Synthetic Triterpenoid RTA 408 Protects Mice from Radiation-Induced Dermatitis, Radiation Research 181, 512-520 (2014).
Rosilio, V, et al., Physical Aging of Progesterone-Loaded Poly(D,L,-lactide-co-glycolide) Microspheres, Pharmaceutical Research, vol. 15(5) pp. 794-799,1998, Plenum Pub. Corp.
Ross et al., Randomized, double-blind, dose-ranging study of the endometrial effects of a vaginal progesterone gel in estrogen-treated postmenopausal women, AnnJ Obstet Gynecol, Oct. 1997, vol. 177, No. 4, pp. 937-941.
Ruan et al., Systemic progesterone therapy—Oral, vaginal, injections and even transdermal? Maturitas 79 (2014) 248-255, Elsevier.
Salem, HF, Sustained-release progesterone nanosuspension following intramuscular injection in ovariectomized rats, International Journal of Nanomedicine 2010:5 943-954, Dove Press.
Sallee, Verney L. et al., "Determinants of intestinal mucosal uptake of short- and medium-chain fatty acids and alcohols," Journal of Lipid Research, 1973, vol. 14, 475-484.
Salole, Eugene G., Estradiol, Analytical Profiles of Drug Substances, vol. 15, pp. 283-318, 1986.
Salole, Eugene G., The physicochemical properties of oestradiol, Journal of Pharmaceutical & Biomedical Analysis, vol. 5, No. 7, pp. 635-648, 1987.
Santen, R.J., Menopausal hormone therapy and breast cancer, J. Steroid Biochem. Mol. Biol. (2013), Elsevier.
Santen, RJ, Vaginal administration of estradiol: effects of dose, preparation and timing on plasma estradiol levels, Climacteric 2014;17:1-14.
Sarkar, B1su, et al., Chemical Stability of Progesterone in Compounded Topical Preparations using PLO Transdermal Cream™ and HRT Cream™ B1se . . . , J Steroids Horm Sci, 4:2, 2013.
Sarpal, K. et al., "Self emulsifying drug delivery systems: a strategy to improve oral bioavailability," Current Research & Information on Pharmaceuticals Sciences (CRIPS), 2010, vol. 11, No. 3, pp. 42-49.
Sarrel, et al., The Mortality Toll of Estrogen Avoidance: An Analysis of Excess Deaths Among Hysterectomized Women Aged 50 to 59 Years, American Journal of Public Health, Research and Practice, e1-e6. Published online ahead of print Jul. 18, 2013.
Satyanarayana, D, et al., Aqueous Solubility Predictions of Aliphatic Alcohols, Alkyl Substituted Benzoates and Steroids, Asian J. Chem., vol. 9 (3) pp. 418-426, 1997.
Scavarelli, Rosa Maria, et al., Progesterone and Hydrate or Solvate, SciFinder, pp. 1-2, Feb. 24, 2014, American Chem. Society.
Schindler, A.E., The "newer" progestogens and postmenopausal hormone therapy (HRT), J. Steroid Biochem.Mol. Biol. (2013), Elsevier.
Schindler, Aldof E. et al., Classification and pharmacology of progestins, Maturitas 46S1 (2003) S7-S16.
Schutte et al., A tissue engineered human endometrial stroma that responds to cues for secretory differentiation, decidualization and menstruation, Fertil Steril. Apr. 2012 ; 97(4): 997-1003, Elsevier.
Schweikart et al., Comparative Uterotrophic Effects of Endoxifen and Tamoxifen in Ovariectomized Sprague-Dawley Rats, Toxicologic Pathology, 42: 1188-1196, 2014.
SciFinder Scholar Prednisone Chemical Properties, SciFinder, 2014, pp. 1-7, National Library of Medicine.
SciFinder Scholar Prednisone Physical Properties, SciFinder, 2014, pp. 1-10, Natioinal Library of Medicine.
SciFinder Scholar Progesterone Experimental Properties, SciFinder, pp. 1-9, Feb. 24, 2014, American Chem. Society.
Search Report, Extended European Search Report for EP13741053.6, dated Jul. 1, 2015.
Search Report, International Search Report for PCT/US12/66406, dated Jan. 24, 2013.
Search Report, International Search Report for PCT/US13/23309, dated Apr. 9, 2013.
Search Report, International Search Report for PCT/US13/46442, dated Nov. 1, 2013.
Search Report, International Search Report for PCT/US13/46443, dated Oct. 31, 2013.
Search Report, International Search Report for PCT/US13/46444, dated Oct. 31, 2013.
Search Report, International Search Report for PCT/US13/46445, dated Nov. 1, 2013.
Search Report, International Search Report for PCT/US14/61811, dated Jan. 21, 2015.

(56) References Cited

OTHER PUBLICATIONS

Search Report, International Search Report for PCT/US15/23041, dated Jun. 30, 2015.
Serantoni, Foresti, et al., 4-Pregnen-3,20-dione (progesterone, form II), Crystal Structure Comm., vol. 4(1) pp. 189-192, 1975, CAPLUS DataB1se.
Shao et al., Review Open Access Direct effects of metformin in the endometrium: a hypothetical mechanism for the treatment of women with PCOS and endometrial carcinoma, Journal of Experimental & Clinical Cancer Research 2014, 33(1):41, 11 pages.
Sharma, H.C., et al., Physical Properties of Progesterone Selected Refer, SciFinder, pp. 1-5, Feb. 24, 2014, American Chem. Society & US Natl. Lib. of Med.
Shrier et al., "Mucosal Immunity of the Adolescent Female Genital Tract," Journal of Adolescent Health, 2003; 32:183-186.
Shufelt et al., Hormone therapy dose, formulation, route delivery, and risk of cardiovascular events in women: findings from the Women's Health Initiative Observational Study, Menopause: The Journal of The North American Menopause Society, vol. 21, No. 3, 2014, pp. 1-7, 2013.
Siew, Adeline, moderator, Bioavailability Enhancement with Lipid-B1sed Drug-Delivery Systems, Pharmaceutical Technology, Aug. 2014, pp. 28, 30-31.
Sigma-Aldrich, Progesterone-Water Soluble: powder, BioReagent, suitable for cell culture), MSDS available online: http://www.sigmaaldrich.com/catalog/product/sigma/p7556.
Simon et al., Effective Treatment of Vaginal atrophy with an Ultra-low-dose estradiol vaginal tablet, Obstetrics & Gynocology, vol. 112, No. 5, Nov. 2008, pp. 1053-1060.
Simon, James A., What if the Women's Health Initiative had used transdermal estradiol and oral progesterone instead? Menopause: The Journal of The North American Menopause Society, 2014, vol. 21, No. 7, pp. 1-15.
Sitruk-Ware et al., Progestogens in hormonal replacement therapy: new molecules, risks, and benefits, Menopause: The Journal of The North American Menopause Society. vol. 9, No. 1, pp. 6-15, 2002.
Sitruk-Ware, Regine, "Pharmacological profile of progestins," Maturitas 47 (2004) 277-283.
Sitruk-Ware, Regine, Oral Micronized Progesterone—Bioavailability pharmacokinetics, pharmacological and therapeutic implications—A review, Contraception, Oct. 1987, vol. 36, No. 4, pp. 373-402.
Smith et al., Lower Risk of Cardiovascular Events in Postmenopausal Women Taking Oral Estradiol Compared with Oral Conjugated Equine Estrogens, JAMA Internal Medicine, Published online Sep. 30, 2013, E1-E7. jamainternalmedicine.com.
Smyth et al., Summary of Toxicological Data, a 2-Yr Study of Diethylene Glycol Monoethyl Ether in Rats, Fd Cosmet. Toxicol. vol. 2, pp. 641-642, 1964.
Stanczyk et al., Thereaputically equivalent pharmacokinetic profile across three application sistes for AG200-15, a novel low-estrogen dose contraceptive patch, Contraception, 87 (2013) pp. 744-749.
Stanczyk, F.Z. et al., "Percutaneous administration of progesterone: blood levels and endometrial protection," Menopause: The Journal of the North American Menopause Society, 2005, vol. 12, No. 2, pp. 232-237.
Stanczyk, F.Z. et al., Ethinyl estradiol and 17β-estradiol in combined oral contraceptives: pharmacokinetics, pharmacodynamics and risk assessment, Contraception 87 (Jun. 2013) vol. 87, No. 6, pp. 706-727.
Stanczyk, F.Z., "All progestins are not created equal," Steroids 68 (2003) 879-880.
Stanczyk, F.Z., "Treatment of postmenopausal women with topical progesterone creams and gels: are they effective?" Climacteric 2014;17 (Suppl 2):8-11.
Stanczyk, F.Z., Bhavnani, B.R., Current views of hormone therapy for the management and treatment of postmenopausal women, J. Steroid Biochem. Mol. Biol. (2014), Elsevier.
Stein, Emily A, et al., Progesterone Physical Properties, SciFinder, pp. 1-46, Feb. 24, 2014, American Chem. Society & US Natl. Lib. of Med.
Stephenson et al., "Transdermal progesterone: Effects on Menopausal symptoms and on thrombotic, anticoagulant, and inflammatory factors in postmenopausal women," Int J Pharmaceutical Compounding, vol. 12, No. 4, Jul./Aug. 2008, pp. 295-304.
Strickley, Robert T., Solubilizing excipients in oral and injectable formulations, Pharmaceutical Research Feb. 2004, vol. 21, Issue 2, pp. 201-230 (abstract only).
Strocchi, Antonino, Fatty Acid Composition, and Triglyceride Structure of Corn Oil, Hydrogenated Corn Oil, and Corn Oil Margarine, Journal of Food Science, vol. 47, pp. 36-39, 1981.
Struhar, M, et al., Estradiol Benzoate: Preparation of an injection suspension . . . , SciFinder, Cesko-Slovenska Farmacie, vol. 27(6), pp. 245-249, 1978, Bratislava, Czech.
Sullivan et al., "A review of the nonclinical safety of Transcutol®, a highly purified form of diethylene glycol monoethyl ether (DEGEE) used as a pharmaceutical excipient," Food and Chemical Toxicology, 72 (2014) pp. 40-50.
Sun, Jidong, D-Limonene: Safety and Clinical Applications, Alternative Medicine Review vol. 12, No. 3, 2007, pp. 259-264.
Tait, Alex D, Characterization of the Prod. from the Oxidation of Progesterone with Osmium Tetroxide, Dept of Investigative Med., Univ. Cambridge, Gt. Britain pp. 531-542, 1972.
Takacs M. et al., The light sensitivity of corticosteroids in crystalline form, Pharmaceutica acta Helvetiae, vol. 66 (5-6) pp. 137-140, 1991, Hardin Library.
Tan, Melvin S. et al., A Sensitive Method for the Determination of Progesterone in Human Plasma by LC-MS-MS, M1025, Cedra Corporation, Austin, Texas.
Tang et al., Effect of Estrogen and Progesterone on the Development of Endometrial Hyperplasia in the Fischer Rat, Biology of Reproduction 31, 399-413 (1984).
Tas et al., Comparison of antiproliferative effects of metformine and progesterone on estrogen-induced endometrial hyperplasia in rats, Gynecol Endocrinol, Early Online: 1-4, 2013. http://informahealthcare.com/gye.
Tella, S.H., Gallagher, J.C., Prevention and treatment of postmenopausal osteoporosis, J. Steroid Biochem. Mol. Biol. (2013), Elsevier.
Thomas, Joshua, et al., The effect of water solubility of solutes on their flux through human skin in vitro: An . . . , Intl. J. of Pharmaceut., vol. 339 pp. 157-167, 2007, Elsevier.
Thomas, Peter, Characteristics of membrane progestin receptor alpha (mPRα) and progesterone membrane receptor component 1 (PGMRC1) and their roles in mediating rapid progestin actions, Frontiers in Neuroendocrinology 29 (2008) 292-312.
Tripathi, R, et al., Study of Polymorphs of Progesterone by Novel Melt Sonocrystallization Technique: A Technical Note, AAPS PhamSciTech, vol. 11, No. 3, Sep. 2010.
Trommer et al., Overcoming the stratum Corneum: The modulation of Skin Penetration, Skin Pharmacol Physiol 2006;19:106-121.
Tuleu et al., "Comparative Bioavailability Study in Dogs of a Self-Emulsifying Formulation of Progesterone Presented in a Pellet and Liquid Form Compared with an Aqueous Suspension of Progesterone," Journal of Pharmaceutical Sciences, vol. 93, No. 6, Jun. 2004, pp. 1495-1502.
Ueda et al., Topical and Transdermal Drug Products, Pharmacopeial Forum, vol. 35(3) [May-Jun. 2009], 750-754.
USP, 401 Fats and Fixed Oils, Chemical Tests, Second Suplement to USP36-NF 31, pp. 6141-6151, 2013.
USP, Certificate—Corn Oil, Lot G0L404, Jul. 2013.
USP, Lauroyl Polyoxylglycerides, Safety Data Sheet, US, 5611 Version #02, pp. 1-9, 2013.
USP, Monographs: Progesterone, USP29, www.pharmacopeia.cn/v29240/usp29nf24s0_m69870.html, search done: Feb. 25, 2014.
USP, Official Monographs, Corn Oil, NF 31, pp. 1970-1971, Dec. 2013.
USP, Official Monographs, Lauroyl Polyoxylglycerides, NF 31, pp. 2064-2066, Dec. 2013.
USP, Official Monographs, Medium Chain Triglycerides, NF 31, pp. 2271-2272, Dec. 2013.

(56) References Cited

OTHER PUBLICATIONS

USP, Official Monographs, Mono- and Di-glycerides, NF 31, pp. 2101, Dec. 2013.
U.S. Appl. No. 13/843,428 Jul. 2, 2015 Non-Final Office Action.
U.S. Appl. No. 14/106,655 Jun. 19, 2015 Final Office Action.
U.S. Appl. No. 12/561,515_Dec. 12, 2011 Office Action.
U.S. Appl. No. 12/561,515_Oct. 26, 2012 Final Office Action.
U.S. Appl. No. 12/561,515_Jan. 29, 2013_Advisory_Action.
U.S. Appl. No. 12/561,515_Sep. 11, 2013 Notice of Allowance.
U.S. Appl. No. 13/684,002_Mar. 20, 2013_Non-Final_Office_Action.
U.S. Appl. No. 13/684,002_Jul. 16, 2013_Final_Office_Action.
U.S. Appl. No. 13/684,002_Dec. 6, 2013_Notice_of_Allowance.
U.S. Appl. No. 13/843,362_Mar. 16, 2015_Restriction_Requirement.
U.S. Appl. No. 13/843,428_Apr. 14, 2015_Restriction_Requirement.
U.S. Appl. No. 14/099,545_Feb. 18, 2014_Non-Final_Office_Action.
U.S. Appl. No. 14/099,545_Jul. 14, 2014_Notice_of_Allowance.
U.S. Appl. No. 14/099,562_Feb. 20, 2014_Restriction_Requirement.
U.S. Appl. No. 14/099,562_Mar. 27, 2014_Non-Final_Office_Action.
U.S. Appl. No. 14/099,562_Jul. 2, 2014_Final_Office_Action.
U.S. Appl. No. 14/099,562_Dec. 10, 2014_Notice_of_Allowance.
U.S. Appl. No. 14/099,571_Mar. 28, 2014_Restriction_Requirement.
U.S. Appl. No. 14/099,571_Jul. 15, 2014_Notice_of_Allowance.
U.S. Appl. No. 14/099,582_Apr. 29, 2014_Restriction_Requirement.
U.S. Appl. No. 14/099,582_Jun. 17, 2014_Non-Final_Office_Action.
U.S. Appl. No. 14/099,582_Nov. 7, 2014_Notice_of_Allowance.
U.S. Appl. No. 14/099,582_Jan. 22, 2015_Notice_of_Allowance.
U.S. Appl. No. 14/099,598_May 13, 2014_Restriction_Requirement.
U.S. Appl. No. 14/099,598_Jul. 3, 2014_Non-Final_Office_Action.
U.S. Appl. No. 14/099,598_Dec. 10, 2014_Notice_of_Allowance.
U.S. Appl. No. 14/099,612_Mar. 20, 2014_Restriction_Requirement.
U.S. Appl. No. 14/099,612_Oct. 30, 2014_Non-Final_Office_Action.
U.S. Appl. No. 14/099,612_Nov. 26, 2014_Notice_of_Allowance.
U.S. Appl. No. 14/099,623_Mar. 5, 2014_Restriction_Requirement.
U.S. Appl. No. 14/099,623_Jul. 18, 2014_Non-Final_Office_Action.
U.S. Appl. No. 14/099,623_Dec. 15, 2014_Notice_of_Allowance.
U.S. Appl. No. 14/106,655_Jul. 3, 2014_Restriction_Requirement.
U.S. Appl. No. 14/106,655_Dec. 8, 2014_Non-Final_Office_Action.
U.S. Appl. No. 14/125,554_Dec. 5, 2014_Restriction_Requirement.
U.S. Appl. No. 14/125,554_Apr. 14, 2015_Non-Final_Office_Action.
U.S. Appl. No. 14/136,048_Nov. 4, 2014_Restriction_Requirement.
U.S. Appl. No. 14/136,048_Mar. 12, 2015_Non-Final_Office_Action.
U.S. Appl. No. 14/475,814_Oct. 1, 2014_Non-Final_Office_Action.
U.S. Appl. No. 14/475,814_Feb. 13, 2015_Notice_of_Allowance.
U.S. Appl. No. 14/475,864_Oct. 2, 2014_Non-Final_Office_Action.
U.S. Appl. No. 14/475,864_Feb. 11, 2015_Notice_of_Allowance.
U.S. Appl. No. 14/476,040_Mar. 26, 2015_Restriction_Requirement.
U.S. Appl. No. 14/521,230_Dec. 5, 2014_Restriction_Requirement.
U.S. Appl. No. 14/521,230_Feb. 18, 2015_Non-Final_Office_Action.
U.S. Appl. No. 14/624,051_Apr. 7, 2015_Non-Final_Office_Action.
Utian, Wulf H, et al., Relief of vasomotor symptoms and vaginal atrophy with lower doses of conjugated equine estrogens, Fertility and Sterility, vol. 75(6) pp. 1065, Jun. 2001.
Voegtline et al., Dispatches from the interface of salivary bioscience and neonatal research, Frontiers in Endocrinology, Mar. 2014, vol. 5, article 25, 8 pages.
Waddell et al., Distribution and metabolism of topically applied progesterone in a rat model, Journal of Steroid Biochemistry & Molecular Biology 80 (2002) 449-455.
Waddell et al., The Metabolic Clearance of Progesterone in the Pregnant Rat: Absence of a Physiological Role for the Lung, Biology of Reproduction 40, 1188-1193 (1989).

Walter et al., The role of progesterone in endometrial angiogenesis in pregnant and ovariectomised mice, Reproduction (2005) 129 765-777.
Weber, E.J., Corn Lipids, Cereal Chem., vol. 55(5), pp. 572-584, The American Assoc of Cereal Chem, Sep.-Oct. 1978.
Weber, M.T., et al., Cognition and mood in perimenopause: A systematic review and meta-analysis, J. Steroid Biochem. Mol. Biol. (2013), Elsevier.
Weintraub, Arlene, "Women fooled by untested hormones from compounding pharmacies,"Forbes, Feb. 20, 2015; retrieved online at http://onforb.es/1LIUm1V_on Feb. 23, 2015, 3 pages.
Whitehead et al., Absorption and metabolism of oral progesterone, The British Medical Journal, vol. 280, No. 6217 (Mar. 22, 1980), pp. 825-827, BMJ Publishing Group.
Wiranidchapong, Chutima, Method of preparation does not affect the miscibility between steroid hormone and polymethacrylate, Thermochimica Acta 485, Elsevier, pp. 57, 2009.
Wood et al., Effects of estradiol with micronized progesterone or medroxyprogesterone acetate on risk markers for breast cancer in postmenopausal monkeys, Breast Cancer Res Treat (2007) 101:125-134.
Wren et al., Effect of sequential transdermal progesterone cream on endometrium, bleeding pattern, and plasma progesterone and salivary progesterone levels in postmenopausal women, Climacteric, 2000, 3(3), pp. 155-160. http://dx.doi.org/10.1080/13697130008500109.
Wu et al., Gene Expression Profiling of the Effects of Castration and Estrogen Treatment in the Rat Uterus, Biology of Reproduction 69, 1308-1317 (2003).
Yalkowsky, Samuel H, & Valvani, Shri C, Solubility and Partitioning I: Solubility of Nonelectrolytes in Water, J. of Pharmaceutical Sciences, vol. 69(8) pp. 912-922, 1980.
Yalkowsky, Samuel H, Handbook of Acqueous Solubility Data, Solutions, pp. 1110-1111, CRC PRESS, Boca Raton, London, New York, Wash. D.C.
Yue, W., Genotoxic metabolites of estradiol in breast: potential mechanism of estradiol induced carcinogenesis, Journal of Steroid Biochem & Mol Biology, vol. 86 pp. 477-486, 2003.
Zava, David T. et al., Percutaneous absorption of progesterone, Maturitas 77 (2014) 91-92, Elsevier.
Zava, David T., Topical Progesterone Delivery and Levels in Serum, Saliva, Capillary Blood, and Tissues, Script, ZRT Laboratory, pp. 4-5. http://www.zrtlab.com/component/docman/cat_view/10-publications?Itemid.
U.S. Appl. No. 13/684,002, filed Nov. 21, 2012, U.S. Pat. No. 8,633,178, Jan. 21, 2014.
U.S. Appl. No. 13/843,362, filed Mar. 15, 2013.
U.S. Appl. No. 13/843,428, filed Mar. 15, 2013.
U.S. Appl. No. 14/099,545, filed Dec. 6, 2013, U.S. Pat. No. 8,846,648, Sep. 30, 2014.
U.S. Appl. No. 14/099,562, filed Dec. 6, 2013, U.S. Pat. No. 8,987,237, Mar. 24, 2015.
U.S. Appl. No. 14/099,571, filed Dec. 6, 2013, U.S. Pat. No. 8,846,649, Sep. 30, 2014.
U.S. Appl. No. 14/099,582, filed Dec. 6, 2013, U.S. Pat. No. 9,012,434, Apr. 21, 2015.
U.S. Appl. No. 14/099,598, filed Dec. 6, 2013, U.S. Pat. No. 8,987,238, Mar. 24, 2015.
U.S. Appl. No. 14/099,612, filed Dec. 6, 2013, U.S. Pat. No. 8,933,059, Jan. 13, 2015.
U.S. Appl. No. 14/099,623, filed Dec. 6, 2013, U.S. Pat. No. 9,006,222, Apr. 14, 2015.
U.S. Appl. No. 14/125,547, filed Dec. 11, 2013.
U.S. Appl. No. 14/125,554, filed Dec. 12, 2013.
U.S. Appl. No. 14/106,655, filed Dec. 13, 2013.
U.S. Appl. No. 14/136,048, filed Dec. 20, 2013.
U.S. Appl. No. 14/475,814, filed Sep. 3, 2014, U.S. Pat. No. 8,993,548, Mar. 31, 2015.
U.S. Appl. No. 14/475,864, filed Sep. 3, 2014, U.S. Pat. No. 8,993,549, Mar. 31, 2015.
U.S. Appl. No. 14/475,946, filed Sep. 3, 2014, U.S. Pat. No. 9,114,145, Aug. 25, 2015.
U.S. Appl. No. 14/476,040, filed Sep. 3, 2014, U.S. Pat. No. 9,114,146, Aug. 25, 2015.

(56) References Cited

OTHER PUBLICATIONS

U.S. Appl. No. 14/521,002, filed Oct. 22, 2014.
U.S. Appl. No. 14/521,230, filed Oct. 22, 2014.
U.S. Appl. No. 14/645,661, filed Mar. 12, 2015.
U.S. Appl. No. 14/690,913, filed Apr. 20, 2015.
U.S. Appl. No. 14/690,955, filed Apr. 20, 2015.
Holm et al., "Examination of oral absorption and lymphatic transport of halofantrine in a triple-cannulated canine model after administration in self-microemulsifying drug delivery systems (SMEDDS) containing structured triglycerides," European Journal of Pharmaceutical Sciences, 2003, 20:91-97.
Hitchcock, Christine L. et al., "Oral micronized progesterone for vasomotor symptoms—a placebo-controlled randomized trial in healthy postmenopausal women," Menopause: The Journal of the North American Menopause Society. 19(8):886-893, Aug. 2012.
Hosmer, Jaclyn et al., "Microemulsions Containing Medium-Chain Glycerides as Transdermal Delivery Systems for Hydrophilic and Hydrophobic Drugs," AAPS Pharm Sci Tech, 2009, vol. 10, No. 2, pp. 589-596.
Castelo-Branco Camil et al., "Treatment of atrophic vaginitis," Therapy, 2007, vol. 4, No. 3, pp. 349-353.
Cho, Y.A. et al., Transdermal Delivery of Ketorolac Tromethamine: Effects of Vehicles and Penetration Enhancers, Drug Development and Industrial Pharmacy, 30(6):557-564, Jun. 2004.
Cicinelli et al., "First uterine pass effect" is observed when estradiol is placed in the upper but not lower third of the vagina, Fertility and Sterility, vol. 81, No. 5, May 2004, pp. 1414-1416.
Cicinelli, Intravaginal oestrogen and progestin administration: advantages and disadvantages, Best Practices & Research Clinical Obstretrics and Gynaecology vol. 22, No. 2, 2008, pp. 391-405.
Crandall, Carolyn, "Vaginal Estrogen Preparations: A Review of Safety and Efficacy for Vaginal Atrophy," Journal of Women's Health, 2002, vol. 11, No. 10, pp. 857-877.
Cremer Care, ""MIGLYOL® 810, 812 INCI: Caprylic/Capric Triglyceride,"" Cremer Oleo GmbH & Co. KG, pp. 1-7, available at http://s3.amazonaws.com/petercremerna/products/spec_sheets/159/339/301 /originai/M IGLYOL_81 0_812_ TDS.pdf?1389204445 (Mar. 2013) accessed on Dec. 30, 2016.
Ettinger et al., "Measuring symptom relief in studies of vaginal and vulvar atrophy: the most bothersome symptom approach," Menopause, vol. 15, No. 5, 2008, pp. 885-889.
Eugster-Hausmann et al., "Minimized estradiol absorption with ultra-low-dose 10 μg 17β-estradiol vaginal tablets," Climacteric 2010;13:219-227.
Garad S. et al., "Preclinical Development for Suspensions," A.K. Kulshreshtha et al. (eds.), Pharmaceutical Suspensions: From Formulation Development to Manufacturing, Springer, New York 2010, pp. 127-176.
Karande, et al., Enhancement of transdermal drug delivery via synergistic action of chemicals, Biochimica et Biophysica Acta, 1788:2362-2373, Sep. 2009.
Knuth et al., Hydrogel delivery systems for vaginal and oral applications: Formulation and biological considerations, Advanced Drug Delivery Reviews, vol. 11, No. 1-2, Jul.-Aug. 1993, pp. 137-167.
Lopes, Luciana B. et al., Enhancement of transdermal delivery of progesterone using medium-chain mono and diglycerides as skin penetration enhancers, Pharmaceutical Development and Technology, 14:5, 524-529, Mar. 2009.

Mac Bride, Maire B. et al., "Vulvovaginal Atrophy," Mayo Clin Proc, Jan. 2010, 85(1):87-94.
March, Charles M. et al., "Roles of Estradiol and Progesterone in Eliciting the Midcycle Luteinizing Hormone and Follicle-Stimulating Hormone Surges," The Journal of Clinical Endocrinology & Metabolism, vol. 49, Issue 4, Oct. 1, 1979, pp. 507-513.
Martelli, Mary Elizabeth, "Vaginal Medicine Administration," The Gale Encyclopedia of Nursing and Allied Health, Gale Group, 2002, pp. 2542-2543.
Monti, D. et al., Effect of different terpene-containing essential oils on permeation of estradiol through hairless mouse skin, International Journal of Pharmaceutics, 237:209-24, 2002.
Pachman et al., "Management of menopause-associated vasomotor symptoms: Current treatment options, challenges and future directions," International Journal of Women's Health, May 7, 2010.
Potluri, Praveen and Guru V. Betageri, "Mixed-micellar proliposomal systems for enhanced oral delivery of progesterone," Drug Delivery, 2006, vol. 13, No. 3, pp. 227-232.
Rao, R. et al., "The Affect of Capmul, Labrafil and Transcutol on Progesterone 100 Mg Soft Capsules Bioavailability in Indian Healthy Adult Postmenopausal Female Subjects Under Fasting Conditions," Bioequivalence & Bioavailability, 7(2):095-107, 2015.
Regidor, P., "Progesterone in Peri- and Postmenopause: A Review," Geburtshilfe Frauenheilkd, Nov. 2014 74(11):995-1002.
Simon, James A. et al., "A vaginal estradiol softgel capsule, TX-004HR, has negligible to verylow systemic absorption of estradiol: Efficacy and pharmacokineticdata review," Maturitas 99 (2017) 51-58.
Sofi, Showkat Hussain et al., "Gelucire: A Versatile Formulation Excipient," Ijppr.Human, 2017; vol. 10 (3): 55-73.
Stefanick, "Estrogens and progestins: background and history, trends in use, and guidelines and regimens approved by the US Food and Drug Administration," The American Journal of Medicine (2005) vol. 118 (12B), 64S-73S.
Activella Label, Revised Nov. 2015 and Nov. 2017, 39 pages.
Cicinelli et al., "Placement of the vaginal 17β-estradiol tablets in the inner or outer one third of the vagina affects the preferential delivery of 17β-estradiol toward the uterus or periurethral areas, thereby modifying efficacy and endometrial safety," Am J Obstet Gynocol, vol. 189, No. 1, Jul. 2003, pp. 55-58.
Khera, M. "Testosterone Therapy for Female Sexual Dysfunction," Sex Med Rev, Jul. 2015; 3(3):137-144.
Kingsberg et al., "Treating dyspareunia caused by vaginal atrophy: a review of treatment options using vaginal estrogen therapy," Int J Womens Health 2009; 1: 105-111.
Mirkin, S. et al., "17β-Estradiol and natural progesterone for menopausal hormone therapy: Replenish phase 3 study design of a comnbination capsule and evidence review," Maturitas, vol. 81, No. 1, 2015, pp. 28-35.
Prometrium Label, Jun. 2009, 33 pages.
Tang et al., "Pharmacokinetics of different routes of administration of misoprostol," Human Reproduction, 2002; 17(2):332-226.
Vagifem Label, Nov. 2009, 14 pages.
Wang et al., "Pharmacokinetics of hard micronized progesterone capsules via vaginal or oral route compared with soft micronized capsules in healthy postmenopausal women: a randomized open-label clinical study," Drug Des Devel Ther., 2019; 13: 2475-2482.

* cited by examiner

95% Confidence Interval for PK Parameter

| Parameter | Point estimate T/R Ratio | Within Subject Std. Deviation | Upper 95% Confidence Bound |
|---|---|---|---|
| $C_{max}$ | 0.88 | 0.344 | -0.040 |
| $AUC_{0-1}$ | 0.93 | 0.409 | -0.089 |

NATURAL COMBINATION HORMONE REPLACEMENT FORMULATIONS AND THERAPIES

CROSS-REFERENCE TO RELATED APPLICATIONS

This application is a continuation-in-part of U.S. patent application Ser. No. 13/843,428, filed on Mar. 15, 2013, which is a continuation-in-part of U.S. application Ser. No. 13/684,002, filed on Nov. 21, 2012, which claims priority to U.S. Provisional Application Ser. No. 61/661,302, filed on Jun. 18, 2012, and to U.S. Provisional Application Ser. No. 61/662,265, filed on Jun. 20, 2012; and also claims priority to U.S. Provisional Application Ser. No. 61/889,483, filed Oct. 10, 2013; the contents of each of which are incorporated by reference herein in their entirety.

FIELD OF THE INVENTION

This application relates to natural estrogen and progesterone replacement therapies, with formulations provided for each estradiol and progesterone alone and in combination for the treatment of pre, peri-menopausal, menopausal and post-menopausal females in relation to the treatment of Estrogen- and Progesterone-deficient states, each as herein below defined.

BACKGROUND OF THE INVENTION

Hormone Replacement Therapy (HRT) is a medical treatment that involves the use of one or more of a group of medications designed to increase hormone levels in women who lack adequate hormone production. HRT can mitigate and prevent symptoms caused by diminished circulating estrogen and progesterone hormones regardless as to whether the subject is pre-menopausal, peri-menopausal, menopausal or post-menopausal. However, specific symptomatic states can exist during each stage of menopausal progression.

HRT is presently available in various forms. One therapy involves administration of low dosages of one or more estrogens. Another involves administration of progesterone or a chemical analogue, called a progestin. Progesterone administration acts, among treating other disease states, to mitigate certain undesirable side effects from estrogen administration including, for example, endometrial hyperplasia (thickening) and reducing the incidence of endometrial cancer.

Timing for dosage administration is often varied cyclically, with estrogens taken daily and progesterone taken for approximately two weeks of every month; a method often referred to as "Cyclic-Sequential" or "Sequentially-Combined HRT." This method is intended to mimic the natural menstrual cycle and typically causes menstruation similar to a period after the progesterone is stopped. This regimen is most typically used in peri-menopausal or newly menopausal women as the alternative continuous method often results in irregular bleeding in such women. An alternate method, a constant dosage with both estrogen and progesterone taken daily, is called "Continuous-Combined HRT." This method usually results in no menstruation and is used most often after a woman has been menopausal for some time.

Estrogen, in its various forms, and progesterone, in its various forms, are used in HRT via a variety of administered dosage forms including, for example, via tablets, capsules and patches.

"Bio-identical" or "body-identical" hormones, which are identical in chemical structure to the hormones naturally produced by human bodies, can be used and are often referred to as Natural Hormone Replacement Therapy, or NHRT.

These natural or bio-identical hormones are formulated from various ingredients to match the chemical structure and effect of estradiol, estrone, or estriol (the 3 primary estrogens) as well as progesterone that occurs naturally in the human body (endogenous).

Currently, bio-identical estradiol is available in both branded and generic FDA approved versions. FDA-approved bio-identical progesterone for HRT is available as the branded stand-alone drug commercially identified as PROMETRIUM® (progesterone, USP) (Abbott Laboratories, Abbott Park, Ill.), with a generic authorized by the innovator, and generic products provided by Teva (Israel) and Sofgen Americas, Inc. (New York). PROMETRIUM® was approved for sale in the United States on May 14, 1998 under NDA # N019781. According to the prescribing information approved for this product (Rev June 2009) ("PROMETRIUM® prescribing information"), PROMETRIUM® comprises synthetic progesterone that is chemically identical to progesterone of human ovarian origin. Capsules comprise 100 mg or 200 mg of micronized progesterone. The inactive ingredients include peanut oil, gelatin, glycerin, lecithin, titanium dioxide, and yellow and red dyes.

Other products such as PREMPRO® (conjugated estrogens/medroxyprogesterone acetate tablets) and PREMPHASE® (conjugated estrogens plus medroxyprogesterone acetate tablets) (Wyeth Laboratories, a division of Pfizer, Inc., New York) provide both continuous-combined and cyclic-sequential products containing PREMARIN® (estrogen derived from mare's urine) and synthetic medroxyprogesterone acetate. Other products are available. However, no FDA approved product exists on the market today with combination bio-identical estradiol and bio-identical progesterone.

BRIEF SUMMARY OF THE INVENTION

In one aspect, pharmaceutical formulations for co-administering estradiol and progesterone to a mammal in need thereof are provided. In some embodiments, the pharmaceutical formulation comprises: solubilized estradiol, suspended progesterone, and a medium chain (C6 to C12) oil.

In some embodiments, the medium chain oil comprises medium chain fatty acid esters of glycerol, polyethylene glycol, or propylene glycol, or mixtures thereof, wherein the medium chain fatty acids are predominantly: C6 to C12 fatty acids, C6 to C10 fatty acids, C8 to C12 fatty acids, or C8 to C10 fatty acids. In some embodiments, the medium chain oil comprises a glyceride containing a C6-C12 fatty acid. In some embodiments, the glyceride is a mixture of mono- and diglycerides. In some embodiments, the fatty acid is predominantly a C8 to C10 fatty acid. In some embodiments, the fatty acids are predominantly saturated fatty acids. In some embodiments, the fatty acids are predominantly unsaturated fatty acids. In some embodiments, the medium chain oil comprises CAPMUL® MCM.

In some embodiments, the pharmaceutical formulation further comprises one or more surfactants, e.g., one or more non-ionic surfactants. In some embodiments, the surfactant comprises lauroyl polyoxyl-32-glycerides. In some embodiments, the surfactant comprises GELUCIRE® 44/14.

In some embodiments, the pharmaceutical formulation further comprises solubilized progesterone, wherein at least 50% (e.g., at least 50%, at least 60%, at least 70%, at least 80%, at least 90%, or about 100%) of the total progesterone is solubilized.

In some embodiments, the pharmaceutical formulation is in a hard capsule, a soft capsule, or a tablet for oral administration. In some embodiments, the hard capsule or soft capsule comprises gelatin, glycerol, and coloring agents.

In some embodiments, the pharmaceutical formulation comprises:
 30 to 35 wt % progesterone;
 0.1 to 0.4 wt % estradiol;
 55 to 75 wt % medium chain oil; and
 0.5 to 10 wt % non-ionic surfactant.

In some embodiments, the pharmaceutical formulation comprises about 2 mg estradiol and about 200 mg progesterone.

In some embodiments, a pharmaceutical formulation as described herein (e.g., comprising solubilized estradiol, suspended progesterone, and a medium chain (C6-C12) oil), when administered to a human subject, produces:

(a) one or more progesterone-related parameters selected from: (i) an area under the curve $(AUC)_{(0-t)}$ for progesterone that is from 96 ng·hr/ml to 150 ng·hr/ml; (ii) an $AUC_{(0-\infty)}$ for progesterone that is from 105 ng·hr/ml to 164 ng·hr/ml; and (iii) a $C_{max}$ for progesterone that is from 71 ng/ml to 112 ng/ml; and (b) one or more estrogen-related parameters selected from: (i) an $AUC_{(0-t)}$ for estradiol that is from 1123 pg·hr/ml to 1755 pg·hr/ml; (ii) an $AUC_{(0-\infty)}$ for estradiol that is from 1968 pg·hr/ml to 3075 pg·hr/ml; and (iii) a $C_{max}$ for unconjugated estradiol that is from 52 pg/ml to 81 pg/ml.

In some embodiments, administration of the formulation to the subject produces both an $AUC_{(0-t)}$ for progesterone that is from 96 ng·hr/ml to 150 ng·hr/ml and a $C_{max}$ for progesterone that is from 71 ng/ml to 112 ng/ml. In some embodiments, administration of the formulation to the subject produces both an $AUC_{(0-t)}$ for unconjugated estradiol that is from 1123 pg·hr/ml to 1755 pg·hr/ml and a $C_{max}$ for unconjugated estradiol that is from 52 pg/ml to 81 pg/ml.

In some embodiments, when the formulation is administered to a human subject, the formulation further produces one or more of the following:
 (i) an $AUC_{(0-t)}$ for estrone sulfate that is from 7277 pg·hr/ml to 11370 pg·hr/ml;
 (ii) an $AUC_{(0-\infty)}$ for estrone sulfate that is from 9596 pg·hr/ml to 14994 pg·hr/ml; or
 (iii) a $C_{max}$ for estrone sulfate that is from 341 pg/ml to 533 pg/ml.

In some embodiments, administration of the formulation to the subject produces both an $AUC_{(0-t)}$ for estrone sulfate that is from 7277 pg·hr/ml to 11370 pg·hr/ml and a $C_{max}$ for estrone sulfate that is from 341 pg/ml to 533 pg/ml.

In some embodiments, when the formulation is administered to a human subject, the formulation further produces one or more of the following:
 (i) an $AUC_{(0-t)}$ for total estrone that is from 161 pg·hr/ml to 252 pg·hr/ml;
 (ii) an $AUC_{(0-\infty)}$ for total estrone that is from 171 pg·hr/ml to 267 pg·hr/ml; or
 (iii) a $C_{max}$ for total estrone that is from 28 pg/ml to 44 pg/ml.

In some embodiments, administration of the formulation to the subject produces both an $AUC_{(0-t)}$ for total estrone that is from 161 pg·hr/ml to 252 pg·hr/ml and a $C_{max}$ for total estrone that is from 28 pg/ml to 44 pg/ml.

In some embodiments, the progesterone and the estradiol in the pharmaceutical formulation demonstrate comparable bioavailability to their individual drug references of PROMETRIUM® and ESTRACE®, respectively ("Referenced Products"), when said formulation is administered to a human subject.

In some embodiments, the progesterone and the estradiol in said formulation demonstrate about 80% to about 125% of the $C_{max}$ and/or AUC of their individual references of PROMETRIUM® and ESTRACE®, respectively, when said formulation is administered to a human subject.

In some embodiments, when administered to a human subject, the formulation produces one or more of the following:
 (i) an $AUC_{(0-t)}$ for progesterone comparable to the $AUC_{(0-t)}$ for progesterone obtained with PROMETRIUM®;
 (ii) an $AUC_{(0-\infty)}$ for progesterone comparable to the $AUC_{(0-\infty)}$ for progesterone obtained with PROMETRIUM®; or
 (iii) a $C_{max}$ for progesterone comparable to the $C_{max}$ for progesterone obtained with PROMETRIUM®.

In some embodiments, when administered to a human subject, the formulation produces one or more of the following:
 (i) an $AUC_{(0-t)}$ for unconjugated estradiol comparable to the $AUC_{(0-t)}$ for progesterone obtained with ESTRACE®;
 (ii) an $AUC_{(0-\infty)}$ for unconjugated estradiol comparable to the $AUC_{(0-\infty)}$ for progesterone obtained with ESTRACE®; or
 (iii) a $C_{max}$ for unconjugated estradiol comparable to the $C_{max}$ for progesterone obtained with ESTRACE®.

In some embodiments, when administered to a human subject, the formulation produces one or more of the following:
 (i) an $AUC_{(0-t)}$ for unconjugated estrone comparable to the $AUC_{(0-t)}$ for progesterone obtained with ESTRACE®;
 (ii) an $AUC_{(0-\infty)}$ for unconjugated estrone comparable to the $AUC_{(0-\infty)}$ for progesterone obtained with ESTRACE®; or
 (iii) a $C_{max}$ for unconjugated estrone comparable to the $C_{max}$ for progesterone obtained with ESTRACE®.

In some embodiments, when administered to a human subject, the formulation produces one or more of the following:
 (i) an $AUC_{(0-t)}$ for total estrone comparable to the $AUC_{(0-t)}$ for progesterone obtained with ESTRACE®; or
 (ii) an $AUC_{(0-\infty)}$ for total estrone comparable to the $AUC_{(0-\infty)}$ for progesterone obtained with ESTRACE®.

In another aspect, methods of treating a subject having one or more symptoms of estrogen deficiency (e.g., one or more symptoms of menopause) are provided. In some embodiments, the method comprising administering to the subject an effective amount of a pharmaceutical formulation as described herein. In some embodiments, the subject is female. In some embodiments, the subject is a woman having a uterus.

In yet another aspect, methods of effecting hormone replacement therapy in a woman in need thereof are provided. In some embodiments, the method comprises orally administering to the woman an effective amount of a pharmaceutical formulation as described herein.

BRIEF DESCRIPTION OF THE DRAWINGS

The accompanying drawings, which are incorporated herein and form a part of the specification, illustrate the present disclosure and, together with the description, further serve to explain the principles of the disclosure and to enable a person skilled in the pertinent art to make and use the disclosed embodiments.

DETAILED DESCRIPTION OF THE INVENTION

Figure 1:
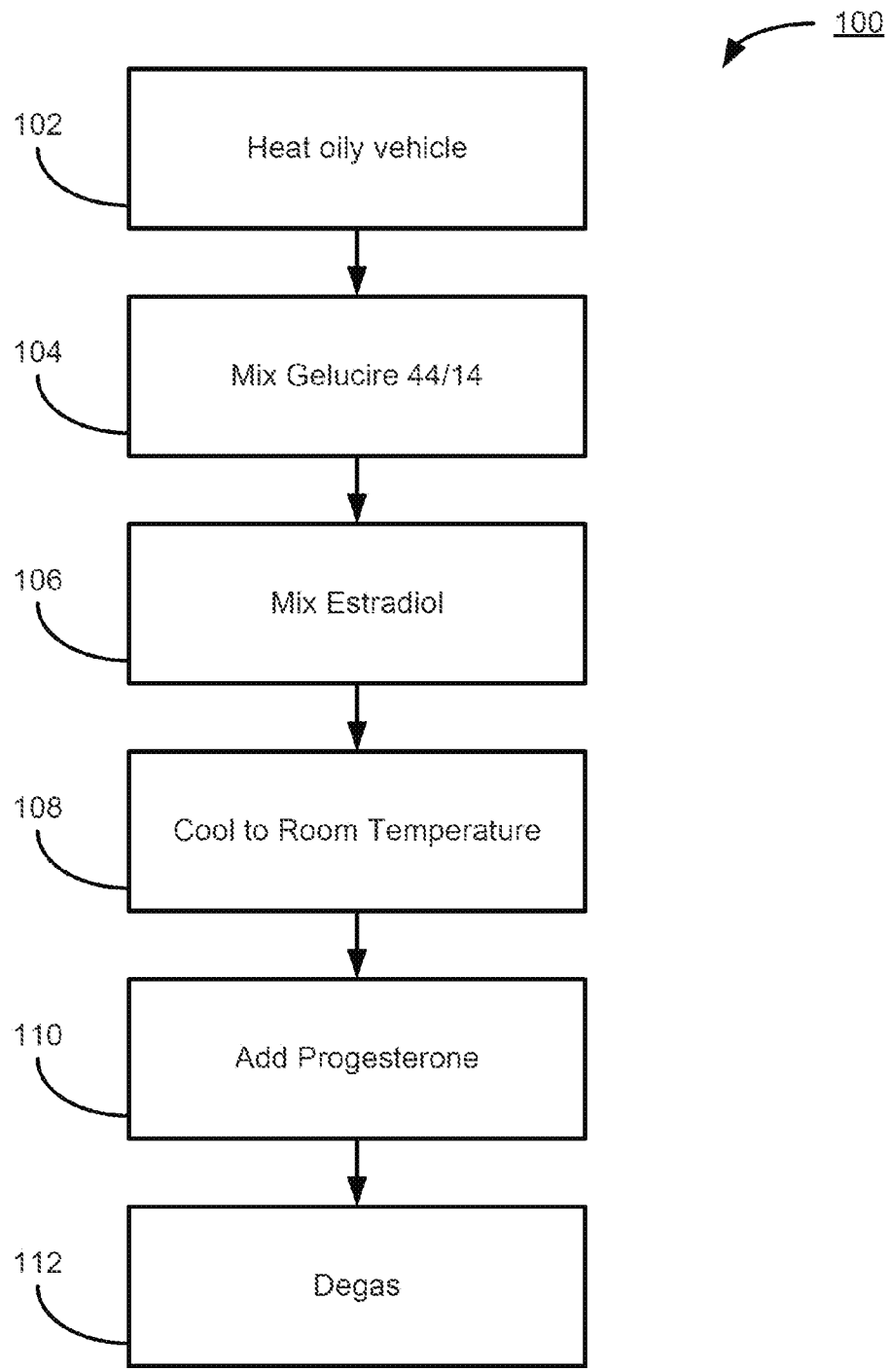
FIG. 1 illustrates an exemplary manufacturing process of a fill material in accordance with various embodiments of the invention.

Frequently, higher recommended oral dosages of pharmaceuticals are necessary to treat a given disease state because many active ingredients are not completely absorbed by a patient in need of treatment. In other words, a better-absorbed dosage form of a medicament such as, for example, progesterone or estradiol, or dosage forms that provide greater consistency of absorption of progesterone or estradiol among subjects, alone or in combination with estradiol, may be able to be administered at dosage strengths lower than presently recommended, potentially resulting in a reduced or minimized side effect profile, among other potential benefits.

I. DEFINITIONS

The term "area under the curve" ("AUC") refers to the area under the curve defined by changes in the blood concentration of an active pharmaceutical ingredient (e.g., estradiol or progesterone), or a metabolite of the active pharmaceutical ingredient, over time following the administration of a dose of the active pharmaceutical ingredient. "$AUC_{0-\infty}$" is the area under the concentration-time curve extrapolated to infinity following the administration of a dose. "$AUC_{0-t}$" is the area under the concentration-time curve from time zero to time t following the administration of a dose, wherein t is the last time point with measurable concentration.

The term "$C_{max}$" refers to the maximum value of blood concentration shown on the curve that represents changes in blood concentrations of an active pharmaceutical ingredient (e.g., progesterone or estradiol), or a metabolite of the active pharmaceutical ingredient, over time.

The term "$T_{max}$" refers to the time that it takes for the blood concentration an active pharmaceutical ingredient (e.g., estradiol or progesterone), or a metabolite of the active pharmaceutical ingredient, to reach the maximum value.

Collectively AUC, $C_{max}$ and, optionally, $T_{max}$ are the principal pharmacokinetic parameters that can characterize the pharmacokinetic response of a particular drug product, such as progesterone or estradiol, in an animal, especially a mammal, including human, subject.

An "active pharmaceutical ingredient" (API), as used herein, means the active compound or compounds used in formulating a drug product. APIs are generally safe for administering to animals, especially mammals, including humans, according to established governmental standards, including those promulgated by the United States Food and Drug Administration.

The term "bioavailability" has the meaning as defined in 21 C.F.R. § 320.1(a): the rate and extent to which an API or active ingredient or active moiety is absorbed from a drug product and becomes available at the site of action. For drug products that are not intended to be absorbed into the bloodstream, bioavailability may be assessed by measurements intended to reflect the rate and extent to which the API or active ingredient or active moiety becomes available at the site of action. For example, bioavailability can be measured as the amount of API in the blood (serum or plasma) as a function of time. Pharmacokinetic (PK) parameters such as AUC, $C_{max}$, or $T_{max}$ may be used to measure and assess bioavailability.

The term "bioequivalent" has the meaning as defined in 21 C.F.R. § 320.1(e): the absence of a significant difference in the rate and extent to which the API or active ingredient or active moiety in pharmaceutical equivalents or pharmaceutical alternatives becomes available at the site of drug action when administered at the same molar dose under similar conditions in an appropriately designed study. Where there is an intentional difference in rate (e.g., in certain extended release dosage forms), certain pharmaceutical equivalents or alternatives may be considered bioequivalent if there is no significant difference in the extent to which the active ingredient or moiety from each product becomes available at the site of drug action. This applies only if the difference in the rate at which the active ingredient or moiety becomes available at the site of drug action is intentional and is reflected in the proposed labeling, is not essential to the attainment of effective body drug concentrations on chronic use, and is considered medically insignificant for the drug. In practice, two products are considered bioequivalent if the 90% confidence interval of the AUC, $C_{max}$, or optionally $T_{max}$ is within 80.00% to 125.00%.

As used herein, the term "comparable," as used with reference to comparing a bioavailability characteristic (including but not limited to area under the curve (AUC), $C_{max}$, or $T_{max}$) for a test composition, means that the test composition has a value for the bioavailability characteristic that is from 80% to 125% of the value of the bioavailability characteristic of a reference composition. In some embodiments, the reference composition is a commercially available progesterone composition (e.g., progesterone in a peanut oil, e.g., PROMETRIUM®) or a commercially available estradiol composition (e.g., a micronized estradiol tablet, e.g., ESTRACE®). In some embodiments, the reference composition is a co-administration of a commercially available progesterone composition (e.g., PROMETRIUM®) and a commercially available estradiol composition (e.g., ESTRACE®). In some embodiments, the reference composition is a combination formulation comprising progesterone and estradiol as provided herein. Thus, in some embodiments, a test composition is "comparable" to a reference combination formulation comprising progesterone and estradiol as provided herein when the test composition has a value for a bioavailability characteristic (e.g., $AUC_{(0-t)}$, $AUC_{(0-\infty)}$, $C_{max}$, and/or $T_{max}$ for one or more analytes, e.g., progesterone, unconjugated estradiol, unconjugated estrone, or total estrone) that is from 80% to 125% of the value of the bioavailability characteristic of the reference combination formulation.

The term "bio-identical hormone" or "body-identical hormone" refers to an active pharmaceutical ingredient that is structurally identical to a hormone naturally or endogenously found in the human body (e.g., estradiol and progesterone).

The term "estradiol" refers to (17β)-estra-1,3,5(10)-triene-3,17-diol. Estradiol is also interchangeably called 17β-estradiol, oestradiol, or E2, and is found endogenously in the human body. As used herein, estradiol refers to the bio-identical or body-identical form of estradiol found in the human body having the structure:

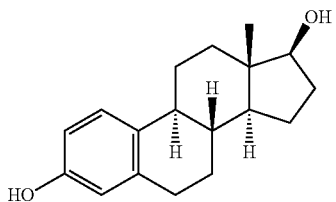

As used herein, unless specified, estradiol includes estradiol in anhydrous and hemihydrate forms. For the purposes of this disclosure, the anhydrous form or the hemihydrate form can be substituted for the other by accounting for the water or lack of water according to well-known and understood techniques.

The term "solubilized estradiol" means that the estradiol or a portion thereof is solubilized or dissolved in the solubilizing agents or the formulations disclosed herein. Solubilized estradiol may include estradiol that is about 80% solubilized, about 85% solubilized, about 90% solubilized, about 95% solubilized, about 96% solubilized, about 97% solubilized, about 98% solubilized, about 99% solubilized or about 100% solubilized. In some embodiments, the estradiol is "fully solubilized" with all or substantially all of the estradiol being solubilized or dissolved in the solubilizing agent. Fully solubilized estradiol may include estradiol that is about 97% solubilized, about 98% solubilized, about 99% solubilized or about 100% solubilized. Solubility can be expressed as a mass fraction (% w/w, which is also referred to as wt %).

The term "progesterone" refers to pregn-4-ene-3,20-dione. Progesterone is also interchangeably called P4 and is found endogenously in the human body. As used herein, prostergone refers to the bio-identical or body-identical form of progesterone found in the human body having the structure:

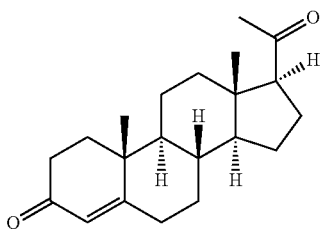

The term "solubilized progesterone" means that the progesterone or a portion thereof is solubilized or dissolved in the solubilizing agents or the formulations disclosed herein. In some embodiments, the progesterone is "partially solubilized" with a portion of the progesterone being solubilized or dissolved in the solubilizing agent and a portion of the progesterone being suspended in the solubilizing agent. The term "partially solubilized progesterone," as used herein, means progesterone which is in any state of solubilization up to but not including about 100%, e.g., about 1% solubilized, about 5% solubilized, about 10% solubilized, about 15% solubilized, about 20% solubilized, about 30% solubilized, about 40% solubilized, about 50% solubilized, about 60% solubilized, about 70% solubilized, about 80% solubilized, about 85% solubilized, about 90% solubilized, about 95% solubilized, or about 98% solubilized. In other embodiments, the progesterone is "fully solubilized" with all or substantially all of the progesterone being solubilized or dissolved in the solubilizing agent, e.g., at least about 98% solubilized, about 99% solubilized or about 100% solubilized. Solubility can be expressed as a mass fraction (% w/w, which is also referred to as wt %).

The terms "micronized progesterone" and "micronized estradiol," as used herein, include micronized progesterone and micronized estradiol, respectively, having an X50 particle size value below about 15 microns and/or having an X90 particle size value below about 25 microns. The term "X50," as used herein, means that one-half of the particles in a sample are smaller in diameter than a given number. For example, micronized progesterone having an X50 of 5 microns means that, for a given sample of micronized progesterone, one-half of the particles have a diameter of less than 5 microns. Similarly, the term "X90" means that ninety percent (90%) of the particles in a sample are smaller in diameter than a given number.

The terms "uniform distribution," "uniform dispersal," and "uniformly dispersed," as used with reference to estradiol or progesterone, means at least one of uniform dispersion, solubility, or lack of agglomeration of estradiol or progesterone in a dissolution test compared to a reference product (e.g., PROMETRIUM® or ESTRACE®, respectively) at a similar dosage strength and the same USP dissolution apparatus.

The terms "solubilizer" and "solubilizing agent" refer to any substance or mixture of substances that may be used to solubilize or to enhance the solubility of an active pharmaceutical ingredient (e.g., estradiol or progesterone). For example and without limitation, suitable solubilizing agents include medium chain oils and other solvents and co-solvents (e.g., surfactants) that solubilize or dissolve an active pharmaceutical ingredient to a desirable extent. Solubilizing agents suitable for use in the formulations disclosed herein are pharmaceutical grade solubilizing agents (e.g., pharmaceutical grade medium chain oils). It will be understood by those of skill in the art that other excipients or components can be added to or mixed with the solubilizing agent to enhance the properties or performance of the solubilizing agent or resulting formulation. Examples of such excipients include, but are not limited to, surfactants, emulsifiers, thickeners, colorants, flavoring agents, etc. In some embodiments, the solubilizer or solubilizing agent is a medium chain oil and, in some other embodiments, the medium chain oil is combined with a co-solvent(s) or other excipient(s).

The term "medium chain" is used to describe the aliphatic chain length of fatty acid containing molecules. As used herein, "medium chain" means any medium chain carbon-containing substance, including C4-C18, and including C6-C12 substances, fatty acid esters of glycerol, fatty acids, and mono-, di-, and tri-glycerides of such substances. In some embodiments, "medium chain" refers to fatty acids, fatty acid esters, or fatty acid derivatives that contain fatty acid aliphatic tails or carbon chains that contain between 6 (C6) and 14 (C14) carbon atoms. As non-limiting examples, C6-C14 fatty acids, C6-C12 fatty acids, and C8-C10 fatty acids are all medium chain fatty acids and may be used in instances in which this specification calls for use of medium chain fatty acids, e.g., medium chain fatty acid esters of glycerol or other glycols. Examples include, without limitation, caproic acid, caprylic acid, capric acid, lauric acid, myristic acid, and derivatives thereof.

The term "oil," as used herein, may be any pharmaceutically acceptable oil, such as an organic oil other than peanut oil, that would suspend and/or solubilize any suitable progesterone or estradiol, starting material, or precursor, including micronized progesterone or estradiol as described herein. In some embodiments, oils may include, for example and without limitation, medium chain fatty acids, generally of the group known as medium chain fatty acids consisting of at least one mono-, di-, or triglyceride, or derivatives thereof, or combinations thereof.

The term "medium chain oil" refers to an oil wherein the composition of the fatty acid fraction of the oil is substantially or predominantly medium chain (e.g., C6 to C14) fatty acids, i.e., the composition profile of fatty acids in the oil is substantially medium chain. As used herein, "substantially" or "predominantly" means that between 20% and 100% (inclusive of the upper and lower limits) of the fatty acid fraction of the oil is made up of medium chain fatty acids. In some embodiments, about 25%, about 30%, about 35%, about 40%, about 45%, about 50%, about 55%, about 60%, about 65%, about 70%, about 75%, about 80%, about 85%, about 90%, or about 95% of the fatty acid fraction of the oil is made up of medium chain fatty acids. It will be understood by those of skill in the art that the medium chain oils suitable for use in the formulations disclosed herein are pharmaceutical grade (e.g., pharmaceutical grace medium chain oils). Examples of medium chain oils include, for example and without limitation, medium chain fatty acids, medium chain fatty acid esters of glycerol (e.g., for example, mono-, di-, and triglycerides), medium chain fatty acid esters of propylene glycol, medium chain fatty acid derivatives of polyethylene glycol, and combinations thereof.

II. FORMULATIONS

In one aspect, this disclosure relates to pharmaceutical formulations for co-administering estradiol and progesterone to a human subject in need thereof. In some embodiments, the formulation comprises estradiol, progesterone, and a medium chain oil (e.g., a C6-C12 oil). In some embodiments, a pharmaceutical formulation comprising progesterone and estradiol as described herein demonstrates comparable bioavailability to their individual drug references of PROMETRIUM® and ESTRACE®, respectively, when the formulation is administered to a human subject or a population of subjects.

Another aspect of the present disclosure includes a pharmaceutical formulation of micronized progesterone, micronized progesterone with partially solubilized progesterone and fully solubilized progesterone, wherein the formulation may provide increased progesterone bioavailability in a treated subject compared to the bioavailability provided by PROMETRIUM® when administered at equal dosage strengths.

Additional objects of the present disclosure includes: providing increased patient compliance secondary to ease of use; providing increased physician adoption secondary to ease of use/instruction with less worry of side effects from inappropriate usage; providing decreased side-effects from erroneous use (decreased irregular bleeding); providing better efficacy/control of symptoms secondary to appropriate use; reducing the metabolic and vascular side effects of the commonly used synthetic progestins when administered alone or in combination with an estrogen (norethindrone acetate, medroxyprogesterone acetate, etc.) including, for example, stroke, heart attacks, blood clots and breast cancer.

Formulations of Estradiol and Progesterone

In some embodiments, a pharmaceutical formulation for use as described herein comprises solubilized estradiol without progesterone; micronized progesterone without estradiol; micronized progesterone with partially solubilized progesterone; solubilized estradiol with micronized progesterone; solubilized estradiol with micronized progesterone in combination with partially solubilized progesterone; or solubilized estradiol with solubilized progesterone. The underlying formulation concepts provided herein may be used with other natural or synthetic forms of estradiol and progesterone. Unless otherwise specified, "natural," as used herein with reference to hormones discussed herein, means bio-identical or body-identical hormones formulated to match the chemical structure and effect of those that occur naturally in the human body (endogenous). An exemplary natural estrogen is estradiol (also described as 17β-estradiol and E2) and a natural progestin is progesterone. Micronization specifications, aspects and embodiments are further defined herein.

Other aspects of the present disclosure further provide: more uniform dissolution of progesterone, and reduced intra- and inter-patient blood level variability in formulations of progesterone of the present disclosure, typically in combinations with solubilized estradiol, when compared to equal dosages of PROMETRIUM®). Blood level variability is also compared at equal sampling times following administration. Not to be limited by theory, these aspects are believed to be influenced by the percentage of solubilized progesterone in a respective formulation wherein such more uniform dissolution of progesterone, and lower intra- and inter-patient blood level variability, are influenced by a greater proportion of solubilized progesterone relative to total progesterone. A reduced food effect with the present formulations comprising progesterone may also be implicated.

According to the PROMETRIUM® prescribing information, clinical trials have shown significant patient variability. For example, a clinical trial involving post-menopausal women who were administered PROMETRIUM® once a day for five days resulted in the mean PK parameters listed in the following table:

TABLE 1

| Parameter | PROMETRIUM Capsules Daily Dose | | |
| --- | --- | --- | --- |
| | 100 mg | 200 mg | 300 mg |
| $C_{max}$ (ng/ml) | 17.3 +/− 21.9 | 38.1 +/− 37.8 | 60.6 +/− 72.5 |
| $T_{max}$ (hr) | 1.5 +/− 0.8 | 2.3 +/− 1.4 | 1.7 +/− 0.6 |
| $AUC_{0-10}$ (ngxhr/ml) | 43.4+/− 30.8 | 101.2 +/− 66.0 | 175.7 +/− 170.3 |

In particular illustrative aspects and embodiments of this invention, it is possible, though not necessary, to reduce the standard deviations in one or more of these PK parameters.

More uniform dissolution of progesterone in a formulation of the present disclosure compared to the dissolution of PROMETRIUM® at equal dosage strengths and using the same USP apparatus can be determined using standard techniques established for API dissolution testing, including that which is described in the examples below.

Reduced intra- and inter-patient variability of progesterone formulated pursuant to the present disclosure compared to PROMETRIUM can be demonstrated via a fed bio-study such as that described below.

Exemplary dosage strengths for estradiol for use in the formulations described herein include, without limitation, 0.125, 0.25, 0.375, 0.50, 0.625, 0.75, 1.00, 1.125, 1.25, 1.375, 1.50, 1.625, 1.75 and 2.00 mg. Exemplary dosage strengths for progesterone for use in the formulations described herein include, without limitation, 25, 50, 75, 100, 125, 150, 175, 200, 250, 300, 350 and 400 mg. These dosage strengths for each of estradiol and progesterone can be administered in formulations described herein either alone or in combination.

In some embodiments, estradiol is solubilized. Estradiol solubilization helps ensure high content uniformity and enhanced stability. Solubilized estradiol may include estradiol that is approximately 80% to 100% soluble in a solubilizing agent, including specifically embodiments that are: 80%, 81%, 82%, 83%, 84%, 85%, 86%, 87%, 88%, 89%, 90%, 91%, 92%, 93%, 94%, 95%, 96%, 97%, 98%, 99%, or 100% soluble in a solubilizing agent. Solubility may be expressed as a mass fraction (% w/w, also referred to as wt %).

In some embodiments, the composition comprises micronized progesterone. Progesterone active pharmaceutical ingredient may be micronized via any one of the multiple methods typically utilized by the ordinarily skilled artisan. In various embodiments, micronized progesterone has an X50 particle size value of less than about 15 microns, less than about 10 microns, less than about 5 microns and/or less than about 3 microns. In various embodiments, micronized progesterone has an X90 particle size value of less than about 25 microns, less than about 20 microns, and/or less than about 15 microns.

Particle size may be determined in any suitable manner. For example, a Beckman Coulter LS 13 320 Laser Diffraction Particle Size Analyzer (the "Beckman Device") may be used to determine particle size. As described above, particle size may be represented by various metrics, for example, through an X50 particle size, and/or X90 particle size, or similar descriptions of particle size.

The Beckman Device may be used with various modules for introducing a sample for analysis. The Beckman Device may be used with the LS 13 320 Universal Liquid Module ("ULM"). The ULM is capable of suspending samples in the size range of 0.017 μm to 2000 μm. The ULM is a liquid based module that allows for delivery of the sample to the sensing zone. The ULM recirculates the sample through the Beckman Device. The ULM comprises two hoses, one for fluid delivery and another for waste. The total volume used may be 125 mL or less. A sample mass of from about 1 mg to about 10 g may be used. The ULM may interact with the Beckman Device via pins that fit into slots on the ULM. The ULM may use a variety of suspension fluids, for example, water, butonol, ethanol, chloroform, heptanes, toluene, propanol, COULTER Type 1B Dispersant ("Coulter 1B"), and a variety of other suspension fluids. Surfactants may also be used, though pump speed should be adjusted to prevent excessive bubbling. Coulter 1B may comprise one or more of acetaldehyde, ethylene oxide, and/or 1,4-dioxane. The Beckman Device may be configured to use a variety of optical theories, including the Fraunhofer optical model and the Mie Theory.

The Beckman Device may comprise software to control the Beckman Device while the ULM is in use. The software may control, for example, pump speed, use of de-bubble routine, rinse routine, sonicate routine, and fill routine, among others. Parameters regarding the sample run may also be configured. For example, run length may be set. Though any suitable run length may be used, in various embodiments, a time period of 30 seconds to 120 seconds, and preferably between 30 seconds and 90 seconds may be used.

The Beckman Device may be used with the LS 13 320 Micro Liquid Module ("MLM"). The MLM is capable of suspending samples in the size range of 0.4 μm to 2000 μm. The MLM is a liquid based module that allows for delivery of the sample to the sensing zone. The MLM includes a stirrer. The total volume used may be 12 mL or less. The MLM may use a variety of suspension fluids, both aqueous and non-aqueous.

In some embodiments, the progesterone is solubilized. Fully solubilized progesterone formulations or partially solubilized progesterone formulations, in which at least about 50% of the progesterone, e.g., 75%, 80%, 85%, 90%, or >95% is solubilized, appear to provide improved PK-related properties.

In some embodiments, the estradiol and the progesterone are both in the solubilizing agent. In some embodiments, the estradiol and the progesterone are both uniformly dispersed in the pharmaceutical formulation.

In accordance with various aspects and embodiments, the solubility proportion (i.e., the proportion of a solute that enters solution) is notable. The weight ratio of estradiol to the weight of the entire solution is also notable due to the intended dose amounts, discussed herein. In particular, it is desirable to obtain a target dosage of estradiol in an amount of solution that may be readily administered via a capsule. For example, if it is desired to have a dose of estradiol in a capsule of between about 0.125 mg to about 2 mg, it would also be desirable to have a total solution weight to be between about 250 mg to about 400 mg, preferably about 300 mg to about 350 mg and more preferably about 325 mg. In various embodiments, the following weight ratios of estradiol to total solution are from about 0.125/50 mg to about 0.125/1000 mg, from about 1 mg:500 mg to about 1 mg:50 mg; from about 1 mg:250 mg to about 1 mg:60 mg; from about 1 mg:100 mg to about 1 mg:66 mg; from about 2 mg/50 mg to about 2 mg/1000 mg. In various embodiments, the target for single dose product is 325 mg, and a target fill weight for a combination product (e.g., two or more sterol APIs) is 650 mg.

In illustrative embodiments, total progesterone, i.e., dissolved and micronized, is 20 to 50 wt %, e.g., 30 to 35 wt %; estradiol is 0.1 to 0.8 wt %, e.g., 0.15 to 0.35 wt %.

Solubilizing Agents

In various embodiments, the solubilizing agent is selected from at least one of a solvent or co-solvent. Suitable solvents and co-solvents include any mono-, di- or triglyceride and glycols, and combinations thereof.

In some embodiments, formulations of the present disclosure (e.g., estradiol and progesterone formulations) are prepared via blending with a pharmaceutically acceptable oil; generally, the oil comprises at least one medium chain fatty acid such as medium chain fatty acids consisting of at least one mono-, di-, or triglyceride, or derivatives thereof, or combinations thereof. Optionally added are other excipients including, for example and without limitation, antioxidants, lubricants and the like. Sufficient oil is used to form a suspension of micronized progesterone or, in the alternative, solubilize progesterone.

In illustrative embodiments of the invention, oils used to solubilize estradiol and to suspend, partially solubilize, or fully solubilize progesterone include medium chain fatty acid esters (e.g., esters of glycerol, polyethylene glycol, or propylene glycol) and mixtures thereof. In illustrative embodiments, the medium chain fatty acids are C6 to C14 or C6 to C12 fatty acids. In illustrative embodiments, the medium chain fatty acids are saturated, or predominantly saturated, e.g., greater than about 60% or greater than about 75% saturated.

Mixtures of medium chain fatty acid glycerides, e.g., C6-C12, C8-C12, or C8-C10 fatty acid mono- and diglycerides or mono-, di-, and triglycerides are very well suited for dissolving estradiol; good results have been obtained with an oil that is predominantly a mixture of C8-C10 saturated fatty acid mono- and diglycerides. Longer chain glycerides appear to be not as well suited for dissolution of estradiol. On the other hand, high solubility of progesterone has been obtained in mixtures that are predominantly medium chain fatty acid triglycerides.

Pharmaceutically acceptable oils include, without limitation, the use of at least one of caproic fatty acid; caprylic fatty acid; capric fatty acid; tauric acid; myristic acid; linoleic acid; succinic acid; glycerin; mono-, di-, or triglycerides and combinations and derivatives thereof; a polyethylene glycol; a polyethylene glycol glyceride (GELUCIRE®, a polyethylene glycol glyceride); GATTEFOSSE SAS, Saint-Priest, France); a propylene glycol; a caprylic/capric triglyceride (MIGLYOL® (caprylic/capric triglyceride) SASOL Germany GMBH, Hamburg; MIGLYOL® includes MIGLYOL® 810, 812, 816 and 829); a caproic/caprylic/capric/lauric triglyceride; a caprylic/capric/linoleic triglyceride; a caprylic/capric/succinic triglyceride; propylene glycol monocaprylate; propylene glycol monocaprate; (CAPMUL® PG-8 (propylene glycol monocaprylate) and 10; the CAPMUL® MCM (medium chain mono- and diglycerides) brands are owned by ABITEC, Columbus Ohio); propylene glycol dicaprylate; propylene glycol dicaprylate; medium chain mono- and di-glycerides (CAPMUL® MCM); a diethylene glycol mono ester (including 2-(2-Ethoxyethoxy)ethanol: TRANSCUTOL® (diethylene glycol monoethyl ether); esters of saturated coconut and palm kernel oil and derivatives thereof; triglycerides of fractionated vegetable fatty acids, and combinations and derivatives thereof.

Illustrative examples of mono- and diglycerides of medium chain fatty acids include, among others, CAPMUL® MCM, CAPMUL® MCM C10, CAPMUL® MCM C8, and CAPMUL® MCM C8 EP. These oils are C8 and C10 fatty acid mono- and diglycerides. Illustrative examples of oils that are triglycerides of medium chain fatty acids include, among others, MIGLYOL® 810 and MIGLYOL® 812.

Illustrative examples of oils that are medium chain fatty acid esters of propylene glycol include, among others, CAPMUL® PG-8, CAPMUL® PG-2L EP/NF, CAPMUL® PG-8 NF, CAPMUL® PG-12 EP/NF and CAPRYOL™. Other illustrative examples include MIGLYOL® 840.

Illustrative examples of oils that are medium chain fatty acid esters of polyethylene glycol include, among others, GELUCIRE® 44/14 (PEG-32 glyceryl laurate EP), which is polyethylene glycol glycerides composed of mono-, di- and triglycerides and mono- and diesters of polyethylene glycol. Without intending to be bound to any particular mechanism, it appears that at least in formulations comprising small amounts of GELUCIRE®, e.g., 10 wt % or less, the primary function of this oil is as a non-ionic surfactant.

These illustrative examples comprise predominantly medium chain length, saturated, fatty acids, specifically predominantly C8 to C12 saturated fatty acids.

In accordance with various embodiments, the formulations of the present disclosure do not include peanut oil.

It will be understood that commercially available fatty acid esters of glycerol and other glycols are often prepared from natural oils and therefore may comprise components additional to the fatty acid esters that comprise the predominant (by weight) component(s) and that therefore are used to characterize the product. Such other components may be, e.g., other fatty acid triglycerides, mono- and diesters, free glycerol, or free fatty acids. So, for example, when an oil/solubilizing agent is described herein as a saturated C8 fatty acid mono- or diester of glycerol, it will be understood that the predominant component of the oil, i.e., >50 wt % (e.g., >75 wt %, >85 wt % or >90 wt %) are caprylic monoglycerides and caprylic diglycerides. For example, the Technical Data Sheet by ABITEC for CAPMUL® MCM C8 describes CAPMUL® MCM C8 as being composed of mono and diglycerides of medium chain fatty acids (mainly caprylic) and describes the alkyl content as ≤1% C6, ≥95% C8, ≤5% C10, and ≤1.5% C12 and higher.

By way of further example, MIGLYOL® 812 is generally described as a C8-C10 triglyceride because the fatty acid composition is at least about 80% caprylic (C8) acid and capric (C10) acid. However, it can also comprise small amounts of other fatty acids, e.g., less than about 5% of caproic (C6) acid, lauric (C12) acid, and myristic (C14) acid.

Specifically, a product information sheet for MIGLYOL® by SASOL provides the composition of fatty acids as follows:

TABLE 2

MIGLYOL ® Fatty Acid Composition

| Fatty acid | MIGLYOL® 810 | MIGLYOL® 812 | MIGLYOL® 818 | MIGLYOL® 829 | MIGLYOL® 840 |
|---|---|---|---|---|---|
| Caproic acid (C6:0) | max. 2.0 | max. 2.0 | max. 2 | max. 2 | max. 2 |
| Caprylic acid (C8:0) | 65.0-80.0 | 50.0-65.0 | 45-65 | 45-55 | 65-80 |
| Capric acid (C10:0) | 20.0-35.0 | 30.0-45.0 | 30-45 | 30-40 | 20-35 |
| Lauric acid (C12:0) | max. 2 | max. 2 | max. 3 | max. 3 | max. 2 |

TABLE 2-continued

MIGLYOL ® Fatty Acid Composition

| Fatty acid | MIGLYOL ® 810 | MIGLYOL ® 812 | MIGLYOL ® 818 | MIGLYOL ® 829 | MIGLYOL ® 840 |
|---|---|---|---|---|---|
| Myristic acid (C14:0) | max. 1.0 | max. 1.0 | max. 1 | max. 1 | max. 1 |
| Linoleic acid (C18:2) | — | — | 2-5 | — | — |
| Succinic acid | — | — | — | 15-20 | — |

Where certain embodiments of this invention are described as comprising (or consisting essentially of) a capsule shell, estradiol solubilized in C8-C10 triglycerides, and a thickening agent, it will be understood that the fatty acid esters component of the formulation may be, e.g., MIGLYOL® 812 or a similar product.

By way of further illustration, GELUCIRE® 44/14 is generally described as lauroyl polyoxyl-32 glycerides, i.e., polyoxyethylene 32 lauric glycerides (which is a mixture of mono-, di-, and triesters of glycerol and mono- and diesters of PEGs) because the fatty acid composition is 30 to 50% lauric acid and smaller amounts of other fatty acids, e.g., up to 15% caprylic acid, up to 12% capric acid, up to 25% myristic acid, up to 25% palmitic acid, and up to 35% stearic acid. The product may also contain small amounts of non-esterified glycols. Where certain embodiments of this invention are described as described as comprising (or consisting essentially of) a capsule shell, estradiol solubilized in triglycerides, and a thickening agent that is a non-ionic surfactant comprising C8 to C18 fatty acid esters of glycerol and polyethylene glycol, it will be understood that the thickening agent component of the formulation may be, e.g., GELUCIRE® 44/14 or a similar product.

Similarly, where certain embodiments of this invention are as described as comprising (or consisting essentially of) a capsule shell, estradiol solubilized in triglycerides, and a thickening agent that is a non-ionic surfactant comprising PEG-6 stearate, ethylene glycol palmitostearate, and PEG-32 stearate, it will be understood that the thickening agent component of the formulation may be, e.g., TEFOSE® 63 or a similar product.

In addition to the oils referenced above, other solubilizers include, for example and without limitation, glyceryl mono- and di-caprylates, propylene glycol and 1,2,3-propanetriol (glycerol, glycerin, glycerine).

Anionic and/or non-ionic surfactants can be used in other embodiments of the presently disclosed formulations containing estradiol, progesterone or a combination thereof. In certain embodiments, a non-ionic surfactant is used. Exemplary non-ionic surfactants may include, for example and without limitation, one or more of oleic acid, linoleic acid, palmitic acid, and stearic acid esters or alcohols. In further embodiments, the non-ionic surfactant may comprise polyethylene sorbitol esters, including polysorbate 80, which is commercially available under the trademark TWEEN 80® (Sigma Aldrich, St. Louis, Mo.). Polysorbate 80 comprises approximately 60%-70% oleic acid with the remainder comprising primarily linoleic acids, palmitic acids, and stearic acids. Polysorbate 80 may be used in amounts ranging from about 5 to 50%, and in certain embodiments, about 30% of the formulation total mass.

In various other embodiments, the non-ionic surfactant is selected from one or more of glycerol and polyethylene glycol esters of fatty acids, for example, lauroyl macrogol-32 glycerides and/or lauroyl polyoxyl-32 glycerides, commercially available as GELUCIRE®, including, for example, GELUCIRE® 44/11 and GELUCIRE® 44/14. These surfactants may be used at concentrations greater than about 0.01%, and typically in various amounts of about 0.01%-10.0%, 10.1%-20%, and 20.1%-30%. In certain examples, below, GELUCIRE® 44/14 is used as a surfactant in amounts of 1 to 10 wt %. See, e.g., Tables 13-17, below. Other non-ionic surfactants include, e.g., LABRASOL® PEG-8 Caprylic/Capric Glycerides (Gattefosse) and LABARAFIL® corn/apricot oil PEG-6 esters (Gattefosse).

Other Excipients

In other embodiments, a lubricant is used. Any suitable lubricant may be used, such as for example lecithin. Lecithin may comprise a mixture of phospholipids.

In additional embodiments, an antioxidant is used. Any suitable antioxidant may be used such as, for example and without limitation, butylated hydroxytoluene.

For example, in various embodiments, a pharmaceutical formulation comprises about 20% to about 80% carrier by weight, about 0.1% to about 5% lubricant by weight, and about 0.01% to about 0.1% antioxidant by weight.

The choice of excipient will, to a large extent, depend on factors such as the particular mode of administration, the effect of the excipient on solubility and stability, and the nature of the dosage form. Excipients used in various embodiments may include colorants, flavoring agents, preservatives and taste-masking agents. Colorants, for example, may comprise about 0.1% to about 2% by weight. Preservatives may comprise methyl and propyl paraben, for example, in a ratio of about 10:1, and at a proportion of about 0.005% and 0.05% by weight.

As is with all oils, solubilizers, excipients and any other additives used in the formulations described herein, each is to be non-toxic and pharmaceutically acceptable.

Formulation and Administration

In some embodiments, combinations of solubilizing agents (e.g., two or more oils or combinations of one or more oils and one or more surfactants) are used to form estradiol and progesterone compositions. Various ratios of these solubilizing agents (e.g., oils or surfactants) can be used. CAPMUL® MCM and a non-ionic surfactant, e.g., GELUCIRE® 44/14 (lauroyl macrogol-32 glycerides EP; lauroyl polyoxyl-32 glycerides NF; lauroyl polyoxylglycerides (USA FDA IIG)), can be used at ratios of about 99:1 to 2:1, including, for example and without limitation: 60:40, 65:35, 70:30, 75:25, 80:10, 80:15, 85:20, 90:10, and 98:1. The ratios of oil (e.g., medium chain fatty acid esters of monoglycerides and diglycerides) to non-ionic surfactant can be significantly higher. For example, in certain examples, below, CAPMUL® MCM and GELUCIRE® were used in ratios of up to about 65:1, e.g., 8:1, 22:1, 49:1, 65:1 and 66:1. See, e.g., Tables 20-24, below. Thus, useful ratios can be 8:1 or greater, e.g., 60 to 70:1. Among other combinations, these solubilizers, as defined herein, and combinations thereof, can be used to form combination estradiol and progesterone formulations of the present disclosure.

In illustrative embodiments, estradiol or progesterone is soluble in the oils at room temperature, although it may be desirable to warm the oils up until they are in a liquid state. In illustrative embodiments, the oil or oil/surfactant is liquid at between room temperature and about 50° C., e.g., at or below 50° C., at or below 40° C., or at or below 50° C. In illustrative embodiments, GELUCIRE® 44/14 is heated to about 65° C. and CAPMUL® MCM is heated to about 40° C. to facilitate mixing of the oil and non-surfactant, although such heating is not necessary to dissolve the estradiol or progesterone. In illustrative embodiments, the solubility of estradiol in the oil (or oil/surfactant) is at least about 0.5 wt %, e.g., 0.8 wt % or higher, or 1.0 wt % or higher. However, much higher solubility can be achieved. For example, as shown in Example 4, below, estradiol is stable in solution in CAPMUL® MCM at 12 mg/g (which is approximately equal to 12 mg/ml). As shown in Example 19, such solubility is favored over results observed in longer chain and unsaturated fatty acid esters.

High solubility of estradiol has been obtained in 2-(2-Ethoxyethoxy)ethanol, e.g., TRANSCUTOL® and in Propylene glycol monocaprylate, e.g., CAPRYOL™ 90 (Gattefosse).

In some embodiments, progesterone is fully solubilized using, for example and without limitation, sufficient amounts of: TRANSCUTOL® and MIGLYOL®; TRANSCUTOL®, MIGLYOL® and CAPMUL® PG 8 and/or PG 10; CAPMUL® MCM; CAPMUL® and a nonionic surfactant; and CAPMUL® MCM and GELUCIRE®.

Combinations of these oils can produce partially solubilized progesterone, depending upon the desired unit dosage amount of progesterone. The greater the amount of progesterone per unit dosage form, the less progesterone may be solubilized. The upward limit of dosage strength per unit dose it generally limited only by the practical size of the final dosage form.

In illustrative embodiments of the invention, the selected oil does not require excessive heating in order to solubilize progesterone or estradiol. For example, when the formulation comprises medium chain fatty acid mono- and diglycerides (e.g., CAPMUL® MCM) and polyethylene glycol glycerides (e.g., GELUCIRE®) as a surfactant, the oil and/or the surfactant can be warmed up, e.g., to about 65° C. in the case of the surfactant and less in the case of the oil, to facilitate mixing of the oil and surfactant. The estradiol can be added at this temperature or at lower temperatures as the mixture cools or even after it has cooled as temperatures above room temperature, e.g., about 20° C., are not required to solubilize the estradiol in preferred oils. The progesterone can also be added as the mixture cools, e.g., to below about 40° C. or to below about 30° C., even down to room temperature.

As a non-limiting example, an illustrative embodiment of a pharmaceutical composition of the invention comprises solubilized estradiol, progesterone at least 75% of the progesterone being solubilized (the balance being micronized as discussed elsewhere herein), and an oil, wherein the oil is medium chain fatty acid mono- and diesters of glycerol, with or without surfactant. In certain embodiments, a specification for progesterone is set at >80% solubilized, <20% micronized or >85% solubilized, <15% micronized. Specific examples of such illustrative embodiments, with GELU-CIRE® as surfactant, in which at least about 85% of the progesterone can be solubilized, include, e.g., the following four formulations:

TABLE 3

Formulation A—P:50/E2:0.25:

| Ingredient(s) | Amount (% w/w) | Qty/Capsule (mg) |
|---|---|---|
| Progesterone, USP, micronized | 33.33 | 50.00 |
| Estradiol Hemihydrate | 0.17 | 0.26 |
| CAPMUL ® MCM, NF | 65.49 | 98.24 |
| GELUCIRE ® 44/14, NF | 1.00 | 1.50 |
| Total | 100.00 | 150.00 |

TABLE 4

Formulation B—P:50/E2:0.5:

| Ingredient(s) | Amount (% w/w) | Qty/Capsule (mg) |
|---|---|---|
| Progesterone, USP, micronized | 33.33 | 50.00 |
| Estradiol Hemihydrate | 0.35 | 0.52 |
| CAPMUL ® MCM, NF | 65.32 | 97.98 |
| GELUCIRE ® 44/14, NF | 1.00 | 1.50 |
| Total | 100.00 | 150.00 |

TABLE 5

Formulation C—P:100/E2:0.5:

| Ingredient(s) | Amount (% w/w) | Qty/Capsule (mg) |
|---|---|---|
| Progesterone, USP, micronized | 33.33 | 100.00 |
| Estradiol Hemihydrate | 0.17 | 0.52 |
| CAPMUL ® MCM, NF | 65.49 | 196.48 |
| GELUCIRE ® 44/14, NF | 1.00 | 3.00 |
| Total | 100.00 | 300.00 |

TABLE 6

Formulation D—P:100/E2:1:

| Ingredient(s) | Amount (% w/w) | Qty/Capsule (mg) |
|---|---|---|
| Progesterone, USP, micronized | 33.33 | 100.00 |
| Estradiol Hemihydrate | 0.34 | 1.03 |
| CAPMUL ® MCM, NF | 65.32 | 195.97 |
| GELUCIRE ® 44/14, NF | 1.00 | 3.00 |
| Total | 100.00 | 300.00 |

TABLE 7

Formulation E—P:200/E2:2:

| Ingredient(s) | Amount (% w/w) | Qty/Capsule (mg) |
|---|---|---|
| Progesterone, USP, micronized | 33.33 | 200.00 |
| Estradiol Hemihydrate | 0.34 | 2.06 |
| CAPMUL ® MCM, NF | 65.32 | 391.94 |
| GELUCIRE ® 44/14, NF | 1.00 | 6.00 |
| Total | 100.00 | 600.00 |

*Note:
1.00 mg Estradiol equivalent to 1.03 mg Estradiol Hemihydrate.

In general terms, the above formulations comprise 30 to 35 wt % progesterone, 0.1 to 0.4 wt % estradiol (or estradiol hemihydrate), 55 to 75 wt % of an oil that is predominantly medium chain fatty acid mono- and diglycerides, such as CAPMUL® MCM, and 0.5 to 10 wt % non-ionic surfactant, such as GELUCIRE® 44/14. The above formulations may be modified to comprise excipients, e.g., gelatin such as Gelatin 200 Bloom, glycerin, coloring agents such as Opatint red and white, and, optionally, MIGLYOL® 812.

Estradiol solubilization helps ensure high content uniformity and enhanced stability. Fully solubilized progesterone formulations or partially solubilized progesterone formulations in which at least about 50% of the progesterone, e.g., 75%, 80%, 85%, 90%, or >95%, is solubilized appear to provide improved PK-related properties.

Pharmaceutical formulations as described herein can be either solid or liquid. Solid form preparations include powders, tablets, pills, capsules, cachets, suppositories, and dispersible granules. A solid preparation can comprise one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Mack Publishing Co, Easton Pa. ("Remington's").

In some embodiments, the pharmaceutical formulations described herein are prepared and administered as filled capsules, typically soft capsules of one or more materials well known in the art including, for example and without limitation, soft gelatin capsules. Micronized progesterone, as described herein, may also be prepared for administration in tablets or other well-known orally administered dosage forms using standard techniques.

In some embodiments, in which the carrier is a medium fatty acid ester of a glycol and which comprise a non-ionic surfactant as described herein, the formulations are in liquid form, i.e., not gels, hard fats or other solid forms.

In general, the type of composition is selected based on the mode of administration. A pharmaceutical composition (e.g., for oral administration or delivery by injection) can be in the form of a liquid (e.g., an elixir, syrup, solution, emulsion or suspension). Alternatively, a pharmaceutical composition as described herein can take the form of a pill, tablet, or capsule containing the liquid oil, and thus, the composition can contain any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. The composition can also be formulated into a suppository disposed, for example, in a polyethylene glycol (PEG) solubilizing agent.

Administration of the formulations described herein can be carried out via any of the accepted modes of administration. Thus, administration can be, for example, intravenous, topical, subcutaneous, transcutaneous, transdermal, intramuscular, oral, intra-joint, parenteral, intra-arteriole, intradermal, intraventricular, intracranial, intraperitoneal, intralesional, intranasal, rectal, vaginal, or by inhalation. In some embodiments, a composition as described herein is administered orally. For example, a pharmaceutical composition as described herein can be administered via capsules such as soft capsules. In some embodiments, a pharmaceutical composition as described herein is administered once daily.

According to various embodiments described herein, a 28-day or monthly regimen of capsules can be packaged in a single kit (e.g., a blister pack) having administration days identified to improve compliance and reduce associated symptoms, among others. One or more of the capsules may contain no estradiol, for example, and/or no progesterone. Capsules that comprise no estrogen or progesterone API may be referred to as placebos. A blister pack can have a plurality of scores or perforations separating blister pack into 28 days. Each day may further comprise a single blister or a plurality of blisters. In various embodiments, each unit dose may contain micronized and/or partially solubilized, or fully solubilized progesterone and/or solubilized estradiol in amounts as set forth herein above, although other dose ranges may be contemplated. In addition, kits having other configurations are also contemplated herein. For example, without limitation, kits having such blister packs may contain any number of capsules.

As referenced above, the formulations of the present disclosure are generally orally administered, typically via, for example, capsules such as soft capsules. The present formulations can also be used to form transdermal patches using standard technology known in the art. Solubilized formulations of the present invention can also be formulated for intraperitoneal administration using techniques well known in the art.

In some embodiments, the pharmaceutical formulations disclosed herein are useful in treating conditions in subjects caused, at least in part, by estrogen deficiency, particularly for women with a uterus. For example, in some embodiments, the formulations disclosed herein are useful for the treatment of an animal, especially a mammal, including humans, for menopause; for endometrial hyperplasia; for secondary amenorrhea; as a method of treatment for preterm birth, when said animal has a shortened cervix, and other disease states or conditions treated with supplemental progesterone or estrogen. In some embodiments, a formulation as disclosed herein is useful for treating one or more symptoms of menopause such as vaginal atrophy, vaginal dryness, watery discharge, skin dryness, osteoporosis, thin bones, painful fractures, incontinence, urinary frequency, urinary urgency, urinary tract infections, temperature dyregulation (e.g., feeling unusually hot or cold or temperature swings), dysfunctional bleeding, rapid heartbeat, migraine, breast tenderness or swelling, breast atrophy, decreased skin elasticity, back pain, joint pain, muscle pain, fatigue, decreased libido, dyspareunia, vasomotor symptoms (e.g., flushing, hot flashes), irritability, memory loss, mood disturbance, depression, anxiety, sleep disturbance, and sweating. Thus, in some embodiments, the present disclosure provides methods of treating such a condition by administering to the subject a composition comprising estradiol and progesterone as described herein. As used herein, the term "treatment," or a derivative thereof, contemplates partial or complete inhibition of the stated disease state when a formulation as described herein is administered prophylactically or following the onset of the disease state for which such formulation is administered. For the purposes of the present disclosure, "prophylaxis" refers to administration of the active ingredient(s) to an animal, especially a mammal, to protect the animal from any of the disorders set forth herein, as well as others.

Bioavailability Properties

The pharmaceutical formulations of the present disclosure can be formulated to provide desirable pharmacokinetic parameters in a subject (e.g., a female subject) to whom the composition is administered. In some embodiments, a pharmaceutical composition as described herein produces desirable pharmacokinetic parameters for progesterone in the subject. In some embodiments, a pharmaceutical composition as described herein produces desirable pharmacokinetic parameters for estradiol in the subject. In some embodiments, a pharmaceutical composition as described herein produces desirable pharmacokinetic parameters for one or more metabolites of progesterone or estradiol in the subject, for example estrone or total estrone.

In certain embodiments, combination formulations of the present disclosure exhibit bioavailability properties that are comparable to the bioavailability properties of the components of the combination formulation when individually formulated (e.g., progesterone in a peanut oil, e.g., PROMETRIUM®, and a micronized estradiol tablet, e.g., ESTRACE®). In certain embodiments, a composition is within the scope of the invention if it has a value for a pharmacokinetic parameter that is about 80% to about 125% of the value of the pharmacokinetic parameter for a reference composition when said formulation is administered to a human subject.

Following the administration of a composition comprising progesterone and estradiol to a subject, the concentration and metabolism of progesterone or estradiol can be measured in a sample (e.g., a plasma sample) from the subject. Progesterone is metabolized to pregnanediols and pregnanolones, which are then conjugated to glucuronide and sulfate metabolites that are excreted or further recycled. Estradiol is converted reversibly to estrone, and both estradiol and estrone can be converted to the metabolite estriol. In postmenopausal women, a significant proportion of circulating estrogens exist as sulfate conjugates, especially estrone sulfate. Thus, estrone can be measured with respect to "estrone" amounts (excluding conjugates such as estrone sulfate) and "total estrone" amounts (including both free, or unconjugated, estrone and conjugated estrone such as estrone sulfate).

The pharmaceutical formulations of the present disclosure can be characterized for one or more pharmacokinetic parameters of progesterone, estradiol, or a metabolite thereof following administration of the composition to a subject or to a population of subjects. These pharmacokinetic parameters include AUC, $C_{max}$, and $T_{max}$.

In certain embodiments, a composition is within the scope of the invention if it has a $C_{max}$ value that is about 80% to about 125% of the $C_{max}$ value of the reference composition. $C_{max}$ is well understood in the art as an abbreviation for the maximum drug concentration in serum or plasma of the test subject. In certain embodiments, a composition is within the scope of the invention if it has a $T_{max}$ value that is about 80% to about 125% of the $T_{max}$ value of the reference composition. $T_{max}$ is well understood in the art as an abbreviation for the time to maximum drug concentration in serum or plasma of the test subject. In vivo testing protocols for determining a $C_{max}$ and/or $T_{max}$ value can be designed in a number of ways.

In certain embodiments, a composition is within the scope of the invention if it has an AUC value that is about 80% to about 125% of the AUC value of the reference composition. AUC is a determination of the area under the curve (AUC) plotting the serum or plasma concentration of drug along the ordinate (Y-axis) against time along the abscissa (X-axis). AUCs are well understood, frequently used tools in the pharmaceutical arts and have been extensively described, for example in "Pharmacokinetics Processes and Mathematics," Peter E. Welling, ACS Monograph 185; 1986.

Any of a variety of methods can be used for measuring the levels of progesterone, estradiol, estrone, or total estrone in a sample, including immunoassays, mass spectrometry (MS), high performance liquid chromatography (HPLC) with ultraviolet fluorescent detection, liquid chromatography in conjunction with mass spectrometry (LC-MS), tandem mass spectrometry (MS/MS), and liquid chromatography-tandem mass spectrometry (LC-MS/MS). It will be understood by a person of skill in the art that the sensitivity of the assay used will correlate with the level of quantification that can be detected, and that a more sensitivity assay will enable lower levels of quantification of progesterone, estradiol, estrone, or total estrone. In some embodiments, the levels of progesterone, estradiol, estrone, or total estrone are measured using a validated LC-MS/MS method. Methods of measuring hormone levels are well described in the literature.

The levels of progesterone, estradiol, estrone, or total estrone can be measured in any biological sample, e.g. a tissue or fluid such as blood, serum, plasma, or urine. In some embodiments, the sample is blood or plasma. In some embodiments, the levels of progesterone, estradiol, estrone, or total estrone are measured about 0.0, 0.10, 0.20, 0.05, 0.30, 0.35, 0.40, 0.45, 0.5, 1, 2, 3, 4, 5, 6, 7, 8, 9, 10, 12, 15, 18, 21, 24, 27, 30, 33, 36, 39, 42, 45, or 48 hours after dosing, or any other appropriate time period that is common or useful in determining the levels of each of the hormones. Generally, assays to determine the levels of progesterone, estradiol, estrone, or total estrone are measured one or more times every 5, 10, 15, 20, 30, 60, 120, 360, 480, 720, or 1440 minutes after administration, or combinations thereof (e.g., the first measurements are taken every 15 minutes for the first hour, followed by every 120 minutes thereafter). In some embodiments, the levels of progesterone, estradiol, estrone, or total estrone are measured about 48 hours after dosing. In embodiments, the timing of such measurements are designed to accurately measure $C_{max}$, $T_{max}$, or AUC. Timing can be adjusted based on the given circumstances (i.e., one formulation may cause a more rapid $C_{max}$, in which case the initial times would be clustered closer together, closer to time zero, or both to ensure accurate measurement of $C_{max}$, $T_{max}$, and AUC).

In some embodiments, the values for $C_{max}$, $T_{max}$, and/or AUC represent a number of values taken from all the subjects in a patient test population and are, therefore, mean values averaged over the entire test population. Alternatively, the $C_{max}$ value, $T_{max}$ value, and/or AUC test/AUC control ratio may be determined for each subject, then averaged.

In some embodiments, administration of the pharmaceutical formulation as disclosed herein (e.g., a pharmaceutical formulation comprising solubilized estradiol, suspended progesterone, and a medium chain (C6-C12) oil) to a subject produces, in a plasma sample from the subject, one or more parameters selected from:

(i) an $AUC_{(0-t)}$ for estradiol that is from 1123 pg·h/ml to 1755 pg·h/ml;

(ii) an $AUC_{(0-\infty)}$ for estradiol that is from 1968 pg·hr/ml to 3075 pg·hr/ml; or (iii) a $C_{max}$ for estradiol that is from 52 pg/ml to 81 pg/ml.

In some embodiments, administration of the formulation to the subject produces both an $AUC_{(0-t)}$ for estradiol that is from 1123 pg·h/ml to 1755 pg·h/ml, and a $C_{max}$ for estradiol that is from 52 pg/ml to 81 pg/ml.

In some embodiments, administration of the formulation to the subject further produces, in a plasma sample from the subject, one or more parameters selected from:

(i) an $AUC_{(0-t)}$ for progesterone that is from 96 ng·hr/ml to 150 ng·hr/ml;

(ii) an $AUC_{(0-\infty)}$ for progesterone that is from 105 ng·hr/ml to 164 ng·hr/ml; or (ii) a $C_{max}$ for progesterone that is from 71 ng/ml to 112 ng/ml.

In some embodiments, administration of the composition to the subject produces both an $AUC_{(0-t)}$ for progesterone that is from 96 ng·hr/ml to 150 ng·hr/ml, and a $C_{max}$ for progesterone that is from 71 ng/ml to 112 ng/ml.

In some embodiments, administration of the formulation to the subject produces, in a plasma sample from the subject, (i) an $AUC_{(0-t)}$ for estradiol that is from 1123 pg·h/ml to 1755 pg·h/ml;

(ii) a $C_{max}$ for estradiol that is from 52 pg/ml to 81 pg/ml;

(iii) an $AUC_{(0-t)}$ for progesterone that is from 96 ng·hr/ml to 150 ng·hr/ml; or (iv) a $C_{max}$ for progesterone that is from 71 ng/ml to 112 ng/ml.

In some embodiments, administration of the pharmaceutical formulation to the subject produces, in a plasma sample from the subject, one, two, three or more parameters selected from:

(i) an $AUC_{(0-t)}$ for estradiol that is from 1123 pg·h/ml to 1755 pg·h/ml;

(ii) a $C_{max}$ for estradiol that is from 52 pg/ml to 81 pg/ml;

(iii) an $AUC_{(0-t)}$ for progesterone that is from 96 ng·hr/ml to 150 ng·hr/ml; or (iv) a $C_{max}$ for progesterone that is from 71 ng/ml to 112 ng/ml.

In some embodiments, administration of the pharmaceutical formulation to the subject produces both parameters (i) and (ii). In some embodiments, administration of the formulation to the subject produces both parameters (i) and (iii). In some embodiments, administration of the formulation to the subject produces both parameters (i) and (iv). In some embodiments, administration of the formulation to the subject produces both parameters (ii) and (iii). In some embodiments, administration of the formulation to the subject produces both parameters (ii) and (iv). In some embodiments, administration of the formulation to the subject produces both parameters (iii) and (iv). In some embodiments, administration of the formulation to the subject produces all of parameters (i), (ii), and (iii). In some embodiments, administration of the formulation to the subject produces both parameters (i), (iii), and (iv). In some embodiments, administration of the formulation to the subject produces both parameters (ii), (iii), and (iv). In some embodiments, administration of the formulation to the subject produces all of parameters (i), (ii), (iii), and (iv).

In some embodiments, administration of the pharmaceutical formulation to the subject further produces, in a plasma sample from the subject, one or more parameters selected from:

(i) an $AUC_{(0-t)}$ for estrone sulfate that is from 7277 pg·hr/ml to 11370 pg·hr/ml;

(ii) an $AUC_{(0-\infty)}$ for estrone sulfate that is from 9596 pg·hr/ml to 14994 pg·hr/ml; or (ii) a $C_{max}$ for estrone sulfate that is from 341 pg/ml to 533 pg/ml.

In some embodiments, administration of the pharmaceutical composition to the subject further produces, in a plasma sample from the subject, one or more parameters selected from:

(i) an $AUC_{(0-t)}$ for total estrone that is from 161 pg·h/ml to 252 pg·h/ml;

(ii) an $AUC_{(0-\infty)}$ for total estrone that is from 171 pg·hr/ml to 267 pg·hr/ml; or (ii) a $C_{max}$ for total estrone that is from 28 pg/ml to 44 pg/ml.

In some embodiments, the pharmaceutical composition is administered to a population of subjects in need thereof, and mean parameters are determined for samples (e.g., plasma samples) from the subjects administered the composition. Thus, in some embodiments, administration of the composition to a population of subject produces, in plasma samples from the subjects, one or more of a mean $AUC_{(0-t)}$ for estradiol that is from 1123 pg·h/ml to 1755 pg·h/ml, a mean $AUC_{(0-\infty)}$ for estradiol that is from 1968 pg·hr/ml to 3075 pg·hr/ml, or a mean $C_{max}$ for estradiol that is from 52 pg/ml to 81 pg/ml. In some embodiments, administration of the composition to a population of subject produces, in plasma samples from the subjects, one or more of a mean $AUC_{(0-t)}$ for progesterone that is from 96 ng·hr/ml to 150 ng·hr/ml, a mean $AUC_{(0-\infty)}$ for progesterone that is from 105 ng·hr/ml to 164 ng·hr/ml, or a mean $C_{max}$ for progesterone that is from 71 ng/ml to 112 ng/ml. In some embodiments, administration of the composition to a population of subject produces, in plasma samples from the subjects, one or more of a mean $AUC_{(0-t)}$ for estrone sulfate that is from 7277 pg·hr/ml to 11370 pg·hr/ml, a mean $AUC_{(0-\infty)}$ for estrone sulfate that is from 9596 pg·hr/ml to 14994 pg·hr/ml, or a mean $C_{max}$ for estrone sulfate that is from 341 pg/ml to 533 pg/ml. In some embodiments, administration of the composition to a population of subject produces, in plasma samples from the subjects, one or more of a mean $AUC_{(0-t)}$ for total estrone that is from 161 pg·h/ml to 252 pg·h/ml, a mean $AUC_{(0-t)}$ for total estrone that is from 171 pg·hr/ml to 267 pg·hr/ml, or a mean $C_{max}$ for total estrone that is from 28 pg/ml to 44 pg/ml.

In some embodiments, method of treating a subject are provided. In some embodiments, the method comprises administering to the subject a pharmaceutical composition as described herein, wherein administration of the pharmaceutical composition produces, in a plasma sample from the subject, one or more parameters selected from: an $AUC_{(0-t)}$ for estradiol that is from 1123 pg·h/ml to 1755 pg·h/ml; an $AUC_{(0-\infty)}$ for estradiol that is from 1968 pg·hr/ml to 3075 pg·hr/ml; a $C_{max}$ for estradiol that is from 52 pg/ml to 81 pg/ml; an $AUC_{(0-t)}$ for progesterone that is from 96 ng·hr/ml to 150 ng·hr/ml; an $AUC_{(0-\infty)}$ for progesterone that is from 105 ng·hr/ml to 164 ng·hr/ml; a $C_{max}$ for progesterone that is from 71 ng/ml to 112 ng/ml; an $AUC_{(0-t)}$ for estrone sulfate that is from 7277 pg·hr/ml to 11370 pg·hr/ml; an $AUC_{(0-\infty)}$ for estrone sulfate that is from 9596 pg·hr/ml to 14994 pg·hr/ml; a $C_{max}$ for estrone sulfate that is from 341 pg/ml to 533 pg/ml; an $AUC_{(0-t)}$ for total estrone that is from 161 pg·h/ml to 252 pg·h/ml; an $AUC_{(0-\infty)}$ for total estrone that is from 171 pg·hr/ml to 267 pg·hr/ml; and a $C_{max}$ for total estrone that is from 28 pg/ml to 44 pg/ml.

III. EXAMPLES

The following examples are offered to illustrate, but not to limit, the claimed subject matter.

Example 1

Estradiol Solubility

In various experiments, suitable solvents were determined for providing sufficient solubility to make 2 mg of estradiol in a 100 mg fill mass, with a desired goal of achieving ~20 mg/g solubility for estradiol. Initial solubility experiments were done by mixing estradiol with various solvents, saturate the solution with the estradiol, equilibrate for at least 3 days and filter the un-dissolved particles and analyzing the clear supernatant for the amount of estradiol dissolved by HPLC.

Estradiol solubility experiments were performed. From this list at least one item (e.g. propylene glycol) is known to be unsuitable for encapsulation in more than 20% w/w concentration.

TABLE 8

| Ingredient | Solubility (mg/g) |
| --- | --- |
| PEG 400 | 105* |
| Propylene Glycol | 75* |
| Polysorbate 80 | 36* |
| TRANSCUTOL ® HP | 141 |
| CAPMUL ® PG8 | 31.2 |

*Literature reference—Salole, E.G. (1987) The Physicochemical Properties of Oestradiol, J Pharm and Biomed Analysis, 5, 635-640.

In further solubility studies, estradiol was soluble at least 6 mg/gm MIGLYOL® TRANSCUTOL® in ratios of 81:19 to 95:5, in MIGLYOL®; ethanol at 91:11, and in MIGLYOL®:CAPMUL® PG8 at 88:11, but not in MIGLYOL: TRANSCUTOL at 96:4, MIGLYOL®:LABRASOL® at 70:30 to 80:20, or MIGLYOL®:CAPMUL® PG8 at 86:14.

Example 2

It was desired to achieve 50 mg of progesterone suspended in a medium that can also solubilize 2 mg estradiol in a total capsule fill mass of 200 mg. In order to achieve this formulation, the required solubility of estradiol needs to be ~10 mg/g. A total fill weight of 200 mg was considered suitable for a size 5 oval soft gelatin capsule.

Additional solubility studies were performed to find solvent mixtures that might possibly be more suitable for soft gelatin encapsulation. Solubility studies were conducted with CAPMUL® PG8 and CAPMUL® MCM by mixing estradiol with various solvent systems and as before by analyzing for the amount of estradiol dissolved by HPLC after filtration. Results of these experiments are presented in Table 9. It can be seen from these results that mixtures containing MIGLYOL®:CAPMUL® PG8 at 50%; and also CAPMUL® MCM alone or in combination with 20% Polysorbate 80 can achieve sufficient solubility to meet the target of 10 mg/g. CAPMUL® PG8 mixed with MIGLYOL® at the 15 and 30% level did not provide sufficient solubility.

TABLE 9

| Ingredient | Solubility (mg/g) |
| --- | --- |
| MIGLYOL ®:CAPMUL ® PG8 (85:15) | 4.40 |
| MIGLYOL ®:CAPMUL ® PG8 (70:30) | 8.60 |
| TRANSCUTOL:MIGLYOL ® 812: CAPMUL PG8 (5:65:28) | >12 |
| TRANSCUTOL ®:MIGLYOL ® 812: CAPMUL ® PG8 (5:47:47) | >12 |
| MIGLYOL ®:CAPMUL ® PG8 (50:50) | 14.0 |
| CAPMUL ® MCM | 19.8 |
| Polysorbate 80:CAPMUL ® MCM (20:80) | 15.0 |

Example 3

Additional studies were performed to assess the stability of estradiol (4-6 mg) in solvent mixtures, as reported in Table 10. MIGLYOL® 812 with 4% TRANSCUTOL®precipitated on Hot/Cold cycling after 96 hours, while estradiol solubilized in MIGLYOL®:CAPMUL® blends at 30 and 50% or in CAPMUL® MCM alone, did not precipitate under the same conditions for a minimum of 14 days.

TABLE 10

| Formulation | Estradiol (mg/g) | Results Hot/Cold Cycling |
| --- | --- | --- |
| TRANSCUTOL ®: MIGLYOL ® 812 (4:96) | 4 | Crystallizes after 96 hours |
| MIGLYOL ® 812: CAPMUL ® PG8 (70:30) | 6 | Clear, after 14 days |
| MIGLYOL 812: CAPMUL ® PG8 (50:50) | 6 | Clear, after 14 days |
| TRANSCUTOL ®:MIGLYOL ® 812:CAPMUL ® PG8 (5:80:15) | 6 | Clear, after 14 days |
| CAPMUL ® MCM | 6 | Clear, after 14 days |

As shown in Table 11 below, it was found that 12 mg estradiol solubilized in MIGLYOL®:CAPMUL® PG8 50:50, CAPMUL® MCM, and in mixtures of TRANSCUTOL®: MIGLYOL®: CAPMUL® PG8 are stable and do not precipitate for at least 12 days.

TABLE 11

| Formulation | Estradiol (mg/g) | Results Hot/Cold Cycling |
| --- | --- | --- |
| MIGLYOL ® 812: CAPMUL ® PG8 (50:50) | 12 | Clear, after 12 days |
| TRANSCUTOL ®: MIGLYOL ® 812: CAPMUL ® PG8 (5:65:28) | 12 | Clear, after 12 days |
| TRANSCUTOL ®: MIGLYOL ® 812: CAPMUL ® PG8 (5:47:47) | 12 | Clear, after 12 days |
| CAPMUL ® MCM | 12 | Clear, after 12 days |

Example 4

In addition to determining physical stability of the estradiol solutions over time, it is necessary to determine if the fill material will be stable during the encapsulation process. One way to test these preparations is with the addition of water to the fill mass. As can be seen in Table 12, estradiol solutions at a concentration of 6 mg/g in Polyethylene Glycol 400 and CAPMUL® MCM are able to absorb a minimum of 7% water without recrystallization, whereas the same concentration in MIGLYOL® 812:CAPMUL® PG8 (75:25) precipitates.

Estradiol solutions at a concentration of 12 mg/g in Polyethylene Glycol 400 and CAPMUL® MCM are able to absorb a minimum of 7% water without recrystallization. All CAPMUL® PG8 containing formulations turned hazy on the addition of water. However, it should be noted that estradiol recrystallization was not observed, and the addition of water to CAPMUL® PG 8 alone (without any estradiol) also turns hazy on the addition of water.

TABLE 12

| Formulation | Estradiol (mg/g) | Results after addition of 7% water |
| --- | --- | --- |
| MIGLYOL ® 812:CAPMUL ® PG8 (75:25) | 6 | Precipitated |
| MIGLYOL ® 812:CAPMUL ® PG8 (50:50) | 12 | Hazy |
| TRANSCUTOL ®:MIGLYOL ® 812:CAPMUL ® PG8 (5:65:28) | 12 | Hazy |
| CAPMUL ® MCM | 12 | Clear |
| TRANSCUTOL ®:MIGLYOL ® 812:CAPMUL ® PG8 (5:47:47) | 12 | Hazy |
| Polyethylene Glycol 400 | 12 | clear |

Example 5

In an exemplary embodiment, a capsule is provided containing a fill material comprising:

TABLE 13

| Ingredient | Mg/Capsule |
| --- | --- |
| Estradiol Hemihydrate | 2.00 |
| Triglyceride of caprylic/capric acid (e.g., MIGLYOL ® 812) | qs |
| Diethylene Glycol Monoethylether (TRANSCUTOL ® HP) | 65.00 |
| Liquid lecithin | 1.63 |
| Butylated Hydroxytoluene | 0.13 |
| Total Fill Weight | 325 |

Example 6

In an exemplary embodiment, a capsule is provided containing a fill material comprising:

TABLE 14

| Ingredient | Mg/Capsule |
| --- | --- |
| Estradiol Hemihydrate | 2.00 |
| Monoglycerides/diglycerides of capric acid (e.g., CAPMUL ® MCM) | qs |
| Liquid lecithin | 1.63 |
| Polysorbate 80 | 97.5 |
| Total Fill Weight | 325 |

In an exemplary embodiment, a capsule is provided containing a fill material comprising:

TABLE 15

| Ingredient | Mg/Capsule | % w/w | Amount/Batch |
| --- | --- | --- | --- |
| Estradiol Hemihydrate | 2.03 | 0.62 | 20.2 g |
| Monoglycerides/diglycerides of capric acid (e.g., CAPMUL ® MCM) | 322.97 | 99.38 | 3.23 kg |
| Total | | 100 | 3.25 kg |

The above formulation is prepared as follows: estradiol is added to CAPMUL® MCM and mixed until dissolved.

Example 7

Progesterone Solubility

In various embodiments, both estradiol and progesterone may be dissolved in a solvent. In various embodiments, the solubility of both estradiol and progesterone will be such that a therapeutically effective dose may be obtained in a reasonably sized mass, generally considered to be between 1 mg and 1200 mg, preferably suitable for encapsulation in a size 3 to 22 oval or oblong capsule. For example, in various embodiments, 50 mg to 100 mg of progesterone may be dissolved in a volume of solvent; i.e., the solubility would be 50 mg to 100 mg per capsule. MIGLYOL® was attempted, and while it can be considered a good carrier for progesterone, it alone did not provide a desirable level of solubilization of estradiol (e.g., solubility of 12 mg/g may be desirable in various embodiments). Thus, MIGLYOL® may be used in embodiments comprising a suspension of progesterone, though MIGLYOL®, standing alone, is not desirable for use in embodiments having fully solubilized progesterone and/or estradiol.

As can be seen in Table 16, the solubility of progesterone in CAPMUL® MCM is ~73 mg/g. Therefore, by suspending 200 mg progesterone in 400 mg of solvent, part of the dose (~14%) is already dissolved and the remaining is still a suspension. In some aspects and embodiments, it is desired to minimize the partial solubility of progesterone in the formulation in order to minimize the possibility of recrystallization.

Based on 73 mg/g solubility, the capsule size required to make a capsule of 50 mg solubilized progesterone would be 685 mg. Therefore, it was shown that it would be feasible to make a 50 mg progesterone and 2 mg estradiol solubilized formulation. MIGLYOL® had the lowest solubility, but that solvent is unable to dissolve the estradiol, therefore under further experiments, it was decided to proceed with the second lowest or CAPMUL® MCM. It has also been found that 2 mg of estradiol may also be dissolved in 685 mg of CAPMUL® MCM.

TABLE 16

| Ingredient | Progesterone Solubility (mg/g) |
| --- | --- |
| CAPMUL ® MCM | 73.4 |
| CAPMUL ® PG8 | 95 |
| MIGLYOL ® 812 | 27.8 |
| CAPMUL ® MCM: GELUCIRE ® 44/14 (9:1) | 86.4 |
| CAPMUL ® MCM: GELUCIRE 44/14 (7:3) | 70.5 |
| CAPMUL ® MCM: GELUCIRE ® 44/14 (6:3) | 57.4 |

In addition, it has been found that the solubility of progesterone in a solvent of CAPMUL® MCM in combination with GELUCIRE® 44/14 in a 9:1 ratio increases the solubility to approximately 86 mg/g. Therefore, in various embodiments, progesterone and/or estradiol may be dissolved in a CAPMUL® MCM and GELUCIRE® 44/14 system, wherein the ratio of CAPMUL® MCM to GELUCIRE® 44/14 is 9:1.

TABLE 17

| Ingredient | Progesterone Solubility (mg/g) |
|---|---|
| CAPMUL® MCM: GELUCIRE 44/14 (9:1) | 86.4 |
| CAPMUL® MCM: GELUCIRE® 44/14 (7:3) | 70.5 |
| CAPMUL® MCM: GELUCIRE® 44/14 (6:4) | 57.4 |

Example 8

In an exemplary embodiment, a capsule is provided containing a fill material having fully solubilized progesterone and estradiol comprising:

TABLE 18

| Ingredient | Mass (mg) | % w/w | Qty/Capsule (mg) |
|---|---|---|---|
| Progesterone, USP, micronized | 50.00 | 7.14 | 50.00 |
| Estradiol Hemihydrate, USP | 2.03 | 0.29 | 2.03 |
| CAPMUL® MCM, NF | | 82.57 | 577.97 |
| GELUCIRE® 44/14, NF | | 10.0 | 70.00 |
| TOTAL | | 100.00 | 700.00 |

A capsule such as that shown in Table 18 may be manufactured in any suitable manner. For the purposes of this Example, mixing may be facilitated by an impellor, agitator, or other suitable means. Also for the purposes of this Example, heating and/or mixing may be performed under an inert or relatively inert gas atmosphere, such as nitrogen gas N2. Mixing and/or heating for the purposes of this Example may be performed in any suitable vessel, such as a stainless steel vessel.

For example, CAPMUL® MCM may be heated to between 30° C. to 50° C., more preferably from 35° C. to 45° C., and more preferably to 40° C.+/−2° C. GELUCIRE® 44/14 may be added to the CAPMUL® MCM and mixed until dissolved. The addition may occur all at once or may occur gradually over a period of time. Heat may continue to be applied during the mixing of the GELUCIRE® 44/14 and the CAPMUL® MCM.

Heat may be removed from the GELUCIRE® 44/14 and CAPMUL® MCM mixture. Estradiol Hemihydrate may be added to the mixture. The addition may occur all at once or may occur gradually over a period of time. Micronized progesterone may then be added to the GELUCIRE® 44/14, CAPMUL® MCM and Estradiol Hemihydrate mixture until dissolved. The addition may occur all at once or may occur gradually over a period of time.

Example 9

In an exemplary embodiment, a capsule is provided containing a fill material having suspended progesterone comprising:

TABLE 19

| Ingredient | mg/Capsule | % | Function |
|---|---|---|---|
| Micronized Progesterone | 200.00 | 30.77 | Active |
| Medium Chain Triglyceride (MIGLYOL® 812 or equivalent) | qs | qs | Carrier |
| Lecithin Liquid | 1.63 | 0.25 | Lubricant/Emulsifier |
| Butylated Hydroxytoluene (also referred to as "BHT") | 0.13 | 0.02 | Antioxidant |

The above formulation is prepared as follows: MIGLYOL® is heated to about 45° C. GELUCIRE® 44/14 is added and mixed until dissolved. BHT is added and mixed until dissolved. Progesterone is suspended and passed through a colloid mill. The resultant fill mass can be used for encapsulation.

In an exemplary embodiment, a capsule is provided containing a fill material having partially solubilized progesterone comprising:

TABLE 20

| Ingredient | Qty/Capsule (mg) | % w/w | Qty/Capsule (mg) | Amount/Batch (kg) |
|---|---|---|---|---|
| Micronized Progesterone, USP | 200.00 | 33.33 | Active | 2.0 |
| Monoglycerides/diglycerides/triglycerides of caprylic/capric acid (CAPMUL® MCM) | 394.0 | 65.67 | Carrier | 3.94 |
| Lauroyl polyoxyl-32-glycerides (GELUCIRE® 44/14 or equivalent) | 6.0 | 1 | Lubricant/Emulsifier | 0.06 |
| Total | 600.00 mg | 100 | | 6.0 kg |

For suspensions of progesterone and partially solubilized progesterone, GELUCIRE® 44/14 may be added at 1% to 2% w/w to increase viscosity. The above formulation is prepared as follows: CAPMUL® MCM is heated to about 65° C. GELUCIRE® 44/14 is added and mixed until dissolved. Heat is removed. Progesterone is added and the mixture is passed through a colloid mill. The resultant fill mass can be used for encapsulation.

Example 10

In an exemplary embodiment, a capsule is provided containing a fill material having suspended progesterone comprising:

TABLE 21

| Ingredient | % | mg/Capsule | Function |
|---|---|---|---|
| Micronized Progesterone | 30.77 | 200.00 | Active |
| Medium Chain Triglyceride (MIGLYOL® 812 or equivalent) | 65.93 | 428.55 | Carrier |

TABLE 21-continued

| Ingredient | % | mg/Capsule | Function |
|---|---|---|---|
| Lauroyl polyoxyl-32-glycerides (GELUCIRE ® 44/14 or equivalent) | 3.00 | 19.50 | Suspending Agent |
| Butylated Hydroxytoluene | 0.03 | 1.95 | Antioxidant |
| Total | 100 | 650 | |

In various embodiments, amounts of MIGLYOL® may be present in a range from about 35-95% by weight; GELUCIRE® 44/14 from about 0.5-30% by weight; and BHT from about 0.01-0.1% by weight.

Example 11

For the purposes of this Example, a particle size analysis is conducted by using the Beckman Device. A sample API comprising micronized progesterone in accordance with various embodiments is provided for analysis.

Figure 4:
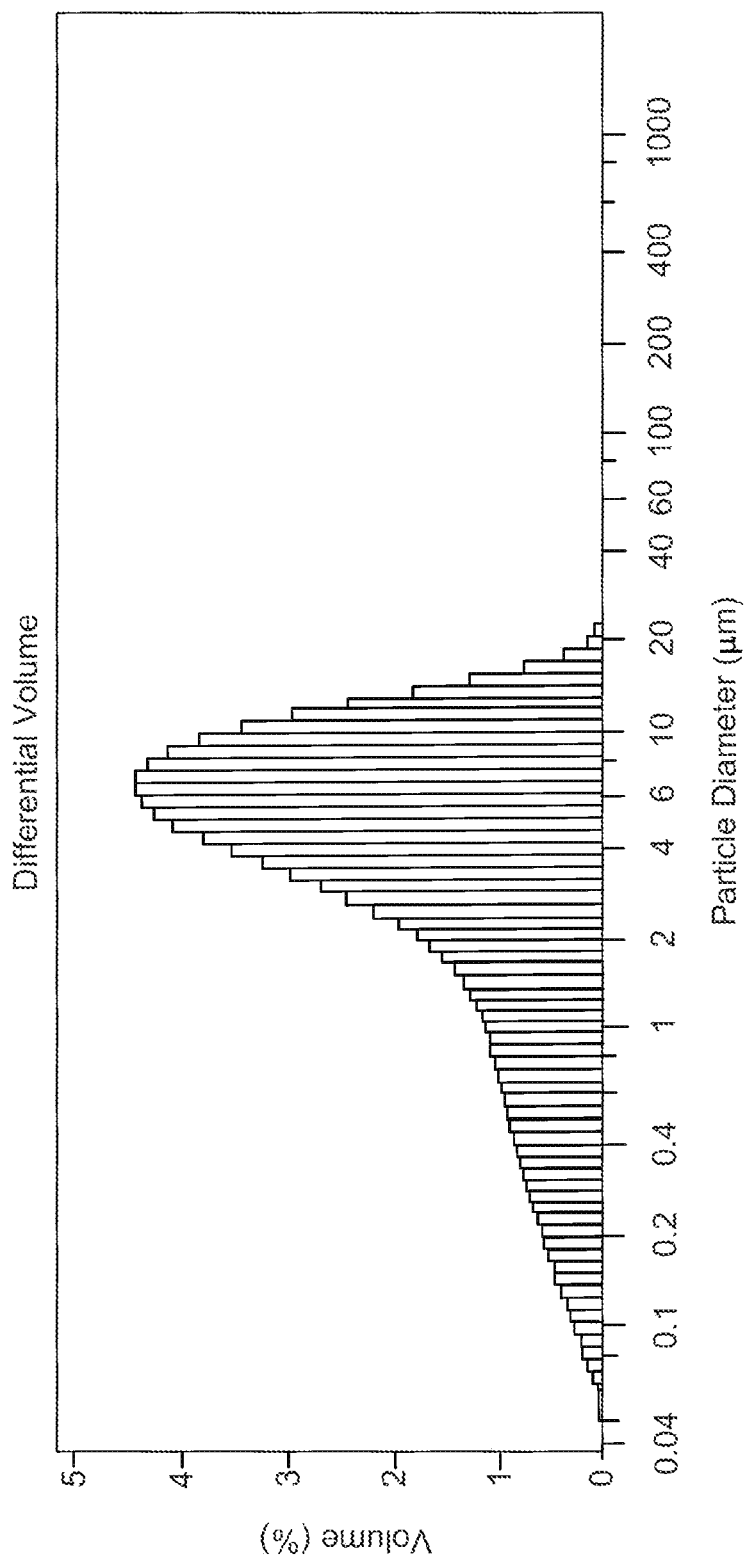
FIG. 4 illustrates a graph of the particle distribution obtained in Example 10.

Approximately 0.01 g of a sample API in accordance with various embodiments was combined with Coulter 1B and 10 mL of deionized water. Sonication was performed for 15 seconds. The Beckman Device, equipped with a ULM, performed analysis for 90 seconds. The Beckman Device was configured to use the Fraunhofer optical model. The Beckman Device yielded that the sample has an X50 of 4.279 µm, an X75 of 7.442 µm, and an X25 of 1.590 µm. The Beckman Device also yielded that the mean particle size is 4.975 µm, the median particle size is 4.279 µm, the mode particle size is 6.453 µm, and the standard deviation is 3.956 µm. A graph of the particle distribution obtained is shown in FIG. 4.

Example 12

A formulation sample having approximately 200 mg of micronized progesterone and 2 mg of estradiol was dispersed with oil. The Beckman Device, equipped with a MLM, performed analysis for 60 seconds. The Beckman Device was configured to use the Fraunhofer optical model. The Beckman Device yielded that the sample has an X50 of 11.0 µm, an X75 of 17.3 µm, and an X25 of 5.3 µm. The Beckman Device also yielded that the mean particle size is 11.8 µm, the median particle size is 11.04 µm, the mode particle size is 13.6 µm, and the standard deviation is 7.8 µm.

Example 13

In order to increase the solubility of progesterone in the final solution, GELUCIRE® 44/14 was added at about 10% w/w.

TABLE 22

Quantitative Formula: Batch Size 10,000 capsules

| Item No. | Ingredient(s) | Label Claim (mg) | % w/w | Qty/Capsule (mg) | Amount/Batch (kg) |
|---|---|---|---|---|---|
| 1. | Progesterone, USP, micronized | 50.00 | 7.14 | 50.00 | 0.50 |
| 2. | Estradiol Hemihydrate, USP | 2.03 | 0.29 | 2.03 | 0.02 |
| 3. | CAPMUL® MCM, NF | | 82.57 | 577.97 | 5.78 |

TABLE 22-continued

Quantitative Formula: Batch Size 10,000 capsules

| Item No. | Ingredient(s) | Label Claim (mg) | % w/w | Qty/Capsule (mg) | Amount/Batch (kg) |
|---|---|---|---|---|---|
| 4. | GELUCIRE® 44/14, NF | | 10.0 | 70.00 | 0.70 |
| | Total: | | 100.00 | 700.00 | 7.00 |

An example of the final formulation is provided in Table 22. The manufacturing process is as follows. CAPMUL® MCM is heated to 40° C. GELUCIRE® 44/14 is heated to 65° C. and added and mixed until dissolved. Heat is removed. Estradiol is added and mixed until dissolved. Micronized progesterone is then added and mixed until dissolved.

Example 14

In an exemplary embodiment, a capsule is provided containing a fill material having fully solubilized estradiol and partially solubilized progesterone comprising:

TABLE 23

| Item No. | Ingredient(s) | Label Claim (mg) | % w/w | Qty/Capsule (mg) | Amount/Batch (g) |
|---|---|---|---|---|---|
| 1. | Progesterone, USP, micronized | 50.00 | 25.000 | 50.00 | 500.00 |
| 2. | Estradiol Hemihydrate | 0.25 | 0.129 | 0.26 | 2.58 |
| 3. | CAPMUL® MCM, NF | | 73.371 | 146.74 | 1467.42 |
| 4. | GELUCIRE® 44/14, NF | | 1.500 | 3.00 | 30.00 |
| | Total: | | 100.00 | 200.00 mg | 2000.00 |

The manufacturing process is as follows. CAPMUL® MCM is heated to 65° C. GELUCIRE® 44/14 is added and mixed until dissolved. Heat is removed. Estradiol is added and mixed until dissolved. Micronized progesterone is then added and dispersed. The mixture is then passed through a colloid mill. The resultant fill mass can be used for encapsulation.

Example 15

In an exemplary embodiment, a capsule is provided containing a fill material having fully solubilized estradiol and partially solubilized progesterone comprising:

TABLE 24

| Item No. | Ingredient(s) | Label Claim (mg) | % w/w | Qty/Capsule (mg) | Amount/Batch (g) |
|---|---|---|---|---|---|
| 1. | Progesterone, USP, micronized | 200.00 | 33.33 | 200.0 | 2000.0 |
| 2. | Estradiol Hemihydrate | 2.00 | 0.35 | 2.07 | 20.7 |

TABLE 24-continued

| Item No. | Ingredient(s) | Label Claim (mg) | % w/w | Qty/ Capsule (mg) | Amount/ Batch (g) |
|---|---|---|---|---|---|
| 3. | CAPMUL ® MCM, NF | | 65.32 | 391.93 | 3919.3 |
| 4. | GELUCIRE ® 44/14, NF | | 1.00 | 6.0 | 60.0 |
| | Total: | | 100.00 | 600.0 mg | 6000.0 |

The manufacturing process is as follows. CAPMUL® MCM is heated to 65° C. GELUCIRE® 44/14 is added and mixed until dissolved. Heat is removed. Estradiol is added and mixed until dissolved. Micronized progesterone is then added and dispersed. The mixture is then passed through a colloid mill. The resultant fill mass can be used for encapsulation. Alternatively, GELUCIRE® 44/14 is heated to 65 C and CAPMUL® MCM is heated to 40 C+/−5 C to achieve mixing of the oil and the surfactant before heat is removed; estradiol is added while the mixture is cooling; progesterone is added when the mixture has dropped below about 4° C.; the mixture is then passed through a colloid mill, e.g., three times.

Example 16

Study 352—Progesterone and Estradiol Combination Study Under Fed Conditions

This following study protocol was used to establish bio-availability and bioequivalence parameters for a combination product of the present disclosure comprising progesterone (200 mg) and estradiol (2.0 mg) as prepared via the process described in Example 14 and compared to 200 mg of PROMETRIUM® (Catalent Pharmaceuticals, St. Petersburg, Fla. (and 2.0 mg of ESTRACE® (estradiol vaginal cream, USP, 0.01%) (Bristol-Myers Squibb Co. Princeton, N.J.), administered to twenty-four (24) normal healthy, adult human post-menopausal female subjects under fed conditions.

The pharmaceutical formulation of the invention used in these PK studies had substantially the following formula as shown in Table 25:

TABLE 25

| Ingredient(s) | Amount (% w/w) | Qty/Capsule (mg) |
|---|---|---|
| Progesterone, USP, micronized | 33.33 | 200.00 |
| Estradiol Hemihydrate, USP Micronized | 0.35 | 2.07 |
| CAPMUL MCM, NF, USP | 65.32 | 391.93 |
| GELUCIRE 44/14, NF | 1.00 | 6.00 |
| Total | 100.00 | 600 |

The Study Design: An open-label, balanced, randomized, two-treatment, two-period, two-sequence, single-dose, two-way crossover study. The subjects were housed in the clinical facility from at least 11.00 hours pre-dose to at least 48.00 hours post-dose in each period, with a washout period of at least 14 days between the successive dosing days.

Subjects were fasted for at least about 10.00 hours before being served a high-fat, high-calorie breakfast, followed by dosing, then followed by a 04.00 hour, post-dose additional period of fasting. Standard meals were provided at about 04.00, 09.00, 13.00, 25.00, 29.00, 34.00 and 38.00 hours post-dose, respectively. Water was restricted at least about 01 hour prior to dosing until about 01 hour post-dose (except for water given during dosing). At other times, drinking water was provided ad libitum. Subjects were instructed to abstain from consuming caffeine and/or xanthine containing products (i.e. coffee, tea, chocolate, and caffeine-containing sodas, colas, etc.) for at least about 24.00 hours prior to dosing and throughout the study, grapefruit and\or its juice and poppy containing foods for at least about 48.00 hours prior to dosing and throughout the study.

Subjects remained seated upright for about the first 04.00 hours post-dose and only necessary movements were allowed during this period. Thereafter subjects were allowed to ambulate freely during the remaining part of the study. Subjects were not allowed to lie down (except as directed by the physician secondary to adverse events) during restriction period.

Subjects were instructed not to take any prescription medications within 14 days prior to study check in and throughout the study. Subjects were instructed not to take any over the counter medicinal products, herbal medications, etc. within 7 days prior to study check-in and throughout the study.

After overnight fasting of at least about 10.00 hours, a high-fat high-calorie breakfast was served about 30 minutes prior to administration of investigational product(s). All subjects were required to consume their entire breakfast within about 30 minutes of it being served, a single dose of either test product (T) of Progesterone 200 mg & Estradiol 2 mg tablets or the reference product (R) PROMETRIUM® (Progesterone) soft gel Capsule 200 mg and ESTRACE® (Estradiol) Tablets 2 mg (according to the randomization schedule) were administered with about 240 mL of water under fed condition, at ambient temperature in each period in sitting posture. A thorough mouth check was done to assess the compliance to dosing.

All dosed study subjects were assessed for laboratory tests at the end of the study or as applicable.

In each period, twenty-three (23) blood samples were collected. The pre-dose (10 mL) blood samples at −01.00, −00.50, 00.00 hours and the post-dose blood samples (08 mL each) were collected at 00.25, 00.50, 00.67, 00.83, 01.00, 01.33, 01.67, 02.00, 0.50, 03.00, 04.00, 05.00, 06.00, 07.00, 08.00, 10.00, 12.00, 18.00, 24.00 and 48.00 hours in labeled K2EDTA—vacutainers via an indwelling cannula placed in one of the forearm veins of the subjects. Each intravenous indwelling cannula was kept in situ as long as possible by injecting about 0.5 mL of 10 IU/mL of heparin in normal saline solution to maintain the cannula for collection of the post-dose samples. In such cases, blood samples were collected after discarding the first 0.5 mL of heparin containing blood. Each cannula was removed after the 24.00 hour sample was drawn or earlier or if blocked.

At the end of the study, the samples were transferred to the bio-analytical facility in a box containing sufficient dry ice to maintain the integrity of the samples. These samples were stored at a temperature of −70° C.±20° C. in the bio-analytical facility until analysis.

Progesterone (corrected and uncorrected), estradiol (unconjugated), total estrone, and estrone sulfate in plasma samples is assayed using a validated LC-MS/MS method.

The pharmacokinetic parameters $C_{max}$, $AUC_{(0-t)}$ and $AUC_{(0-\infty)}$ were calculated on data obtained from 24 subjects for the test product and reference product. In general, bioavailability of progesterone and estradiol were similar but bioequivalence was not established.

Corrected pharmacokinetic profile summaries are presented in Table 26, below, for progesterone.

TABLE 26

Summary of Primary Pharmacokinetic Profile of Test Product (T) versus Reference Product (R) for Progesterone (Corrected)

| Pharmaco-kinetic Parameter | Geometric Mean* | | Arithmetic Mean ± Standard Deviation | |
|---|---|---|---|---|
| | Test Product (T) | Reference Product (R) | Test Product (T) | Reference Product (R) |
| $C_{max}$ | 47.0 | 43.0 | 81.0 ± 82.8 | 117.7 ± 173.7 |
| $AUC_{0-t}$ | 107.6 | 97.8 | 163.9 ± 136.5 | 191.1 ± 241.7 |
| $AUG_{0-\infty}$ | 110.7 | 110.0 | 173.5 ± 143.0 | 207.1 ± 250.3 |

*Estimate of Least Square Mean used to calculate Geometric Mean

Example 17

Study 351—Progesterone and Estradiol Combination Study Under Fasting Conditions

Fasted studies using the above protocol and test and reference products were also conducted. However, rather than the high-fat meal prior to administration of the test and reference drug, each subject fasted for a period of at least twelve (12) hours prior to dose administration.

The pharmacokinetic parameters $C_{max}$, $AUC_{(0-t)}$ and $AUC_{(0-\infty)}$ were calculated on data obtained from 23 subjects under fasting conditions for the test product and reference product. In general, bioavailability of progesterone and estradiol were similar but bioequivalence was not established.

Corrected pharmacokinetic profile summaries are presented in Table 27, below, for progesterone.

TABLE 27

Summary of Primary Pharmacokinetic Profile of Test Product (T) versus Reference Product (R) for Progesterone (Corrected)

| Pharmaco-kinetic Parameter | Geometric Mean* | | Arithmetic Mean ± Standard Deviation | |
|---|---|---|---|---|
| | Test Product (T) | Reference Product (R) | Test Product (T) | Reference Product (R) |
| $C_{max}$ | 2.3 | 3.0 | 2.9 ± 2.3 | 3.9 ± 3.4 |
| $AUC_{0-t}$ | 8.4 | 10.9 | 11.2 ± 8.7 | 14.5 ± 11.0 |
| $AUG_{0-\infty}$ | 12.9 | 17.2 | 15.1 ± 9.0 | 19.6 ± 10.2 |

*Estimate of Least Square Mean used to calculate Geometric Mean

The data indicate good (i.e., low) inter-patient and intra-patient variability relative to PROMETRIUM.

Example 18

Figure 2:
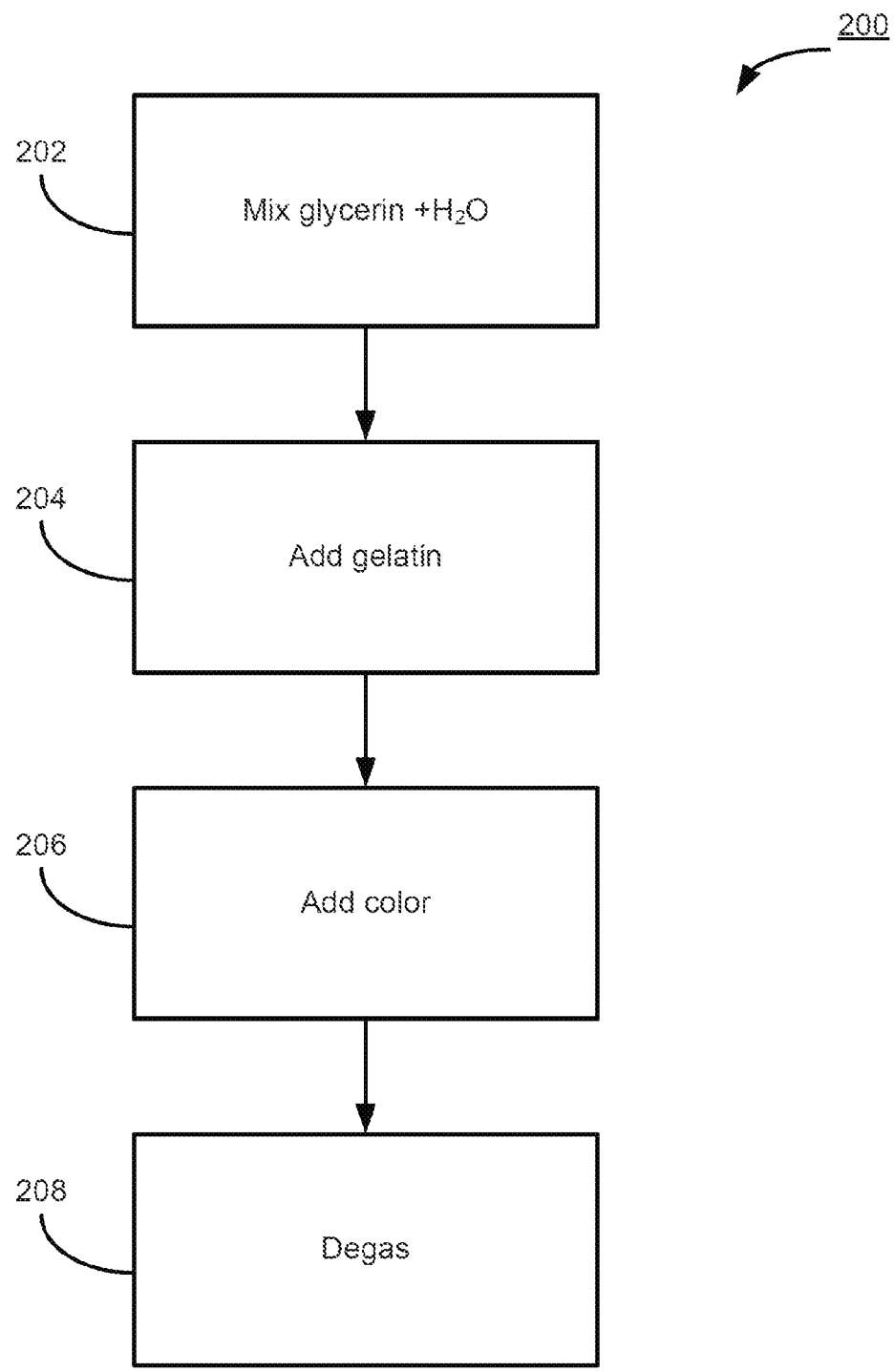
FIG. 2 illustrates an exemplary manufacturing process of a softgel material in accordance with various embodiments of the invention.
Figure 3:
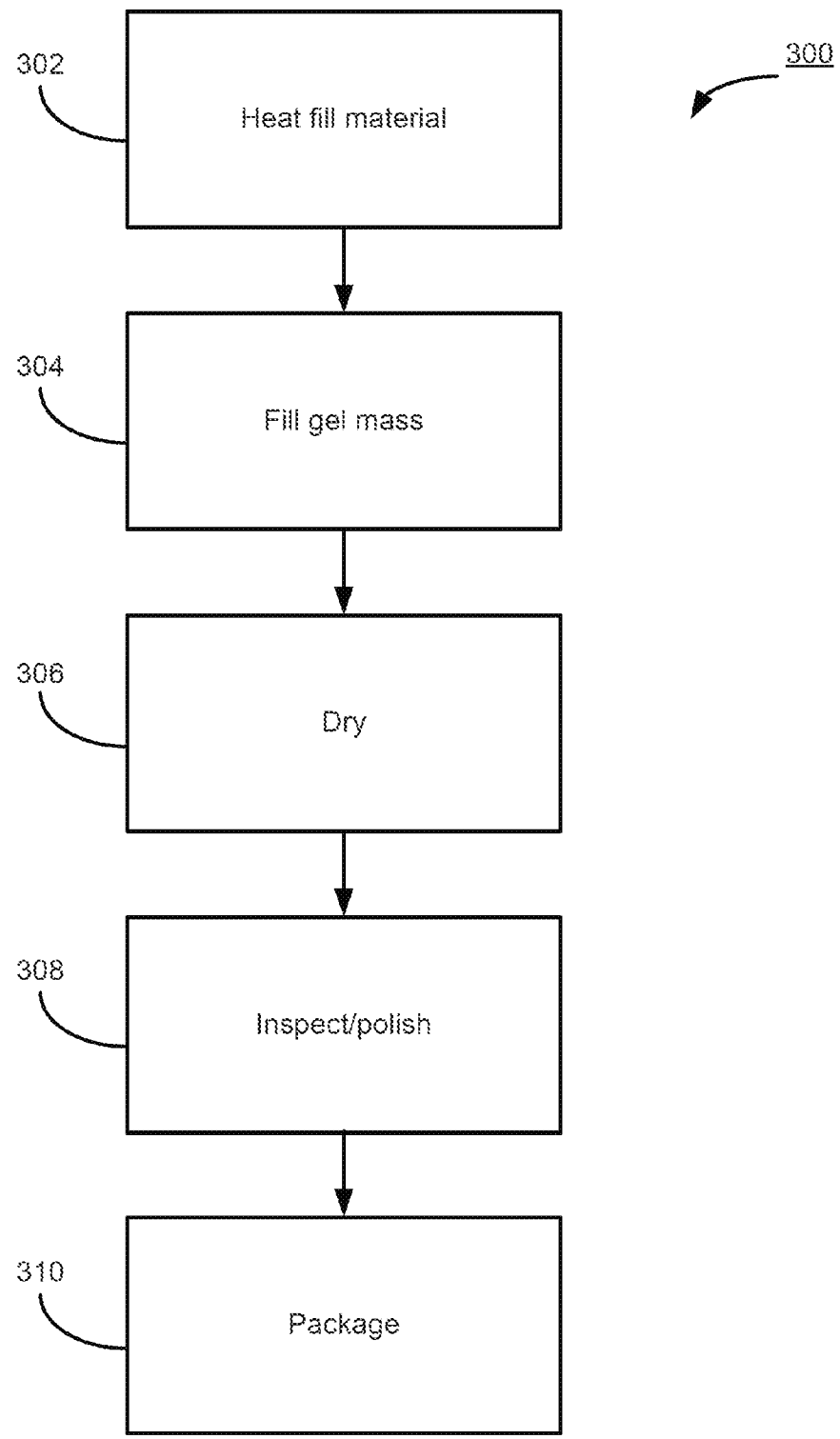
FIG. 3 illustrates an exemplary manufacturing process in accordance with various embodiments of the invention.

Methods of manufacture in accordance with various embodiments are shown in FIGS. 1-3. With reference to FIG. 1, method of fill material 100 is shown. Step 102 comprises heating an oily vehicle carrier to 40° C.±5° C. Heating may be accomplished through any suitable means. The heating may be performed in any suitable vessel, such as a stainless steel vessel. The oily vehicle may be any oily vehicle described herein, for example, CAPMUL® MCM.

Step 104 comprises mixing GELUCIRE® 44/14 with the oily vehicle. Mixing may be facilitated by an impeller, agitator, or other suitable means. Step 102 may be performed under an inert or relatively inert gas atmosphere, such as nitrogen gas N2. Mixing may be performed in any suitable vessel, such as a stainless steel vessel.

Step 106 comprises mixing estradiol into the mixture of the oily vehicle and GELUCIRE® 44/14. Mixing may occur in a steel tank or vat. Mixing may be facilitated by an impellor, agitator, or other suitable means. Step 106 may be performed under an inert or relatively inert gas atmosphere, such as nitrogen gas N2.

Step 108 comprises cooling to room temperature. Cooling may be allowed to occur without intervention or cooling may be aided by application of a cooling system.

Step 110 comprises mixing micronized progesterone into the mixture of oily vehicle, estradiol and GELUCIRE® 44/14. Mixing may occur in a steel tank or vat. Mixing may be facilitated by an impellor, agitator, or other suitable means. Step 110 may be performed under an inert or relatively inert gas atmosphere, such as nitrogen gas N2. Step 112 comprises degasing. The resulting mixture from step 112 may comprise a fill material suitable for production into a softgel capsule.

With reference to FIG. 2, softgel capsule, i.e. gel mass, production 200 is shown. Step 202 comprises mixing glycerin with water. The water used in step 202 may be purified by any suitable means, such as reverse osmosis, ozonation, filtration (e.g., through a carbon column) or the like. Mixing may be facilitated by an impeller, agitator, or other suitable means. Step 202 may be performed under an inert or relatively inert gas atmosphere, such as nitrogen gas N2. Heating may be performed until the temperature reaches 80° C.±5° C.

Step 204 comprises the addition of gelatin to the glycerin water mixture. Mixing may be facilitated by an impeller, agitator, or other suitable means. Step 204 may be performed under an inert or relatively inert gas atmosphere, such as nitrogen gas N2. A vacuum may be drawn in step 204 to de-aerate.

Step 206 comprises addition of a coloring agent such as a dye. A coloring agent may comprise products sold under the trademark OPATINT or other suitable agent. Step 206 may be performed under an inert or relatively inert gas atmosphere, such as nitrogen gas N2. Step 208 comprises degasing. The resulting mixture from step 208 may comprise a gel capsule material suitable for use as a gel capsule in production of a softgel capsule.

With reference to FIG. 3, softgel capsule assembly process 300 is shown. Step 302 comprises heating the fill material. The fill material may be heated to any suitable temperature. In various embodiments, the fill material is heated to 30° C.+/−3° C. Fill material may be heated in a fill hopper. A fill hopper may comprise a device configured to hold a volume of the fill material and/or to dispense the fill material in controlled volumes.

Step 304 comprises filling a gel mass. A gel mass may be taken from the gel capsule material produced in step 208 of FIG. 2. Filling may be performed by injecting, placing, or otherwise disposing the fill material within a volume defined by the gel capsule material. The filling may occur in an encapsulator. The spreader boxes may be a temperature of 55° C.+/−10° C. The wedge temperature may be 38° C.+/−3°

C. The drum cooling temperature may be 4° C.+/−2° C. The encapsulator may be lubricated using MIGLYOL® 812 or other suitable lubricant. Step 304 thus produces one or more softgel capsules. Filling may comprise producing a ribbon of thickness 0.85 mm±0.05 mm using spreader box knobs. The fill material may be injected into the gel to produce a fill weight having target weight±5% (i.e., 650±33 mg and 325±16.3 mg).

Step 306 comprises drying the softgel capsules. Drying may be performed in a tumble dryer, tray dryer, or combinations thereof. For example, drying may be performed in a tumble drying basket for between about 10 minutes and about 120 minutes. Drying may continue in a drying room for about 24 hours to about 72 hours. Step 308 may comprise inspection and/or polishing. Polishing may be performed with isopropyl alcohol. Step 310 may comprise packaging. Packaging may be accomplished through any suitable means. Packaging may comprise packing softgel capsules into a blister pack, bottle, box, pouch, or other acceptable packaging.

Example 19

I. Solubility of Estradiol in Soy Bean Oil, Peanut Oil, and Safflower Oil

Data was obtained visually by making the mixtures described below, sonicating the mixtures, and then seeing if a clear solution resulted. If a clear solution was achieved, it was an indication of solubility at the level studied.
Procedures and Results:
Step 1.
0.3% of Estradiol suspension in each oil was prepared by adding 30 mg Estradiol to solvent and QS to 10 g. Samples were mixed on vortex for 2 hours, heated at 50° C. for 30 minutes and then mixed for 1 hour more. All samples were still in suspension form.
Step 2.
Each sample was diluted to 0.24% (by adding 2.5 g more oil) and mixed for 2 hours and heated at 50° C. for 30 min and mixed again for one hour. All the samples were still cloudy. Samples were kept at room temperature overnight to see if they precipitate or if un-dissolved API settles out. After 20 hours at room temperature, it was observed that all samples still had un-dissolved API.
Step 3.
Each sample was diluted to 0.2% (by adding 2.5 g more oil) and mixed 2 for hours and heated at 50° C. for 30 min and mixed again for one hour. All the samples were still slightly cloudy, indicating that the estradiol was not completely dissolved.

TABLE 28

| Ingredient | Estradiol Solubility (mg/g) | Estradiol Solubility (% w/w) |
| --- | --- | --- |
| Peanut Oil | <2 | <0.2 |
| Safflower Oil | <2 | <0.2 |
| Soy Bean Oil | <2 | <0.2 |

The solubility of estradiol in all three oils was less than 2 mg/g (0.2% w/w). This level of solubility is significantly below the solubility that the present inventors have discovered can be achieved in other oils, e.g., medium chain fatty acid esters, such as the mono/diglycerides, propylene glycol esters, and polyethylene glycol esters discussed above.

In sum, if no heat is used to dissolve estradiol in safflower oil, it will not go into solution. Given that the estradiol did not dissolve at 50° C., oils such as safflower oil will not be useful in the methods of the invention using medium chain fatty acid esters as described hereinabove.

II. Solubility in Safflower Oil

In a separate experiment, 50 g of safflower oil was heated to 85-88° C. and 60 mg estradiol was added, mixed until fully dissolved (1 hr), and allowed to cool to room temperature. The solubility achieved was 1.0 mg/ml. Addition of progesterone to a sample of the estradiol solution did not affect the solubility of estradiol.

Unsaturated fats are prone to oxidation, i.e., rancidity. Peroxides are intermediates formed during oxidation and the Peroxide Value is an indicator of extent of oxidation. The US Pharmacopeia specification for Peroxide Value of safflower oil is 10 max. Heating the oil, e.g., to 85° C., has been shown to increase the Peroxide Value. In contrast, medium chain fatty acid glycols, such as CAPMUL® MCM and MYGLYOL® 812, which comprise saturated C8-C10 fatty acid esters, have much lower Peroxide Values, e.g., on the order of 1 or less.

Example 20

Dissolution

Dissolution studies were performed using a formulation of this invention comparing the dissolution of progesterone to the dissolution of PROMETRIUM® and comparing the dissolution of estradiol to the dissolution of ESTRACE®. In one study, a formulation of the invention in capsules comprising 200 mg of progesterone and 2 mg estradiol was used. In a second study, a formulation of the invention in capsules comprising 50 mg of progesterone and 2 mg estradiol was used. The two formulations comprised:

The dissolution study was performed using a USP dissolution apparatus (reciprocating cylinder) ("USP Apparatus 3"). The apparatus was set to 30 dips per minute. 250 mL of a solution of 0.1N HCl with 3% sodium lauryl sulfate was used at 37° C.

Figure 5:
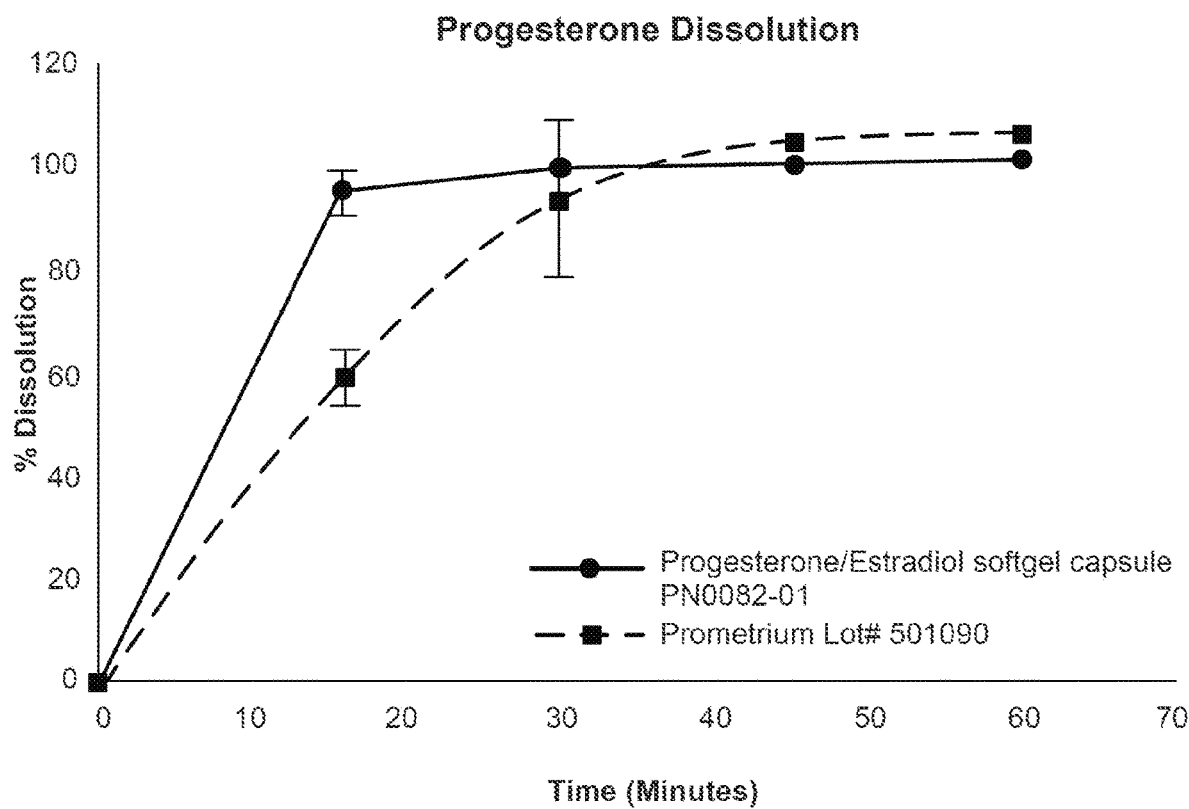
FIG. 5 illustrates a dissolution study of a formulation in accordance with various embodiments of the invention.

In both studies, progesterone was dissolved faster, and with smaller standard deviations, from the capsules of the invention than from PROMETRIUM®. Dissolution of estradiol was comparable but marginally slower from the capsules of the invention than from ESTRACE®. For illustrative purposes, a graph showing progesterone dissolution from the 200 mg progesterone capsule of the invention and from PROMETRIUM® is attached as FIG. 5.

Both capsules of the invention were stable on storage in white HDPE bottles. Positive stability data were obtained with the 200 mg progesterone formulation over 6 months (>6 months data unavailable) and with the 50 mg progesterone formulation over 3 months (>3 months data unavailable).

Example 21

Study 459—Combination Study Under Fed Conditions—Pharmacokinetics of the First Combination 17β-Estradiol/Progesterone Capsule in Clinical Development for Hormone Therapy The objective of this study was to evaluate the pharmacokinetic and oral bioavailability of a combination capsule of 17β-estradiol/progesterone in comparison to co-administration of the individual products ESTRACE® and PROMETRIUM®.

Subjects and Study Design:

An open label, balanced, randomized, single-dose, 2-treatment, 3-period, 3-sequence, crossover, partial-replicate, reference-scaled, oral, relative bioavailability study compared the bioavailability of an investigational 2-mg 17β-estradiol/200-mg progesterone combination capsule, without peanut oil (formulated in a manner similar to that set forth in Table 24), with that of co-administered 200-mg PROMETRIUM® (progesterone) and 2-mg ESTRACE® (17β-estradiol) tablets in healthy postmenopausal women aged 40-65 yrs (N=66). Key inclusion criteria for subjects included a BMI 18.50 to 29.99 kg/m² who were nonsmokers or ex-smokers (no smoking in the last 3 months). Key exclusion criteria for subjects included consuming grapefruit juice or poppy-containing foods within 48 hours before and throughout the study, use of any hormonal agent within 14 days before the study, and use of menopausal hormone therapy within 6 months before dosing.

Figure 6:
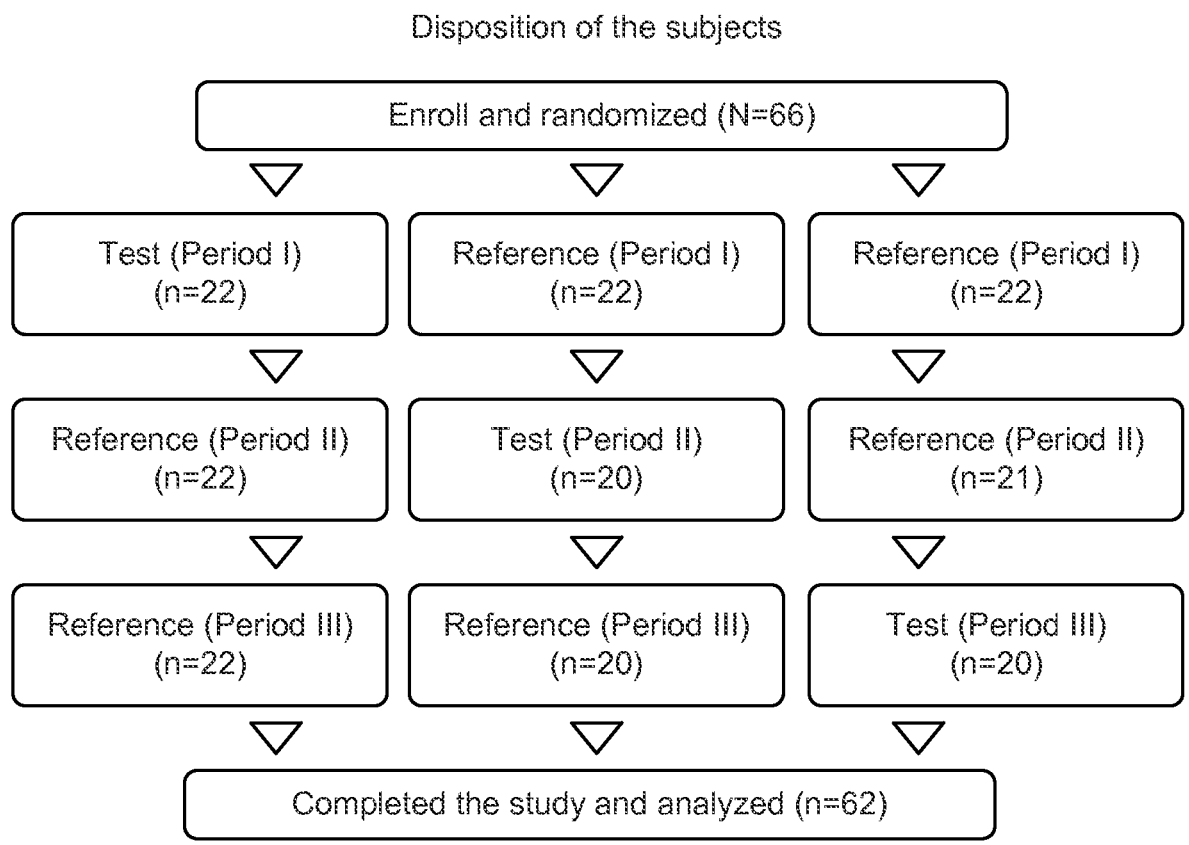
FIG. 6 illustrates a flow chart of subject disposition for a study comparing the bioavailability of a 17β-estradiol and progesterone combination formulation to the bioavailability of co-administered PROMETRIUM® and ESTRACE®.

Patients were randomly assigned sequentially to 1 of 3 dosing sequences of the same dose of the combination capsule (Test, T) and reference products (Reference, R): TRR, RTR, or RRT. 66 subjects were randomized and 62 (94.0%) completed the study (FIG. 6). Subjects had a mean age of 49.5±5.6 years (range 40 to 64) and a mean BMI of 24.8±3.1 kg/m² (range 18.7-29.9).

After consuming a high-fat, high-calorie breakfast, each woman received a single dose of the combination (Test) capsule in 1 period of the study and single doses of the co-administered products (Reference) in each of the 2 remaining periods. Plasma was collected pre-dose and at specified intervals over 48 h after dosing to determine progesterone, free (unconjugated) estradiol, and free and total (conjugated+free) estrone concentrations. The primary ($C_{max}$, $AUC_{0-t}$, and $AUC_{0-\infty}$) and secondary ($t_{max}$, $t_{1/2}$, and $K_e$) PK parameters for each analyte were determined for each subject during each period by non-compartment analyses using baseline-adjusted concentrations. Statistical analyses were conducted using the Scaled Average Bioequivalence (BE) method for highly variable drugs to determine whether the combination Test capsule had progesterone and estradiol bioavailability similar to that of the co-administered Reference products. This method is applicable when the within-subject coefficient of variation (CV) for the reference product is ≥30%. For any PK parameter with CV<30%, the BE method based on 90% CI must be used.

Figure 7:
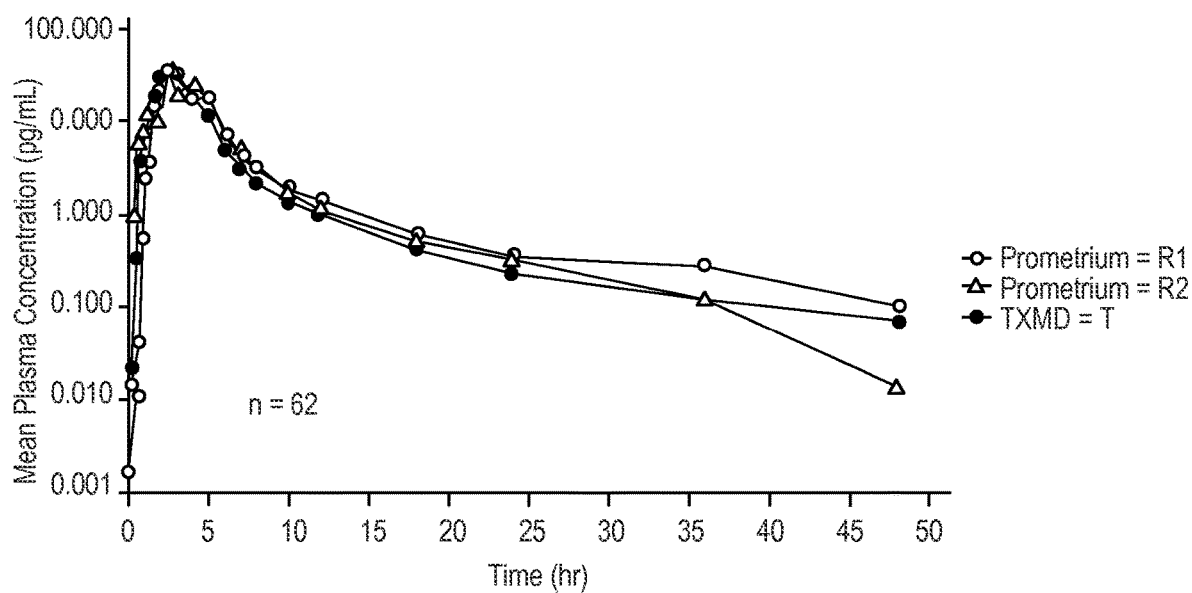
FIG. 7 illustrates pharmacokinetic parameters for progesterone for the combination formulation (T) versus co-administered PROMETRIUM® and ESTRACE® (R1 and R2).
Figure 8:
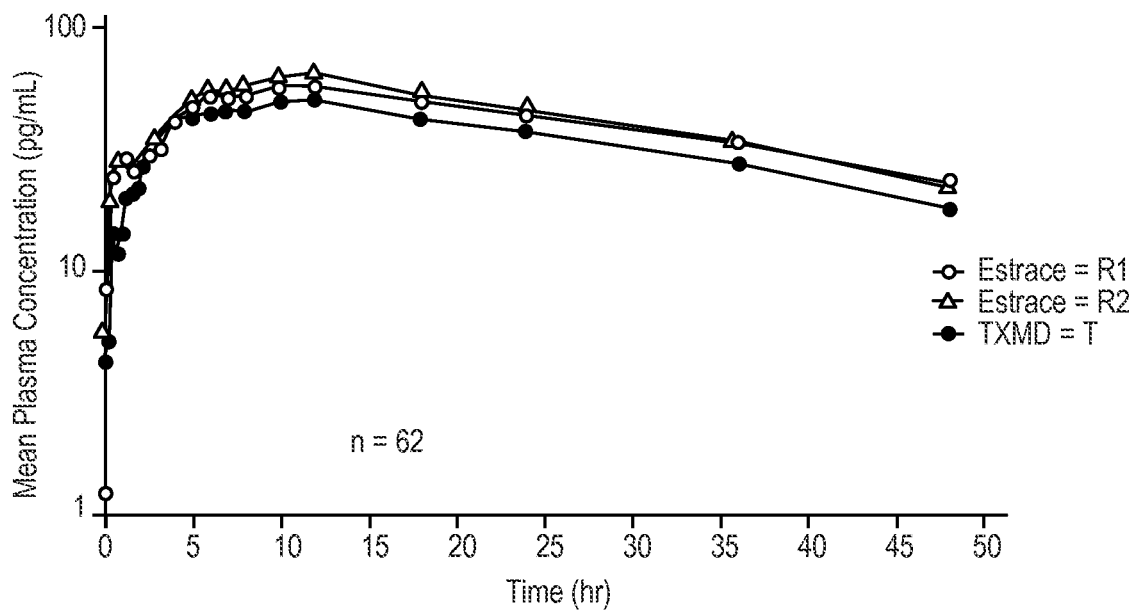
FIG. 8 illustrates pharmacokinetic parameters for free estradiol for the combination formulation (T) versus co-administered PROMETRIUM® and ESTRACE® (R1 and R2).

Results: All AUC and $C_{max}$ parameters met BE criteria for all analytes, except $C_{max}$ for total estrone (Table 29). The extent of estradiol and progesterone absorption for the Test capsule appeared to be similar to that for the ESTRACE® and PROMETRIUM® tablets, respectively (Table 29), while the rate of estradiol absorption for the Test capsule appeared to be faster than that for ESTRACE®, respectively (Table 30). Semilogarithmic plots of AUC over time for each analyte are presented in FIGS. 7 and 8. Pharmacokinetic data ($C_{max}$, $AUC_{(0-t)}$, and $AUC_{(0-\infty)}$) for progesterone, estradiol, free estrone, and total estrone is presented in Tables 31-34. For Tables 31-34, "Test Product (T)" refers to the progesterone+estradiol pharmaceutical composition, while "Reference product (R1)" and "Reference product (R2)" refer to co-administered PROMETRIUM® (progesterone) and ESTRACE® (estradiol).

The bioequivalent outcomes for progesterone should allow the Test capsule to bridge to the safety data for PROMETRIUM®. A bridge to the safety data for the ESTRACE® tablet should also be viewed as having been established because the only parameter for which the Test capsule failed to meet BE criteria was the $C_{max}$ for just 1 estradiol-related analyte (total estrone). The extent of estradiol absorption, reflecting the total amount of estradiol delivered by the Test capsule, is the most critical safety measure.

TABLE 29

Scaled Average Bioequivalence Analyses for Each Analyte

| Analyte/Parameter | Test-to-Ref Ratio | CV % | 95% Upper Confidence Bound | Meets BE Criteria† |
|---|---|---|---|---|
| Progesterone | | | | |
| $AUC_{(0-t)}$ | 1.05 | 122.2 | −0.5422 | Yes |
| $AUC_{(0-inf)}$ | 0.94 | 116.4 | −0.4941 | Yes |
| $C_{max}$ | 1.16 | 173.7 | −0.7850 | Yes |
| Unconjugated estradiol | | | | |
| $AUC_{(0-t)}$ | 0.93 | 42.6 | −0.0888 | Yes |
| $AUC_{(0-inf)}$ | 0.83 | 47.4 | −0.0625 | Yes |
| $C_{max}$ | 0.88 | 35.4 | −0.0399 | Yes |

| Analyte/Parameter | Test-to-Ref Ratio | CV % | 90% Confidence Interval | Meets BE Criteria |
|---|---|---|---|---|
| Unconjugated estrone | | | | |
| $AUC_{(0-t)}$ | 0.89 | 18.0 | 0.848-0.938 | Yes |
| $AUC_{(0-inf)}$ | 0.88 | 26.3 | 0.834-0.933 | Yes |
| $C_{max}$ | 0.93 | 23.3 | 0.873-0.991 | Yes |

TABLE 29-continued

Scaled Average Bioequivalence Analyses for Each Analyte

Total estrone

| | | | | |
|---|---|---|---|---|
| $AUC_{(0-t)}$ | 1.06 | 29.7 | 0.982-1.115 | Yes |
| $AUC_{(0-inf)}$ | 1.06 | 29.7 | 0.985-1.114 | Yes |
| $C_{max}$ | 1.75 | 35.9 | 0.3438* | No |

*95% Upper Confidence Bound
†Scaled Average Bioequivalence requires Test-to-Reference ratio between 0.800 and 1.250 and the 95% upper confidence bound on the linearized statistic is ≤0. Unscaled Average Bioequivalence requires that the 90% confidence interval on the Test-to-Reference ratio is entirely within 0.800 and 1.250.
BE = Bioequivalence;
CV % = coefficient of variance.

TABLE 30

$T_{max}$ for Each Analyte

| Analyte/Parameter | Test | Reference 1 | Reference 2 |
|---|---|---|---|
| Progesterone | 3.00 (0.83-10.0) | 3.00 (1.00-12.0) | 4.00 (0.67-18.0) |
| Unconjugated estradiol | 9.00 (0.50-36.0) | 10.0 (0.50-35.1) | 10.0 (0.25-36.6) |
| Unconjugated estrone* | 5.50 (0.83-36.0) | 8.00 (1.67-18.0) | 10.0 (1.67-18.0) |

TABLE 31

Summary of Pharmacokinetic Parameters of Test Product (T) versus Reference Product (R1, R2) for Progesterone (Corrected)

| PK Parameter | N | Test Product (T) | N | Reference Product (R1) | N | Reference Product (R2) |
|---|---|---|---|---|---|---|
| $C_{max}$ (ng/mL) Arithmetic Mean ± SD | 62 | 89.2222 ± 149.7309 | 62 | 72.7228 ± 101.8885 | 62 | 69.7590 ± 87.0777 |
| $C_{max}$ (ng/mL) Geometric Mean | 62 | 35.0996 | 62 | 30.6904 | 62 | 29.7178 |
| $AUC_{(0-t)}$ (ng · hr/mL) Arithmetic Mean ± SD | 62 | 120.0869 ± 164.1385 | 62 | 125.9406 ± 152.3483 | 62 | 111.5867 ± 113.3200 |
| $AUC_{(0-t)}$ (ng · hr/mL) Geometric Mean | 62 | 63.3952 | 62 | 61.5312 | 62 | 58.5421 |
| $AUC_{(0-\infty)}$ (ng · hr/mL) Arithmetic Mean ± SD | 57 | 131.3817 ± 172.4806 | 57 | 142.1332 ± 160.4853 | 56 | 126.6006 ± 117.2665 |
| $AUC_{(0-\infty)}$ (ng · hr/mL) Geometric Mean | 57 | 72.1098 | 57 | 79.9008 | 56 | 75.7201 |

TABLE 32

Summary of Pharmacokinetic Parameters of Test Product (T) versus Reference Product (R1, R2) for Estradiol (Corrected)

| PK Parameter | N | Test Product (T) | N | Reference Product (R1) | N | Reference Product (R2) |
|---|---|---|---|---|---|---|
| $C_{max}$ (pg/mL) Arithmetic Mean ± SD | 62 | 64.7902 ± 50.9833 | 62 | 69.1286 ± 33.0484 | 62 | 73.4236 ± 43.4077 |
| $C_{max}$ (pg/mL) Geometric Mean | 62 | 56.1068 | 62 | 62.2189 | 62 | 64.5362 |
| $AUC_{(0-t)}$ (pg · hr/mL) Arithmetic Mean ± SD | 62 | 1403.7333 ± 763.8136 | 62 | 1508.2206 ± 876.7390 | 62 | 1658.2502 ± 976.5556 |
| $AUC_{(0-t)}$ (pg · hr/mL) Geometric Mean | 62 | 1224.2031 | 62 | 1239.6990 | 62 | 1413.7331 |

TABLE 32-continued

Summary of Pharmacokinetic Parameters of Test Product (T) versus
Reference Product (R1, R2) for Estradiol (Corrected)

| PK Parameter | N | Test Product (T) | N | Reference Product (R1) | N | Reference Product (R2) |
|---|---|---|---|---|---|---|
| $AUC_{(0-\infty)}$ (pg · hr/mL) Arithmetic Mean ± SD | 60 | 2459.4394 ± 4498.2737 | 60 | 2842.8805 ± 4582.6502 | 57 | 2110.9591 ± 1175.3995 |
| $AUC_{(0-\infty)}$ (pg · hr/mL) Geometric Mean | 60 | 1658.0281 | 60 | 1879.6716 | 57 | 1796.6988 |

TABLE 33

Summary of Pharmacokinetic Parameters of Test Product (T) versus
Reference Product (R1, R2) for Total Estrone (Corrected)

| PK Parameter | N | Test Product (T) | N | Reference Product (R1) | N | Reference Product (R2) |
|---|---|---|---|---|---|---|
| $C_{max}$ (pg/mL) Arithmetic Mean ± SD | 61 | 35.4289 ± 17.0856 | 61 | 19.8716 ± 7.4485 | 61 | 19.9048 ± 8.0288 |
| $C_{max}$ (pg/mL) Geometric Mean | 61 | 31.9856 | 61 | 18.3037 | 61 | 18.4035 |
| $AUC_{(0-t)}$ (pg · hr/mL) Arithmetic Mean ± SD | 61 | 201.7524 ± 94.2081 | 61 | 182.7729 ± 88.8386 | 61 | 199.8295 ± 94.9392 |
| $AUC_{(0-t)}$ (pg · hr/mL) Geometric Mean | 61 | 182.7135 | 61 | 165.3741 | 61 | 182.1279 |
| $AUC_{(0-\infty)}$ (pg · hr/mL) Arithmetic Mean ± SD | 61 | 213.2402 ± 104.6011 | 60 | 193.6387 ± 100.5831 | 56 | 203.0289 ± 81.4884 |
| $AUC_{(0-\infty)}$ (pg · hr/mL) Geometric Mean | 61 | 191.4769 | 60 | 173.4694 | 56 | 187.8867 |

TABLE 34

Summary of Pharmacokinetic Parameters of Test Product (T) versus
Reference Product (R1, R2) for Estrone Sulfate

| PK Parameter | N | Test Product (T) | N | Reference Product (R1) | N | Reference Product (R2) |
|---|---|---|---|---|---|---|
| $C_{max}$ (pg/mL) Arithmetic Mean ± SD | 62 | 426.5492 ± 179.3303 | 62 | 455.5107 ± 189.4486 | 62 | 467.2302 ± 207.4373 |
| $C_{max}$ (pg/mL) Geometric Mean | 62 | 391.6591 | 62 | 416.8218 | 62 | 425.6676 |
| $AUC_{(0-t)}$ (pg · hr/mL) Arithmetic Mean ± SD | 62 | 9096.0907 ± 4377.2730 | 62 | 10156.0282 ± 5140.5831 | 62 | 10507.3557 ± 5183.1289 |
| $AUC_{(0-t)}$ (pg · hr/mL) Geometric Mean | 62 | 8043.8229 | 62 | 8872.7467 | 62 | 9204.9744 |
| $AUC_{(0-\infty)}$ (pg · hr/mL) Arithmetic Mean ± SD | 61 | 11994.9695 ± 6678.5468 | 62 | 13445.9048 ± 8699.4068 | 62 | 14066.2362 ± 7563.2370 |
| $AUC_{(0-\infty)}$ (pg · hr/mL) Geometric Mean | 61 | 10264.7576 | 62 | 11273.4294 | 62 | 11936.6967 |

For the test product pharmaceutical formulation, pharmacokinetic data ranges for AUC and $C_{max}$ are presented in Table 35 below.

TABLE 35 pK Ranges for the Test Product (T) Pharmaceutical Formulation

| | $C_{max}$ | $AUC_{(0-t)}$ | $AUC_{(0-\infty)}$ |
|---|---|---|---|
| Progesterone | 71 ng/mL to 112 ng/mL | 96 ng · hr/mL to 150 ng · hr/mL | 105 ng · hr/mL to 164 ng · hr/mL |
| Estradiol | 52 pg/mL to 81 pg/mL | 1123 pg · hr/mL to 1755 pg · hr/mL | 1968 pg · hr/mL to 3075 pg · hr/mL |
| Estrone sulfate | 341 pg/mL to 533 pg/mL | 7277 pg · hr/mL to 11370 pg · hr/mL | 9596 pg · hr/mL to 14994 pg · hr/mL |
| Total estrone | 28 pg/mL to 44 pg/mL | 161 pg · hr/mL to 252 pg · hr/mL | 171 pg · hr/mL to 267 pg · hr/mL |

CONCLUSION

The combination 17β-estradiol/progesterone capsule demonstrated similar bioavailability of its constituents to their individual respective references of ESTRACE® and PROMETRIUM®, when given together under fed conditions. This new capsule could represent an interesting development in hormone therapy, as no approved hormone therapy to date has been able to 1) combine natural progesterone with 17β-estradiol as an oral formulation, and 2) provide progesterone without peanut oil, a known allergen. The efficacy and safety of this new capsule combining 17β-estradiol with progesterone will be evaluated in phase 3 clinical trials.

It will be apparent to those skilled in the art that various modifications and variations can be made in the present disclosure without departing from the spirit or scope of the disclosure. Thus, it is intended that the present disclosure cover the modifications and variations of this disclosure provided they come within the scope of the appended claims and their equivalents.

Likewise, numerous characteristics and advantages have been set forth in the preceding description, including various alternatives together with details of the structure and function of the devices and/or methods. This disclosure is intended as illustrative only and as such is not intended to be exhaustive. It will be evident to those skilled in the art that various modifications may be made, especially in matters of structure, materials, elements, components, shape, size and arrangement of parts including combinations within the principles of the disclosure, to the full extent indicated by the broad general meaning of the terms in which the appended claims are expressed. To the extent that these various modifications do not depart from the spirit and scope of the appended claims, they are intended to be encompassed therein.

What is claimed is:

1. A pharmaceutical formulation for administering estradiol and progesterone to a female subject in need thereof, comprising:
    17β-estradiol, wherein at least about 80% of the estradiol in the formulation is solubilized;
    suspended progesterone;
    a solubilizing agent comprising a medium chain oil comprising fatty acid esters of glycerol, polyethylene glycol, or propylene glycol, or mixtures thereof, wherein the fatty acid esters are predominantly esters of C6 to C12 fatty acids; and
    a surfactant comprising at least one of lauroyl macrogol-32 glycerides, lauroyl polyoxyl-32 glycerides, or lauroyl polyoxylglycerides,
    wherein the surfactant is present in the formulation in an amount from 0.01 wt % to 10 wt % and the ratio of the medium chain oil to the surfactant is 8:1 or greater; and
    wherein when administered to a female subject, the formulation produces:
    (a) one or more progesterone-related pharmacokinetic parameters selected from: (i) an area under the curve $(AUC)_{(0-t)}$ for progesterone that is from 96 ng·hr/mL to 150 ng·hr/mL; (ii) an $AUC_{(0-\infty)}$ for progesterone that is from 105 ng·hr/mL to 164 ng·hr/mL; and (iii) a $C_{max}$ for progesterone that is from 71 ng/mL to 112 ng/mL; or
    (b) one or more stradiol-related pharmacokinetic parameters selected from: (i) an $AUC_{(0-t)}$ for estradiol that is from 1123 pg·hr/mL to 1755 pg·hr/mL; (ii) an $AUC_{(0-\infty)}$ for estradiol that is from 1968 pg·hr/mL to 3075 pg·hr/mL; and (iii) a $C_{max}$ for unconjugated estradiol that is from 52 pg/mL to 81 pg/mL.

2. The pharmaceutical formulation of claim 1, wherein administration of the formulation to the female subject produces both an $AUC_{(0-t)}$ for estradiol that is from 1123 pg·hr/mL to 1755 pg·hr/mL and a $C_{max}$ for unconjugated estradiol that is from 52 pg/mL to 81 pg/mL.

3. The pharmaceutical formulation of claim 1, wherein administration of the formulation to the female subject produces both an $AUC_{(0-t)}$ for progesterone that is from 96 ng·hr/mL to 150 ng·hr/mL and a $C_{max}$ for progesterone that is from 71 ng/mL to 112 ng/mL.

4. The pharmaceutical formulation of claim 1, wherein when administered to the female subject, the formulation further produces one or more of the following:
    (i) an $AUC_{(0-t)}$ for estrone sulfate that is from 7277 pg·hr/mL to 11370 pg·hr/mL;
    (ii) an $AUC_{(0-\infty)}$ for estrone sulfate that is from 9596 pg·hr/mL to 14994 pg·hr/mL; or
    (iii) a $C_{max}$ for estrone sulfate that is from 341 pg/mL to 533 pg/mL.

5. The pharmaceutical formulation of claim 4, wherein administration of the formulation to the female subject produces both an $AUC_{(0-t)}$ for estrone sulfate that is from 7277 pg·hr/mL to 11370 pg·hr/mL and a $C_{max}$ for estrone sulfate that is from 341 pg/mL to 533 pg/mL.

6. The pharmaceutical formulation of claim 1, wherein when administered to the female subject, the formulation further produces one or more of the following:
    (i) an $AUC_{(0-t)}$ for total estrone that is from 161 pg·hr/mL to 252 pg·hr/mL;
    (ii) an $AUC_{(0-\infty)}$ for total estrone that is from 171 pg·hr/mL to 267 pg·hr/mL; or
    (iii) a $C_{max}$ for total estrone that is from 28 pg/mL to 44 pg/mL.

7. The pharmaceutical formulation of claim 6, wherein administration of the formulation to the female subject produces both an $AUC_{(0-t)}$ for total estrone that is from 161 pg·hr/mL to 252 pg·hr/mL and a $C_{max}$ for total estrone that is from 28 pg/mL to 44 pg/mL.

8. The pharmaceutical formulation of claim 1, wherein at least 50% of the fatty acid esters in the oil have a fatty acid chain length of C6-C12.

9. The pharmaceutical formulation of claim 1, wherein at least 90% of the fatty acid esters in the oil have a fatty acid chain length of C6-C12.

10. The pharmaceutical formulation of claim 1, wherein the medium chain oil is present in the formulation in an amount from 55 wt % to 75 wt %.

11. The pharmaceutical formulation of claim 1, wherein the medium chain oil is a mixture of mono- and diglycerides of capric and caprylic acid.

12. The pharmaceutical formulation of claim 1, wherein the medium chain oil comprises a mixture of mono- and diglycerides of capric and caprylic acid, and the surfactant comprises lauroyl polyoxyl-32 glycerides.

13. The pharmaceutical formulation of claim 1, wherein the formulation comprises progesterone in an amount from 30 wt % to 35 wt %, estradiol in an amount from 0.01 wt % to 0.04 wt %, the medium chain oil in an amount from 55 wt % to 75 wt %, and the surfactant in an amount from 0.01 wt % to 10 wt %.

14. The pharmaceutical formulation of claim 1, wherein the ratio of the medium chain oil to the surfactant is from 60:1 to 70:1.

15. A method of treating a subject having one or more symptoms of estrogen deficiency, the method comprising administering to the subject an effective amount of the pharmaceutical formulation of claim 1.

16. The method of claim 15, wherein the subject is female.

17. The method of claim 15, wherein the subject is a woman having a uterus.

* * * * *

UNITED STATES PATENT AND TRADEMARK OFFICE
CERTIFICATE OF CORRECTION

PATENT NO. : 10,806,740 B2
APPLICATION NO. : 14/512046
DATED : October 20, 2020
INVENTOR(S) : Peter H. R. Persicaner et al.

Page 1 of 1

It is certified that error appears in the above-identified patent and that said Letters Patent is hereby corrected as shown below:

In the Claims

Column 46, Claim 1, Line 15: Delete "stradiol-related" and insert in its place --estradiol-related--.

Signed and Sealed this
Twenty-fourth Day of November, 2020

Andrei Iancu
*Director of the United States Patent and Trademark Office*